(12) United States Patent
Wilson et al.

(10) Patent No.: US 7,662,831 B2
(45) Date of Patent: Feb. 16, 2010

(54) TETRACYCLIC INDOLES AS POTASSIUM CHANNEL MODULATORS

(75) Inventors: Matthew A. Wilson, Royersford, PA (US); Gregory S. Welmaker, Collegeville, PA (US); Eugene J. Trybulski, Huntingdon Valley, PA (US); John A. Butera, Clarksburg, PA (US); Ronald L. Magolda, Wallingford, PA (US)

(73) Assignee: Wyeth LLC, Madison, NJ (US)

( * ) Notice: Subject to any disclaimer, the term of this patent is extended or adjusted under 35 U.S.C. 154(b) by 193 days.

(21) Appl. No.: 11/828,525

(22) Filed: Jul. 26, 2007

(65) Prior Publication Data

US 2008/0027090 A1 Jan. 31, 2008

Related U.S. Application Data

(60) Provisional application No. 60/820,512, filed on Jul. 27, 2006.

(51) Int. Cl.
*A61K 31/4748* (2006.01)
*C07D 471/08* (2006.01)

(52) U.S. Cl. .................. 514/284; 546/72; 548/425; 514/410

(58) Field of Classification Search .................. 514/284, 514/410; 546/72; 548/425
See application file for complete search history.

(56) References Cited

U.S. PATENT DOCUMENTS

| | | | |
|---|---|---|---|
| 3,498,988 A | 3/1970 | Houlihan et al. |
| 3,501,475 A | 3/1970 | Humber |
| 3,501,480 A | 3/1970 | Humber et al. |
| 3,501,481 A | 3/1970 | Archibald et al. |
| 3,501,497 A | 3/1970 | Bell |
| 3,507,880 A | 4/1970 | Altwicker |
| 3,509,134 A | 4/1970 | Davis et al. |
| 3,509,184 A | 4/1970 | Conover et al. |
| 3,511,852 A | 5/1970 | Roberts et al. |
| 3,514,461 A | 5/1970 | Albertson |
| 3,518,258 A | 6/1970 | Von Strandhtmann et al. |
| 3,518,269 A | 6/1970 | Brown et al. |
| 3,528,991 A | 9/1970 | Bell |
| 3,534,037 A | 10/1970 | Loev |
| 3,534,059 A | 10/1970 | Robinson |
| 3,535,326 A | 10/1970 | Yamamoto et al. |
| 3,538,112 A | 11/1970 | Bell |
| 3,539,557 A | 11/1970 | Davis et al. |
| 3,539,576 A | 11/1970 | Davis et al. |
| 3,539,577 A | 11/1970 | Davis et al. |
| 3,539,588 A | 11/1970 | Salley |
| 3,541,117 A | 11/1970 | Schroff |
| 3,542,787 A | 11/1970 | Dobson et al. |
| 3,549,644 A | 12/1970 | Shavel et al. |
| 3,557,087 A | 1/1971 | Levine |
| 3,557,122 A | 1/1971 | Shavel et al. |
| 3,558,667 A | 1/1971 | Mooradian |
| 3,578,678 A | 5/1971 | Littell et al. |
| 3,579,534 A | 5/1971 | Littell et al. |
| 3,580,926 A | 5/1971 | Short |
| 3,584,009 A | 6/1971 | Gregory |
| 3,590,031 A | 6/1971 | Levine |
| 3,592,824 A | 7/1971 | Schut |
| 3,597,433 A | 8/1971 | Dobson et al. |
| 3,597,436 A | 8/1971 | Huisman et al. |
| 3,598,836 A | 8/1971 | Osaska et al. |
| 3,621,027 A | 11/1971 | Schoen et al. |
| 3,624,126 A | 11/1971 | Narayanan |
| 3,632,591 A | 1/1972 | Albertson et al. |
| 3,642,785 A | 2/1972 | Shen et al. |
| 3,642,836 A | 2/1972 | Cusic |
| 3,651,059 A | 3/1972 | Serino et al. |
| 3,652,544 A | 3/1972 | Levine |
| 3,655,697 A | 4/1972 | Shen et al. |
| 3,657,243 A | 4/1972 | Quintilla |
| 3,663,607 A | 5/1972 | Barrett et al. |
| 3,674,875 A | 7/1972 | Shen et al. |
| 3,679,662 A | 7/1972 | Morita et al. |
| 3,682,985 A | 8/1972 | Basco et al. |
| 3,687,969 A | 8/1972 | Alexander et al. |
| 3,689,488 A | 9/1972 | Dukes |
| 3,691,243 A | 9/1972 | Fields et al. |

(Continued)

FOREIGN PATENT DOCUMENTS

CA 2417677 7/2001

(Continued)

OTHER PUBLICATIONS

Edwards, G., et al., "Pharmacology of the potassium channel openers", *Cardiovasc. Drugs Ther.*, 9 (Suppl.2): 185-193, 1995.

(Continued)

*Primary Examiner*—Charanjit S Aulakh
(74) *Attorney, Agent, or Firm*—Pepper Hamilton LLP

(57) ABSTRACT

The present invention is directed to compounds of Formula I:

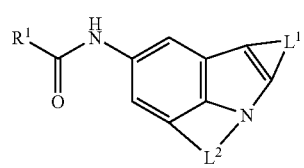

that are potassium channel modulators and pharmaceutical compositions thereof. The present invention is further directed to methods of treatment using the compounds and pharmaceutical compositions of the invention. The present invention is still further directed to synthetic processes for producing the compounds of the invention.

51 Claims, No Drawings

U.S. PATENT DOCUMENTS

| | | | |
|---|---|---|---|
| 3,705,906 A | 12/1972 | Narayanan et al. |
| 3,706,736 A | 12/1972 | Jeger et al. |
| 3,711,511 A | 1/1973 | Jeger et al. |
| 3,717,641 A | 2/1973 | Koesis et al. |
| 3,718,678 A | 2/1973 | Farrand et al. |
| 3,723,483 A | 3/1973 | Coombs |
| 3,726,897 A | 4/1973 | Schindler |
| 3,733,330 A | 5/1973 | Schubert et al. |
| 3,759,948 A | 9/1973 | Shen et al. |
| 3,773,940 A | 11/1973 | Schindler |
| 3,773,949 A | 11/1973 | Macelesfield |
| 3,830,818 A | 8/1974 | Hackmack et al. |
| 3,836,671 A | 9/1974 | Barrett et al. |
| 3,838,135 A | 9/1974 | Magnien et al. |
| 3,865,830 A | 2/1975 | Turkevich et al. |
| 3,865,834 A | 2/1975 | Schubert et al. |
| 3,883,654 A | 5/1975 | Hackmack et al. |
| 3,891,656 A | 6/1975 | Fields |
| 3,928,380 A | 12/1975 | Bell et al. |
| 3,931,288 A | 1/1976 | Berger et al. |
| 3,948,939 A | 4/1976 | Alexander et al. |
| 3,959,309 A | 5/1976 | Mooradian |
| 3,994,887 A | 11/1976 | Crooij et al. |
| 3,997,519 A | 12/1976 | Armbruster |
| 4,018,743 A | 4/1977 | Kraft et al. |
| 4,046,752 A | 9/1977 | Hohmann |
| 4,904,797 A | 2/1990 | Boshagen et al. |
| 5,017,597 A | 5/1991 | Gillard |
| 5,708,187 A | 1/1998 | Flaugh |
| 5,846,995 A | 12/1998 | Flaugh et al. |
| 5,858,995 A | 1/1999 | Kawai et al. |
| 6,197,768 B1 | 3/2001 | Ohashi et al. |
| 6,476,021 B1 | 11/2002 | Ohashi et al. |

FOREIGN PATENT DOCUMENTS

| | | |
|---|---|---|
| DE | 1210638 | 2/1966 |
| DE | 4238553 | 5/1994 |
| EP | 0247266 | 12/1987 |
| EP | 0297651 | 1/1989 |
| EP | 0344015 | 11/1989 |
| EP | 0350129 | 1/1990 |
| EP | 0375045 | 6/1990 |
| EP | 0425906 | 10/1990 |
| EP | 0441517 | 8/1991 |
| EP | 0451634 | 10/1991 |
| EP | 0468785 | 1/1992 |
| EP | 640592 | 3/1995 |
| EP | 0655451 | 5/1995 |
| EP | 0749962 | 12/1996 |
| EP | 0768309 | 4/1997 |
| EP | 0992240 | 4/2000 |
| EP | 1118322 | 7/2001 |
| EP | 1136072 | 9/2001 |
| EP | 1462103 | 9/2004 |
| GB | 1260768 | 1/1972 |
| GB | 1265627 | 3/1972 |
| GB | 1299041 | 12/1972 |
| GB | 1322512 | 7/1973 |
| GB | 1323302 | 7/1973 |
| GB | 1323491 | 7/1973 |
| GB | 1385620 | 2/1975 |
| GB | 1471847 | 4/1977 |
| GB | 1519495 | 7/1978 |
| GB | 1532684 | 11/1978 |
| GB | 2316405 | 2/1998 |
| JP | 5001032 | 1/1993 |
| JP | 61282384 | 12/1996 |
| WO | WO 90/12569 | 11/1990 |
| WO | WO 92/12144 | 7/1992 |
| WO | WO 93/00086 | 1/1993 |
| WO | WO 94/09009 | 4/1994 |
| WO | WO 94/14773 | 7/1994 |
| WO | WO 94/25461 | 11/1994 |
| WO | WO 95/29907 | 11/1995 |
| WO | WO 98/06717 | 2/1998 |
| WO | WO 98/53819 | 12/1998 |
| WO | WO 99/17755 | 4/1999 |
| WO | WO 99/26946 | 6/1999 |
| WO | WO 99/28319 | 6/1999 |
| WO | WO 99/54295 | 10/1999 |
| WO | WO 00/18391 | 4/2000 |
| WO | WO 00/24727 | 5/2000 |
| WO | WO 00/32195 | 6/2000 |
| WO | WO 00/63171 | 10/2000 |
| WO | WO 0145685 | 6/2001 |
| WO | WO 01/95903 | 12/2001 |
| WO | WO 02/07713 | 1/2002 |
| WO | WO 02/34237 | 5/2002 |
| WO | WO 02/41918 | 5/2002 |
| WO | WO 02/051806 | 7/2002 |
| WO | WO 2004/069831 | 8/2004 |
| WO | WO 2005/037791 | 4/2005 |
| WO | WO 2006/001318 | 1/2006 |

OTHER PUBLICATIONS

Foster, D.C., et al., "The effect of potassium channel antagoists on the BRL 34915 activated potassium channel in guinea-pig bladder", *Br. J. Pharmacol.*, 92:751, 1987.

Brading, A.F., "Ion channels and control of contractile activity in urinary bladder smooth muscle", *JPN J. Pharmacol.*, 58 (Suppl. 2): 120P-127P, 1992.

Malmgren, A., et al., "Effects of cromakalim (BRL 34915) and pinacidil on normal and hypertrophied rat detrusor in vitro", *J. Urol.*, 143:828-834, 1990.

Grant, T.L., et al., "Effects of $K^+$ channel blockers and cromakalim (BRL 34915) on the mechanical activity of guinea pig cetruso smooth muscle", *J. Pharmacol. Exp., Ther.*, 269(3):1158-1164, 1991.

Malmgren, A., et al., "Effects of pinacidil and cromakalim (BRL 34915) on bladder function in rats with detrusor instability", *J. Urol.*, 142:1134-1138, 1989.

Wojdan, A., et al., "Comparison of the potassium channel openers ZD6169, celikalim and WAY-133537 on isolated bladder tissue and in vivo bladder instability in the rat", *J. Pharmacol. Exp. Ther.*, 289(3):1410-1418, 1999.

Wickenden, A.D., et al., "Retigabine, a novel anti-convulsant, enhances activation of KCNQ2/Q3 potassium channels", *Molec. Pharmacol.* 58:591-600, 2000.

Wickenden, A.D., et al., "Characterization of the KCNQ5/Q3 potassium channels expressed in mammalian cells", *Br. J. Pharmacol.*, 132(2):381-384, 2001.

Rundfeldt, C., et al., "The novel anticonvulant retigabine activates M-currents in Chinese hamster ovary-cells transfected with human KCNQ2/3 subuints", *Neurosci. Lett.*, 282(1-2): 73-76, 2000.

Main, M.J., et al., "Modulation of KCNQ2/3potassium channels by the novel anticonvulsant retigabine", *Mol. Pharmacol.*, 58(2):253-262, 2000.

Sogaard, R., et al., "KCNQ4 channels expressed in mammalian cells: functional characteristics and pharmacology", *Am. J. Physiol. Cell Physiol.*, 280(4):C859-C866, 2001.

Kubisch, C., et al., "KCNQ4, a novel potassium channel expressed in sensory outer hair cells, is mutated in dominant deafness", *Cell*, 96(3):437-446, 1999.

Rogawski, M.A., "KCNQ2/KCNQ3 $K^+$ channels and the molecular pathogenesis of epilepsy: implications for therapy", *Trends Neurosci.*, 23:393-398, 2000.

Jentsch, T.J., "Neuronal KCNQ potassium channels: physiology and role in disease", *Nat. Rev. Neurosci.*, 1(1):21-30, 2000.

Tinel, N., et al., "The KCNQ2 potassium channel: splice variants, functional and developmental expression. Brain localization and comparison with KCNQ3", *FEBS Lett.*, 438(3):171-176, 1998.

Yang, W.P., et al., "Functional expression of two KvLQt1-related potassium channels responsible for an inherited idiopathic epilepsy", *J. Biol. Chem.*, 273(31): 19419-19423, 1998.

Wang, H.S., et al., "KCNQ2 and KCNQ3 potassium channel subunits: molecular correlets of the M-channel", *Science*, 282(5395):1890-1893, 1998.

Lerche, C., et al., "Molecular cloning and functional expression of KCNQ5, a potassium channel subunit that may contribute to neuronal M-current diversity", *J. Biol. Chem.*, 275(29):22395-22400, 2000.

Schroeder, B.C., et al., "KCNQ5, a novel potassium channel broadly expressed in brain, mediates M-type currents", *J. Biol. Chem.*, 275(31):24089-24095, 2000.

Adams, P.R., et al., "M-currents and other potassium currents in bullfrog sympathetic neurons", *J. Physiol.*, 330:537-572, 1982.

Brown, D.A., et al., "Muscarinic suppression of novel voltage-sensitive K$^+$current in a vertebrate neurone", *Nature*, 283:673-676, 1980.

Shapiro, M.S., et al., "Reconstitution of muscarinic modulation of the KCNQ2/KCNQ3 K(+) channels that underlie the neuronal M current", *J. Neurosci.*, 20(5):1710-1721, 2000.

Aiken, S.P., et al., "Reduction of spike frequency adaptation and blockade of M-current in rat CA1 pyramidal neurons by linopirdine (DuP 996) a neurotransmitter release enhancer", *Br. J. Pharmacol.*, 115(7):1163-1168, 1995.

Zaczek, R., "Two new potent neurotransmitter release enhancers, 10,10-bis(4-pyridinymethyl)-9(10H)-anthracenone and 10,10-bis(2-fluro-4-pyridinylmethyl)-9(10H)-anthracenone: comparison to linopirdine", *J. Pharmacol., Exp.Ther.*, 285(2): 724-730, 1998.

Hashitani, H., et al., "Mechanisms of excitatory neuromuscular transmission in the guinea-pig urinary bladder", *J. Physiol.*, 524(Part 2): 565-579, 2000.

Herrera, G.M., et al., "Voltage dependence of the coupling of CA(2+) sparks to BK(Ca)channels in urinary bladder smooth muscle", *Am. J. Physiol. Cell Physio.*, 280(3):C481-490, 2001.

Jacques, et al., *Enantiomers, Racemates and Resolutions* (Wiley Interscience, New York), 1981.

Eliel, E.L., *Stereochemistry of Carbon Compounds* (McGraw Hill, New York), 1962.

*Remington's Pharmaceutical Sciences*, 17$^{th}$ ed., Mack Publishing Company, Easton, PA, 1985, p. 1418.

*Journal of Pharmaceutical Science*, 66, 2 , 1977.

*Bioreversible Carriers in Drug Design*, ed. Edward B. Roche, American Pharmaceutical Association and Pergamon Press, 1987.

Green et al., *Protective Groups in Organic Synthesis*, 2d., Ed., Wiley & Sons, 1991.

Block, et al., "Discovery and Optimizatiaon of a Series of Carbazole Ureas as NPY5 Antagonists for the Treatment of Obesity", *J. Med. Chem.*, 45, 3509, 2002.

Hogget, et al., *Nitration and Aromatic Reactivity*, 122-145, 163-222, Cambridge University Press, 1971.

Rylander, *Organic Synthesis with Nobel Metal Catalysits*, pp. 1-59, Academic Press, New York, 1973.

Robinson, *The Fischer Indole Synthesis*, Wiley, New York, 1983.

Foster, C.D., et al., "The effect of cromakalim on the smooth muscle of the guinea-pig urinary bladder ", *Br. J. Pharmacol.*, 97:281-291, 1989.

Fujii, K., et al., "Potassium channel blockers and the effects of cromakalim on the smooth muscle of the guinea-pig bladder", *Br. J. Pharmacol.*, 99:779-785, 1990.

Vazanna, I., et al., "7-(substituted amino)-2,3-polymethylenebenzofuran derivatives with tracheal relaxant activity", *Il Farmacao*, 51(10):637-642, 1996.

Hayashi, T., "Tervalent Nitrogen.II. Carbazoleacridone and its several monosubstituted products", *Rikagaku Kenkyusho Iho*, 9:970-90, 1931.

Grammaticakis, P., [Preparation and absorption in the visible and ultraviolet region of various amino and nitro N-substituted-1,2,3,4-tetrahydrocarbazoles], *Compt. Rend*, 251, 2728-30, 1960.

Brunton, R.J., et al., "Preparation of indolocarbazoles. IX. Preparation of 9-methylindolo(2',3-1,2)carbazole", *J. Chem. Soc.* 4783-5, cf. C.A. 51,363f, 1956.

Kuroki, N. et al., "Dyes from carbazole derivatives. I. Synthesis of naphthol bases", *J. Soc. Org. Synthet.Chem. Japan*, 12:29-34, 1954.

Wilen, S.H., et al., *Tetrahedron*, 33:2725, 1977.

Wilen, S.H., Tables of Resolving Agents and Optical Resolutions, p. 268 (E.L. Eliel, ed., Univ. of Notre Dame Press, Notre Dame, IN, 1972).

TETRACYCLIC INDOLES AS POTASSIUM CHANNEL MODULATORS

This application claims the benefit of priority of U.S. Provisional Application No. 60/820,512, filed Jul. 27, 2006, which is hereby incorporated by reference in its entirety.

FIELD OF THE INVENTION

The present invention is directed to compounds of Formula I that are potassium channel modulators, pharmaceutical compositions thereof, and methods of using the same. The present invention is further directed to synthetic processes for producing the compounds of the invention.

BACKGROUND OF THE INVENTION

Transmembrane currents play a fundamental role in the activation and functioning of excitable tissues. In urinary bladder smooth muscle, depolarization, excitation-contraction, and repolarization are dependent upon the activation of transmembrane currents through voltage dependent ion channels. The current underlying repolarization in detrusor smooth muscle is carried through several ion channels, virtually all of which utilize potassium as the charge carrier. Several of these channels have been the target of compounds and drugs aimed at modulating the physiology and functioning of smooth muscle and other tissues [Edwards, G & Weston, A H, "Pharmacology of the potassium channel openers", *Cardiovasc Drugs Ther* 9 (Suppl. 2): 185-193 (1995), which is incorporated herein by reference in its entirety].

It has been suggested that a potassium channel opener (KCO) may be useful in the treatment of detrusor hyperactivity [Foster D C & Brading A F, "The effect of potassium channel antagonists on the BRL 34915 activated potassium channel in guinea-pig bladder", *Br J Pharmacol* 92: 751 (1987), which is incorporated herein by reference of in its entirety]. An increase in potassium channel permeability would hyperpolarize the cell, bring the membrane potential further from the threshold for activation of calcium channels and reduce excitability [Brading A F, "Ion channels and control of contractile activity in urinary bladder smooth muscle", *JPN J Pharmacol* 58 (Suppl 2): 120P-127P (1992), which is incorporated herein by reference in its entirety]. A number of potassium channel openers have shown activity in isolated tissues [Malmgren A, et al., "Effects of cromakalim (BRL 34915) and pinacidil on normal and hypertrophied rat detrusor in vitro", *J Urol* 143: 828-834 (1990); Grant T L & Zuzack J S., "Effects of K$^+$ channel blockers and cromakalim (BRL 34915) on the mechanical activity of guinea pig detrusor smooth muscle", *J Pharmacol Exp Ther* 269(3): 1158-1164 (1991), each of which is incorporated herein by reference in its entirety] and efficacy in both experimental and clinical bladder instability [Foster & Brading, supra, *Br J Pharmacol* 92: 751 (1987); Malmgren A, et al., "Effects of pinacidil and cromakalim (BRL 34915) on bladder function in rats with detrusor instability", *J Urol* 142: 1134-1138 (1989); Wojdan A, et al., "Comparison of the potassium channel openers ZD6169, celikalim and WAY-133537 on isolated bladder tissue and in vivo bladder instability in the rat", *J Pharmacol Exp Ther* 289(3): 1410-1418 (1999), each of which is incorporated by reference in its entirety). However, because these compounds also activate channels in vascular smooth muscle, causing vasodilation, the clinical utility has been severely limited by hemodynamic side effects including hypotension and tachycardia.

It has been stated previously that retigabine (N-[2-amino-4-(4-fluorobenzylamino)-phenyl]carbamic acid ethyl ester) activates a member of the KCNQ family of potassium channel in the bladder which is most likely KCNQ2/3 and/or KCNQ3/5 [Wickenden A D, et al., "Retigabine, a novel anticonvulsant, enhances activation of KCNQ2/Q3 potassium channels", *Molec Pharmacol* 58: 591-600 (2000); Wickenden, A D, et al., "Characterization of the KCNQ5/Q3 potassium channels expressed in mammalian cells", *Br J Pharmacol* 132(2): 381-384 (2001); Rundfeldt, C & Netzer, R, "The novel anticonvulsant retigabine activates M-currents in Chinese hamster ovary-cells tranfected with human KCNQ2/3 subunits", *Neurosci Lett* 282(1-2): 73-76 (2000); Main, M J, et al., "Modulation of KCNQ2/3 potassium channels by the novel anticonvulsant retigabine", *Mol Pharmacol* 58(2): 253-262 (2000), each of which is incorporated herein by reference in its entirety]. The result is an inhibition of bladder smooth muscle contractility. In addition, recent data provides evidence for the existence of the KCNQ4 channel in human bladder smooth muscle. Current knowledge of KCNQ4 suggests that it may form a functional ion channel on its own [Sogaard, R, et al., "KCNQ4 channels expressed in mammalian cells: functional characteristics and pharmacology", *Am J Physiol Cell Physiol* 280(4): C859-C866 (2001), which is incorporated herein by reference in its entirety], or that it may combine with KCNQ3 [Kubisch C, et al., "KCNQ4, a novel potassium channel expressed in sensory outer hair cells, is mutated in dominant deafness", *Cell* 96(3):437-446 (1999), which is incorporated herein by reference in its entirety]. It is likely therefore, that retigabine's effects on bladder smooth muscle include activation of the KCNQ4 channel in addition to the channels formed by KCNQ2/3 and KCNQ3/5. Activation of this channel will hyperpolarize the bladder smooth muscle cells and, in doing so, relax the bladder. Since these KCNQ channels are not present in the cardiovascular system, retigabine and other molecules that activate these channels should be useful in the treatment of bladder instability without hemodynamic compromise.

M-currents have been shown to play an important functional role as determinants of cell excitability. Recent evidence indicates that the KCNQ potassium channel subunit form the molecular basis for M-current activity in a variety of tissues. From their initial report in peripheral sympathetic neurons the gene family has evolved to contain at least five major sub-units designated KCNQ1 though KCNQ5 [Rogowski, M A, "KCNQ2/KCNQ3 K$^+$ channels and the molecular pathogenesis of epilepsy: implications for therapy", *Trends Neurosci* 23: 393-398, (2000); Jentsch, T J, "Neuronal KCNQ potassium channels: physiology and role in disease", *Nat Rev Neurosci* 1(1):21-30 (2000), each of which is incorporated herein by reference in its entirety]. These sub-units have been shown to co-assemble to form both heteromeric and homomeric functional ion channels. Recent reports indicate that both KCNQ2 and KCNQ5 can co-assemble with KCNQ3 [Tinel, N, et al., "The KCNQ2 potassium channel: splice variants, functional and developmental expression. Brain localization and comparison with KCNQ3", *FEBS Lett* 438(3): 171-176 (1998); Yang, W P, et al., "Functional expression of two KvLQT1-related potassium channels responsible for an inherited idiopathic epilepsy", *J Biol Chem* 273(31):19419-19423 (1998); Wang, H S, et al., "KCNQ2 and KCNQ3 potassium channel subunits: molecular correlets of the M-channel", *Science* 282(5395): 1890-1893 (1998); Lerche, C, et al., "Molecular cloning and functional expression of KCNQ5, a potassium channel subunit that may contribute to neuronal M-current diversity", *J Biol Chem* 275(29): 22395-22400 (2000); Schroeder, B C, et al., "KCNQ5, a novel potassium channel broadly expressed in brain, mediates M-type currents," *J Biol Chem* 275(31): 24089-24095 (2000), each of which is incorporated herein by reference in its entirety] to form a functional M-channel activatable by retigabine [Wickenden, supra, *Molec Pharmacol* 58: 591-600 (2000); Wickenden, supra, *Br J Pharmacol* 132 (2): 381-384 (2001); Rundfeldt & Netzer, supra, *Neurosci*

Lett 282(1-2): 73-76 (2000); Main, supra, *Mol Pharmacol* 58(2): 253-262 (2000)] and blocked by either acetylcholine [Adams, P R, et al., "M-currents and other potassium currents in bullfrog sympathetic neurones", *J Physiol* 330: 537-72 (1982); Brown, D A & Adams, P R "Muscarinic suppression of a novel voltage-sensitive K+ current in a vertebrate neurone", *Nature* 283: 673-676 (1980); Shapiro, M S, et al., "Reconstitution of muscarinic modulation of the KCNQ2/KCNQ3 K(+) channels that underlie the neuronal M current", *J Neurosci* 20(5): 1710-1721 (2000), each of which is incorporated herein by reference in its entirety], linopirdine, or XE-991 (10,10-bis(4-pyridinylmethyl)-9(10H)-anthra-cenone) [Aiken, S P, et al., "Reduction of spike frequency adaptation and blockade of M-current in rat CA1 pyramidal neurons by linopirdine (DuP 996) a neurotransmitter release enhancer", *Br J Pharmacol* 115(7): 1163-1168, (1995); Zaczek R, "Two new potent neurotransmitter release enhancers, 10,10-bis(4-pyridinylmethyl)-9(10H)-anthracenone and 10,10-bis(2-fluoro-4-pyridinylmethyl)-9(10H)-anthracenone: comparison to linopirdine", *J Pharmacol Exp Ther* 285(2): 724-730 (1998), each of which is incorporated herein by reference in its entirety]. The parasympathetic neurotransmitter acetylcholine (Ach) is known to produce several physiological responses in bladder smooth muscle. The net result of Ach exposure is a contraction of the smooth muscle mainly through the mobilization of transmembrane and intracellular calcium stores [Hashitani H, et al., "Mechanisms of excitatory neuromuscular transmission in the guinea-pig urinary bladder", *J Physiol* 524(Part 2): 565-579 (2000), which is incorporated herein by reference in its entirety]. The role that Ach plays in modulating the cell transmembrane potential, however, is more complex. Pathways for both hyperpolarization and depolarization are present with muscarinic stimulation of bladder smooth muscle. Hyperpolarization may be associated with a mechanism that involves calcium sparks and activation of calcium-dependent potassium currents [Herrera G M, et al., "Voltage dependence of the coupling of Ca(2+) sparks to BK(Ca) channels in urinary bladder smooth muscle", *Am J Physiol Cell Physiol* 280(3): C481-490 (2001), which is incorporated herein by reference in its entirety].

Given their potential in the treatment of urinary incontinence and other disorders, there is an interest in developing new potassium channel modulators. This invention addresses these needs and others.

SUMMARY OF THE INVENTION

In one aspect, the present invention provides compounds of Formula I:

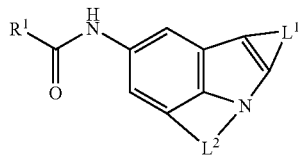

I or pharmaceutically acceptable salts thereof; wherein:

$R^1$ is H, amino, $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, —OR², —SR², or —NR³R⁴; wherein said $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^q$-$C(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups;

$L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups;

each $R^2$, $R^3$, and $R^4$ is, independently, H, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^8$ groups;

each $R^5$ or $R^8$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$ $NR^cC(=NR^a)OR^d$, $NR^cC(=NR^a)NR^d$, halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups;

each $R^9$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $NR^{c'}C(O)R^{d'}$, $NR^{c'}C(O)OR^{d'}$, $NR^{c'}C(O)NR^{d'}$, $S(O)R^{b'}$, $S(O)NR^{e'}R^{f'}$, $S(O)_2R^{b'}$, $NR^{c'}S(O)_2R^{d'}$, $NR^{b'}S(O)_2NR^{e'}R^{f'}$, halogen, cyano, nitro, hydroxyl, carboxy, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^6$ is, independently, $OR^{o'}$, $SR^{o'}$, $C(O)R^{p'}$, $C(O)NR^{s'}R^{t'}$, $C(O)OR^{p'}$, $OC(O)R^{p'}$, $OC(O)NR^{s'}R^{t'}$, $NR^{s'}R^{t'}$, $NR^{q'}C(O)R^{r'}$, $NR^{q'}C(O)OR^{r'}$, $NR^{q'}C(O)NR^{r'}$, $S(O)R^{p'}$, $S(O)NR^{s'}R^{t'}$, $S(O)_2R^{p'}$, $NR^{q'}S(O)_2R^{r'}$, $NR^{p'}S(O)_2NR^{s'}R^{t'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^7$ is, independently, $OR^{u'}$, $SR^{u'}$, $C(O)R^{v'}$, $C(O)NR^{y'}R^{z'}$, $C(O)OR^{v'}$, $OC(O)R^{v'}$, $OC(O)NR^{y'}R^{z'}$, $NR^{y'}R^{z'}$, $NR^{w'}C(O)R^{x'}$, $NR^{w'}C(O)OR^{x'}$, $NR^{w'}C(O)NR^{x'}$, $S(O)R^{v'}$, $S(O)NR^{y'}R^{z'}$, $S(O)_2R^{v'}$, $NR^{w'}S(O)_2R^{x'}$, $NR^{v'}S(O)_2NR^{y'}R^{z'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^a$, $R^b$, $R^c$, $R^d$, $R^e$, or $R^f$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 $R^g$ groups;

or any $R^c$ and $R^d$, together with the moiety to which they are attached, form a 3-, 4-, 5-, 6- 7- or 8-membered heterocycloalkyl ring, wherein said heterocycloalkyl ring is optionally substituted with 1, 2, or 3 $R^{g'}$ groups;

or any $R^e$ and $R^f$, together with the nitrogen atom to which they are attached, form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 $R^{g'''}$ groups;

each $R^g$, $R^{g'}$, or $R^{g'''}$ is, independently, halogen, cyano, nitro, hydroxyl, $C_{1-6}$ alkyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^{a'}$, $R^{b'}$, $R^{c'}$, $R^{d'}$, $R^{e'}$, or $R^{f'}$ is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{c'}$ and $R^{d'}$, together with the moiety to which they are attached, form a 3-, 4-, 5-, 6- 7- or 8-membered heterocycloalkyl ring;

or any $R^{e'}$ and $R^{f'}$, together with the nitrogen atom to which they are attached, form a 3-, 4-, 5-, 6- 7- or 8-membered heterocycloalkyl ring or 5-, 6-, 7- or 8-membered heteroaryl ring;

each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, $C_{1-6}$ alkyl, $C_{1-6}$ haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any $R^q$ and $R^r$, together with the moiety to which they are attached, form a 3-, 4-, 5-, 6- 7- or 8-membered heterocycloalkyl ring;

or any $R^s$ and $R^t$, together with the nitrogen atom to which they are attached, form a 3-, 4-, 5-, 6- 7- or 8-membered heterocycloalkyl ring or 5-, 6-, 7- or 8-membered heteroaryl ring;

or any $R^w$ and $R^x$, together with the moiety to which they are attached, form a 3-, 4-, 5-, 6- 7- or 8-membered heterocycloalkyl ring;

or any $R^y$ and $R^z$, together with the nitrogen atom to which they are attached, form a 3-, 4-, 5-, 6- 7- or 8-membered heterocycloalkyl ring or 5-, 6-, 7- or 8-membered heteroaryl ring; and each $R^{o'}$, $R^{p'}$, $R^{q'}$, $R^{r'}$, $R^{s'}$, $R^{t'}$, $R^{u'}$, $R^{v'}$, $R^{w'}$, $R^{y'}$, or $R^{z'}$, is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{q'}$ and $R^{r'}$, together with the moiety to which they are attached, form a 3-, 4-, 5-, 6- 7- or 8-membered heterocyclic ring;

or any $R^{s'}$ and $R^{t'}$, together with the nitrogen atom to which they are attached, form a 3-, 4-, 5-, 6- 7- or 8-membered heterocycloalkyl ring or 5-, 6-, 7- or 8-membered heteroaryl ring;

or any $R^{w'}$ and $R^{x'}$, together with the moiety to which they are attached, form a 3-, 4-, 5-, 6- 7- or 8-membered heterocycloalkyl ring;

or any $R^{y'}$ and $R^{z'}$, together with the nitrogen atom to which they are attached, form a 3-, 4-, 5-, 6- 7- or 8-membered heterocycloalkyl ring or 5-, 6-, 7- or 8-membered heteroaryl ring;

provided that the compound is not N-(4-oxo-5,6,8,9,10,11-hexahydro-4H-pyrido[3,2,1-jk]carbazol-2-yl)-acetamide, or pharmaceutically acceptable salt thereof.

In another aspect, the present invention provides pharmaceutical compositions which comprises a compound of Formula I, or a pharmaceutically salt thereof, and a pharmaceutically acceptable carrier.

In yet another aspect, the present invention provides methods of treating ischemic heart disease, myocardial infarction, cardiac arrhythmia, hypertension, or angina pectoris in an individual in need thereof, comprising administering to said individual a therapeutically effective amount of a compound of Formula I.

The present invention further provides methods of treating epilepsy, episodic ataxia type 1, paroxysmal dyskinesia, neurodegenerative spincerebrallar ataxia, Parkinson's disease, Alzheimer's disease, or multiple sclerosis in an individual in need of treatment thereof, comprising administering to said individual a therapeutically effective amount of a compound of Formula I.

The present invention further provides methods of treating depression, generalized anxiety disorder, bulimia nervosa, or anorexia nervosa in an individual in need thereof, comprising administering to said individual a therapeutically effective amount of a compound of Formula I.

The present invention further provides methods of treating type I diabetes or type II diabetes in an individual in need thereof, comprising administering to said individual a therapeutically effective amount of a compound of Formula I.

The present invention further provides methods of treating allergy or asthma in an individual in need thereof, comprising administering to said individual a therapeutically effective amount of a compound of Formula I.

The present invention further provides methods of treating urinary incontinence, irritable bowel syndrome, or irritable bladder syndrome in an individual in need thereof, comprising administering to said individual a therapeutically effective amount of a compound of Formula I.

The present invention further provides methods of treating pain or inflammation in an individual in need thereof, comprising administering to said individual a therapeutically effective amount of a compound of Formula I.

The present invention further provides methods of modulating a potassium channel in an individual in need thereof, comprising administering to said individual a therapeutically effective amount of a compound of Formula I.

In another aspect, the present invention further provides uses of a compound of Formula I, or pharmaceutically acceptable salt thereof, for the production of medicament for use in the treatment of disorders remedied or alleviated by potassium channel modulation.

The present invention further provides uses of a compound of Formula I, or pharmaceutically acceptable salt thereof, for the production of medicament for use in the treatment of ischemic heart disease, myocardial infarction, cardiac arrhythmia, hypertension, or angina pectoris.

The present invention further provides uses of a compound of Formula I, or pharmaceutically acceptable salt thereof, for the production of medicament for use in the treatment of epilepsy, episodic ataxia type 1, paroxysmal dyskinesia, neurodegenerative spincerebrallar ataxia, Parkinson's disease, Alzheimer's disease, or multiple sclerosis.

The present invention further provides uses of a compound of Formula I, or pharmaceutically acceptable salt thereof, for the production of medicament for use in the treatment of depression, generalized anxiety disorder, bulimia nervosa, or anorexia nervosa, The present invention further provides uses of a compound of Formula I, or pharmaceutically acceptable salt thereof, for the production of medicament for use in the treatment of type I diabetes or type II diabetes.

The present invention further provides uses of a compound of Formula I, or pharmaceutically acceptable salt thereof, for the production of medicament for use in the treatment of allergy or asthma.

The present invention further provides uses of a compound of Formula I, or pharmaceutically acceptable salt thereof, for the production of medicament for use in the treatment of urinary incontinence, irritable bowel syndrome, or irritable bladder syndrome.

The present invention further provides uses of a compound of Formula I, or pharmaceutically acceptable salt thereof, for the production of medicament for use in the treatment of pain or inflammation.

In another aspect, the present invention provides compounds of Formula I, or pharmaceutically acceptable salts thereof, for use in a method of treatment of disorders remedied or alleviated by potassium channel modulation.

The present invention further provides compounds of Formula I, or pharmaceutically acceptable salts thereof, for use in a method of treatment of ischemic heart disease, myocardial infarction, cardiac arrhythmia, hypertension, or angina pectoris by therapy.

The present invention further provides compounds of Formula I, or pharmaceutically acceptable salts thereof, for use in a method of treatment of epilepsy, episodic ataxia type 1, paroxysmal dyskinesia, neurodegenerative spincerebrallar ataxia, Parkinson's disease, Alzheimer's disease, or multiple sclerosis by therapy.

The present invention further provides compounds of Formula I, or pharmaceutically acceptable salts thereof, for use in a method of treatment of depression, generalized anxiety disorder, bulimia nervosa, or anorexia nervosa by therapy.

The present invention further provides compounds of Formula I, or pharmaceutically acceptable salts thereof, for use in a method of treatment of type I diabetes or type II diabetes by therapy.

The present invention further provides compounds of Formula I, or pharmaceutically acceptable salts thereof, for use in a method of treatment of allergy or asthma by therapy.

The present invention further provides compounds of Formula I, or pharmaceutically acceptable salts thereof, for use in a method of treatment of urinary incontinence, irritable bowel syndrome, or irritable bladder syndrome by therapy.

The present invention further provides compounds of Formula I, or pharmaceutically acceptable salts thereof, for use in a method of treatment of pain or inflammation by therapy.

In another aspect, the present invention provides synthetic processes for producing a compound of Formula I, comprising reacting a compound of Formula VIII:

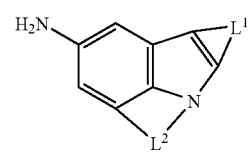

VIII with a compound of Formula IX:

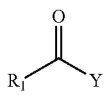

under conditions and for a time sufficient to produce a compound of Formula I:

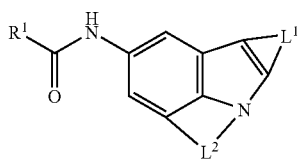

wherein:
R$^1$ is H, amino, C$_{1-12}$ alkyl, C$_{2-12}$ alkenyl, C$_{2-12}$ alkynyl, C$_{1-12}$ haloalkyl, C$_{1-12}$ haloalkoxy, C$_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, —OR$^2$, —SR$^2$, or —NR$^3$R$^4$; wherein said C$_{1-12}$ alkyl, C$_{2-12}$ alkenyl, C$_{2-12}$ alkynyl, C$_{1-12}$ haloalkyl, C$_{1-12}$ haloalkoxy, C$_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 R$^5$ groups;

L$^1$ is a C$_{3-6}$alkylene bridge which is optionally substituted with 1, 2, 3, or 4 groups independently selected from OR$^o$, SR$^o$, C(O)R$^p$, C(O)NR$^s$R$^t$, C(O)OR$^p$, OC(O)R$^p$, OC(O)NR$^s$R$^t$, NR$^s$R$^t$, NR$^q$C(O)R$^r$, NR$^q$C(O)OR$^r$, NR$^q$C(O)NR$^r$, S(O)R$^p$, S(O)NR$^s$R$^t$, S(O)$_2$R$^p$, NR$^q$S(O)$_2$R$^r$, NR$^p$S(O)$_2$NR$^s$R$^t$, oxo, halogen, cyano, nitro, hydroxyl, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 R$^6$ groups;

L$^2$ is a C$_{2-5}$ alkylene bridge which is optionally substituted with 1, 2, 3, or 4 groups independently selected from OR$^u$, SR$^u$, C(O)R$^v$, C(O)NR$^y$R$^z$, C(O)OR$^v$, OC(O)R$^v$, OC(O)NR$^y$R$^z$, NR$^y$R$^z$, NR$^w$C(O)R$^x$, NR$^w$C(O)OR$^x$, NR$^w$C(O)NR$^x$, S(O)R$^v$, S(O)NR$^y$R$^z$, S(O)$_2$R$^v$, NR$^w$S(O)$_2$R$^x$, NR$^v$S(O)$_2$NR$^y$R$^z$, oxo, halogen, cyano, nitro, hydroxyl, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl; wherein said C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 R$^7$ groups;

each R$^2$, R$^3$, and R$^4$ is, independently, H, C$_{1-6}$ alkyl, C$_{1-6}$ alkenyl, C$_{1-6}$ alkynyl, C$_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ alkenyl, C$_{1-6}$ alkynyl, C$_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 R$^8$ groups;

each R$^5$ or R$^8$ is, independently, OR$^a$, SR$^a$, C(O)R$^b$, C(O)NR$^e$R$^f$, C(O)OR$^b$, OC(O)R$^b$, OC(O)NR$^e$R$^f$, NR$^e$R$^f$, NR$^c$C(O)R$^d$, NR$^c$C(O)OR$^d$, NR$^c$C(O)NR$^d$ S(O)R$^b$, S(O)NR$^e$R$^f$, S(O)$_2$R$^b$, NR$^c$S(O)$_2$R$^d$, NR$^b$S(O)$_2$NR$^e$R$^f$, C(=NR$^a$)R$^b$, C(=NR$^a$)NR$^b$, C(=NR$^a$)OR$^b$, OC(=NR$^a$)R$^b$, OC(=NR$^a$)NR$^b$, NR$^c$C(=NR$^a$)R$^d$ NR$^c$C(=NR$^a$)OR$^d$, NR$^c$C(=NR$^a$)NR$^d$, halogen, cyano, nitro, hydroxyl, carboxy, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 R$^9$ groups;

each R$^9$ is, independently, OR$^{a'}$, SR$^{a'}$, C(O)R$^{b'}$, C(O)NR$^{e'}$R$^{f'}$, C(O)OR$^{b'}$, OC(O)R$^{b'}$, OC(O)NR$^{e'}$R$^{f'}$, NR$^{e'}$R$^{f'}$, NR$^{c'}$C(O)R$^{d'}$, NR$^{c'}$C(O)OR$^{d'}$, NR$^{c'}$C(O)NR$^{d'}$, S(O)R$^{b'}$, S(O)NR$^{e'}$R$^{f'}$, S(O)$_2$R$^{b'}$, NR$^{c'}$S(O)$_2$R$^{d'}$, NR$^{b'}$S(O)$_2$NR$^{e'}$R$^{f'}$, halogen, cyano, nitro, hydroxyl, carboxy, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each R$^6$ is, independently, OR$^{o'}$, SR$^{o'}$, C(O)R$^{p'}$, C(O)NR$^{s'}$R$^{t'}$, C(O)OR$^{p'}$, OC(O)R$^{p'}$, OC(O)NR$^{s'}$R$^{t'}$, NR$^{s'}$R$^{t'}$, NR$^{q'}$C(O)R$^{r'}$, NR$^{q'}$C(O)OR$^{r'}$, NR$^{q'}$C(O)NR$^{r'}$, S(O)R$^{p'}$, S(O)NR$^{s'}$R$^{t'}$, S(O)$_2$R$^{p'}$, NR$^{q'}$S(O)$_2$R$^{r'}$, NR$^{p'}$S(O)$_2$NR$^{s'}$R$^{t'}$, halogen, cyano, nitro, hydroxyl, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, or heteroarylalkyl;

each R$^7$ is, independently, OR$^{u'}$, SR$^{u'}$, C(O)R$^{v'}$, C(O)NR$^{y'}$R$^{z'}$, C(O)OR$^{v'}$, OC(O)R$^{v'}$, OC(O)NR$^{y'}$R$^{z'}$, NR$^{y'}$R$^{z'}$, NR$^{w'}$C(O)R$^{x'}$, NR$^{w'}$C(O)OR$^{x'}$, NR$^{w'}$C(O)NR$^{x'}$, S(O)R$^{v'}$, S(O)NR$^{y'}$R$^{z'}$, S(O)$_2$R$^{v'}$, NR$^{w'}$S(O)$_2$R$^{x'}$, NR$^{v'}$S(O)$_2$NR$^{y'}$R$^{z'}$, halogen, cyano, nitro, hydroxyl, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, or heteroarylalkyl;

each R$^a$, R$^b$, R$^c$, R$^d$, R$^e$, or R$^f$ is, independently, H, C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 R$^g$ groups;

or any R$^c$ and R$^d$, together with the moiety to which they are attached, form a 3-, 4-, 5-, 6- 7- or 8-membered heterocycloalkyl ring, wherein said heterocycloalkyl ring is optionally substituted with 1, 2, or 3 R$^{g'}$ groups;

or any R$^e$ and R$^f$, together with the nitrogen atom to which they are attached, form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 R$^{g'''}$ groups;

each R$^g$, R$^{g'}$, or R$^{g'''}$ is, independently, halogen, cyano, nitro, hydroxyl, C$_{1-6}$ alkyl, C$_{1-6}$ haloalkyl, C$_{1-6}$ alkoxy, C$_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each R$^{a'}$, R$^{b'}$, R$^{c'}$, R$^{d'}$, R$^{e'}$, or R$^{f'}$ is, independently, H, C$_{1-6}$ alkyl, C$_{1-6}$ haloalkyl, cycloalkyl, cycloalkylalkyl, heterocycloalkyl, heterocycloalkylalkyl, aryl, arylalkyl, heteroaryl, or heteroarylalkyl;

or any R$^{c'}$ and R$^{d'}$, together with the moiety to which they are attached, form a 3-, 4-, 5-, 6- 7- or 8-membered heterocycloalkyl ring;

or any R$^{e'}$ and R$^{f'}$, together with the nitrogen atom to which they are attached, form a 3-, 4-, 5-, 6- 7- or 8-membered heterocycloalkyl ring or 5-, 6-, 7- or 8-membered heteroaryl ring;

each R$^o$, R$^p$, R$^q$, R$^r$, R$^s$, R$^t$, R$^u$, R$^v$, R$^w$, R$^y$, or R$^z$, is, independently, H, C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, C$_{1-6}$ alkyl, C$_{1-6}$ haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any R$^q$ and R$^r$, together with the moiety to which they are attached, form a 3-, 4-, 5-, 6- 7- or 8-membered heterocycloalkyl ring;

or any R$^s$ and R$^t$, together with the nitrogen atom to which they are attached, form a 3-, 4-, 5-, 6- 7- or 8-membered heterocycloalkyl ring or 5-, 6-, 7- or 8-membered heteroaryl ring;

or any R$^w$ and R$^x$, together with the moiety to which they are attached, form a 3-, 4-, 5-, 6- 7- or 8-membered heterocycloalkyl ring;

or any R$^y$ and R$^z$, together with the nitrogen atom to which they are attached, form a 3-, 4-, 5-, 6- 7- or 8-membered heterocycloalkyl ring or 5-, 6-, 7- or 8-membered heteroaryl ring;

each R$^{o'}$, R$^{p'}$, R$^{q'}$, R$^{r'}$, R$^{s'}$, R$^{t'}$, R$^{u'}$, R$^{v'}$, R$^{w'}$, R$^{y'}$, or R$^{z'}$, is, independently, H, C$_{1-6}$ alkyl, C$_{1-6}$ haloalkyl, cycloalkyl, cycloalkylalkyl, heterocycloalkyl, heterocycloalkylalkyl, aryl, arylalkyl, heteroaryl, or heteroarylalkyl;

or any R$^{q'}$ and R$^{r'}$, together with the moiety to which they are attached, form a 3-, 4-, 5-, 6- 7- or 8-membered heterocyclic ring;

or any R$^{s'}$ and R$^{t'}$, together with the nitrogen atom to which they are attached, form a 3-, 4-, 5-, 6- 7- or 8-membered heterocycloalkyl ring or 5-, 6-, 7- or 8-membered heteroaryl ring;

or any R$^{w'}$ and R$^{x'}$, together with the moiety to which they are attached, form a 3-, 4-, 5-, 6- 7- or 8-membered heterocycloalkyl ring;

or any R$^{y'}$ and R$^{z'}$, together with the nitrogen atom to which they are attached, form a 3-, 4-, 5-, 6- 7- or 8-membered heterocycloalkyl ring or 5-, 6-, 7- or 8-membered heteroaryl ring;

Y is halogen, C$_{1-12}$ alkoxy, hydroxyl, amino, OC(O)R$^{yy}$, or OC(O)R$_1$; and R$^{yy}$ is C$_{1-12}$ alkyl;

provided that the compound of Formula I is not N-(4-oxo-5,6,8,9,10,11-hexahydro-4H-pyrido[3,2,1-jk]carbazol-2-yl)-acetamide, or pharmaceutically acceptable salt thereof.

The present invention further provides synthetic processes for producing a compound of Formula VIII that comprise:

(a) reacting a compound of Formula IV:

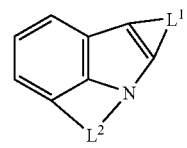

IV with a nitrating agent under conditions and for a time sufficient to produce a compound of Formula VII: and

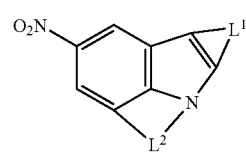

VII (b) reducing the nitro group of the compound of Formula VII under conditions and for a time sufficient to produce a compound of Formula VIII.

The present invention further provides synthetic processes for producing a compound of Formula IV that comprise reacting a compound of Formula II:

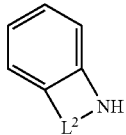

with a compound of Formula III:

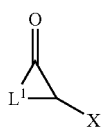

under conditions and for a time sufficient to form a compound of Formula IV; wherein X is halogen.

The present invention further provides synthetic processes for producing a compound of Formula IV that comprise reacting a compound of Formula V:

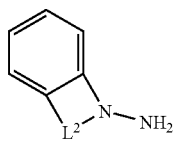

with a compound of Formula VI:

in the presence of a Fischer indole catalyst under conditions and for a time sufficient to form said compound of Formula IV.

In another aspect, the present invention provides synthetic process comprising reacting a compound of Formula XV:

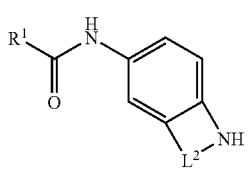

with a compound of Formula III:

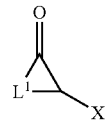

under conditions and for a time sufficient to produce a compound of Formula I:

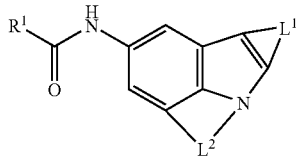

wherein:

$R^1$ is H, amino, $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, —$OR^2$, —$SR^2$, or —$NR^3R^4$; wherein said $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^q$-$C(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups;

$L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups;

each $R^2$, $R^3$, and $R^4$ is, independently, H, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^8$ groups;

each $R^5$ or $R^8$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$ $NR^cC(=NR^a)OR^d$, $NR^cC(=NR^a)NR^d$, halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups;

each $R^9$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $NR^{c'}C(O)R^{d'}$, $NR^{c'}C(O)OR^{d'}$, $NR^{c'}C(O)NR^{d'}$, $S(O)R^{b'}$, $S(O)NR^{e'}R^{f'}$, $S(O)_2R^{b'}$, $NR^{c'}S(O)_2R^{d'}$, $NR^{b'}S(O)_2NR^{e'}R^{f'}$, halogen, cyano, nitro, hydroxyl, carboxy, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^6$ is, independently, $OR^{o'}$, $SR^{o'}$, $C(O)R^{p'}$, $C(O)NR^{s'}R^{t'}$, $C(O)OR^{p'}$, $OC(O)R^{p'}$, $OC(O)NR^{s'}R^{t'}$, $NR^{s'}R^{t'}$, $NR^{q'}C(O)R^{r'}$, $NR^{q'}C(O)OR^{r'}$, $NR^{q'}C(O)NR^{r'}$, $S(O)R^{p'}$, $S(O)NR^{s'}R^{t'}$, $S(O)_2R^{p'}$, $NR^{q'}S(O)_2R^{r'}$, $NR^{p'}S(O)_2NR^{s'}R^{t'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^7$ is, independently, $OR^{u'}$, $SR^{u'}$, $C(O)R^{v'}$, $C(O)NR^{y'}R^{z'}$, $C(O)OR^{v'}$, $OC(O)R^{v'}$, $OC(O)NR^{y'}R^{z'}$, $NR^{y'}R^{z'}$, $NR^{w'}C(O)R^{x'}$, $NR^{w'}C(O)OR^{x'}$, $NR^{w'}C(O)NR^{x'}$, $S(O)R^{v'}$, $S(O)NR^{y'}R^{z'}$, $S(O)_2R^{v'}$, $NR^{w'}S(O)_2R^{x'}$, $NR^{v'}S(O)_2NR^{y'}R^{z'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^a$, $R^b$, $R^c$, $R^d$, $R^e$, or $R^f$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 $R^g$ groups;

or any $R^c$ and $R^d$, together with the moiety to which they are attached, form a 3-, 4-, 5-, 6- 7- or 8-membered heterocycloalkyl ring, wherein said heterocycloalkyl ring is optionally substituted with 1, 2, or 3 $R^{g'}$ groups;

or any $R^e$ and $R^f$, together with the nitrogen atom to which they are attached, form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 $R^{g'''}$ groups;

each $R^g$, $R^{g'}$, or $R^{g'''}$ is, independently, halogen, cyano, nitro, hydroxyl, $C_{1-6}$ alkyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^{a'}$, $R^{b'}$, $R^{c'}$, $R^{d'}$, $R^{e'}$, or $R^{f'}$ is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{c'}$ and $R^{d'}$, together with the moiety to which they are attached, form a 3-, 4-, 5-, 6- 7- or 8-membered heterocycloalkyl ring;

or any $R^{e'}$ and $R^{f'}$, together with the nitrogen atom to which they are attached, form a 3-, 4-, 5-, 6- 7- or 8-membered heterocycloalkyl ring or 5-, 6-, 7- or 8-membered heteroaryl ring;

each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, $C_{1-6}$ alkyl, $C_{1-6}$ haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any $R^q$ and $R^r$, together with the moiety to which they are attached, form a 3-, 4-, 5-, 6- 7- or 8-membered heterocycloalkyl ring;

or any $R^s$ and $R^t$, together with the nitrogen atom to which they are attached, form a 3-, 4-, 5-, 6- 7- or 8-membered heterocycloalkyl ring or 5-, 6-, 7- or 8-membered heteroaryl ring;

or any $R^w$ and $R^x$, together with the moiety to which they are attached, form a 3-, 4-, 5-, 6- 7- or 8-membered heterocycloalkyl ring;

or any $R^y$ and $R^z$, together with the nitrogen atom to which they are attached, form a 3-, 4-, 5-, 6- 7- or 8-membered heterocycloalkyl ring or 5-, 6-, 7- or 8-membered heteroaryl ring; and each $R^{o'}$, $R^{p'}$, $R^{q'}$, $R^{r'}$, $R^{s'}$, $R^{t'}$, $R^{u'}$, $R^{v'}$, $R^{w'}$, $R^{y'}$, or $R^{z'}$, is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{q'}$ and $R^{r'}$, together with the moiety to which they are attached, form a 3-, 4-, 5-, 6- 7- or 8-membered heterocyclic ring;

or any $R^{s'}$ and $R^{t'}$, together with the nitrogen atom to which they are attached, form a 3-, 4-, 5-, 6- 7- or 8-membered heterocycloalkyl ring or 5-, 6-, 7- or 8-membered heteroaryl ring;

or any $R^{w'}$ and $R^{x'}$, together with the moiety to which they are attached, form a 3-, 4-, 5-, 6- 7- or 8-membered heterocycloalkyl ring;

or any $R^{y'}$ and $R^{z'}$, together with the nitrogen atom to which they are attached, form a 3-, 4-, 5-, 6- 7- or 8-membered heterocycloalkyl ring or 5-, 6-, 7- or 8-membered heteroaryl ring;

X is halogen;

Y is halogen, $C_{1-12}$ alkoxy, hydroxyl, amino, $OC(O)R^{yy}$, or $OC(O)R_1$; and $R^{yy}$ is $C_{1-12}$ alkyl;

provided that the compound of Formula I is not N-(4-oxo-5,6,8,9,10,11-hexahydro-4H-pyrido[3,2,1-jk]carbazol-2-yl)-acetamide, or pharmaceutically acceptable salt thereof.

DETAILED DESCRIPTION OF THE INVENTION

The present invention provides a compound of Formula I:

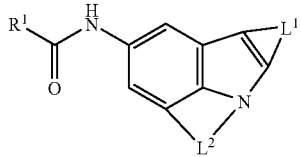

I or pharmaceutically acceptable salt thereof; wherein:

$R^1$ is H, amino, $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, —$OR^2$, —$SR^2$, or —$NR^3R^4$; wherein said $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups;

$L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^vS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups;

each $R^2$, $R^3$, and $R^4$ is, independently, H, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^8$ groups;

each $R^5$ or $R^8$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$, $NR^cC(=NR^a)OR^d$, $NR^cC(=NR^a)NR^d$, halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl are each optionally substituted by 1, 2, 3 or 4 $R^9$ groups;

each $R^9$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, NR$^{c'}$C(O)R$^{d'}$, NR$^{c'}$C(O)OR$^{d'}$, NR$^{c'}$C(O)NR$^{d'}$, S(O)R$^{b'}$, S(O)NR$^{e'}$R$^{f'}$, S(O)$_2$R$^{b'}$, NR$^{c'}$S(O)$_2$R$^{d'}$, NR$^{b'}$S(O)$_2$NR$^{e'}$R$^{f'}$, halogen, cyano, nitro, hydroxyl, carboxy, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each R$^6$ is, independently, OR$^{o'}$, SR$^{o'}$, C(O)R$^{p'}$, C(O)NR$^{s'}$R$^{t'}$, C(O)OR$^{p'}$, OC(O)R$^{p'}$, OC(O)NR$^{s'}$R$^{t'}$, NR$^{s'}$R$^{t'}$, NR$^{q'}$C(O)R$^{r'}$, NR$^{q'}$C(O)OR$^{r'}$, NR$^{q'}$C(O)NR$^{r'}$, S(O)R$^{p'}$, S(O)NR$^{s'}$R$^{t'}$, S(O)$_2$R$^{p'}$, NR$^{q'}$S(O)$_2$R$^{r'}$, NR$^{p'}$S(O)$_2$NR$^{s'}$R$^{t'}$, halogen, cyano, nitro, hydroxyl, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, or heteroarylalkyl;

each R$^7$ is, independently, OR$^{u'}$, SR$^{u'}$, C(O)R$^{v'}$, C(O)NR$^{y'}$R$^{z'}$, C(O)OR$^{v'}$, OC(O)R$^{v'}$, OC(O)NR$^{y'}$R$^{z'}$, NR$^{y'}$R$^{z'}$, NR$^{w'}$C(O)R$^{x'}$, NR$^{w'}$C(O)OR$^{x'}$, NR$^{w'}$C(O)NR$^{x'}$, S(O)R$^{v'}$, S(O)NR$^{y'}$R$^{z'}$, S(O)$_2$R$^{v'}$, NR$^{w'}$S(O)$_2$R$^{x'}$, NR$^{v'}$S(O)$_2$NR$^{y'}$R$^{z'}$, halogen, cyano, nitro, hydroxyl, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, or heteroarylalkyl;

each R$^a$, R$^b$, R$^c$, R$^d$, R$^e$, or R$^f$ is, independently, H, C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 R$^g$ groups;

or any R$^c$ and R$^d$, together with the moiety to which they are attached, form a 3-, 4-, 5-, 6- 7- or 8-membered heterocycloalkyl ring, wherein said heterocycloalkyl ring is optionally substituted with 1, 2, or 3 R$^{g'}$ groups;

or any R$^e$ and R$^f$, together with the nitrogen atom to which they are attached, form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 R$^{g''}$ groups;

each R$^g$, R$^{g'}$, or R$^{g''}$ is, independently, halogen, cyano, nitro, hydroxyl, C$_{1-6}$ alkyl, C$_{1-6}$ haloalkyl, C$_{1-6}$ alkoxy, C$_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each R$^{a'}$, R$^{b'}$, R$^{c'}$, R$^{d'}$, R$^{e'}$, or R$^{f'}$ is, independently, H, C$_{1-6}$ alkyl, C$_{1-6}$ haloalkyl, cycloalkyl, cycloalkylalkyl, heterocycloalkyl, heterocycloalkylalkyl, aryl, arylalkyl, heteroaryl, or heteroarylalkyl;

or any R$^{c'}$ and R$^{d'}$, together with the moiety to which they are attached, form a 3-, 4-, 5-, 6- 7- or 8-membered heterocycloalkyl ring;

or any R$^{e'}$ and R$^{f'}$, together with the nitrogen atom to which they are attached, form a 3-, 4-, 5-, 6- 7- or 8-membered heterocycloalkyl ring or 5-, 6-, 7- or 8-membered heteroaryl ring;

each R$^o$, R$^p$, R$^q$, R$^r$, R$^s$, R$^t$, R$^u$, R$^v$, R$^w$, R$^y$, or R$^z$, is, independently, H, C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ haloalkyl, C$_{2-6}$ alkenyl, C$_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, C$_{1-6}$ alkyl, C$_{1-6}$ haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any R$^q$ and R$^r$, together with the moiety to which they are attached, form a 3-, 4-, 5-, 6- 7- or 8-membered heterocycloalkyl ring;

or any R$^s$ and R$^t$, together with the nitrogen atom to which they are attached, form a 3-, 4-, 5-, 6- 7- or 8-membered heterocycloalkyl ring or 5-, 6-, 7- or 8-membered heteroaryl ring;

or any R$^w$ and R$^x$, together with the moiety to which they are attached, form a 3-, 4-, 5-, 6- 7- or 8-membered heterocycloalkyl ring;

or any R$^y$ and R$^z$, together with the nitrogen atom to which they are attached, form a 3-, 4-, 5-, 6- 7- or 8-membered heterocycloalkyl ring or 5-, 6-, 7- or 8-membered heteroaryl ring; and each R$^{o'}$, R$^{p'}$, R$^{q'}$, R$^{r'}$, R$^{s'}$, R$^{t'}$, R$^{u'}$, R$^{v'}$, R$^{w'}$, R$^{y'}$, or R$^{z'}$, is, independently, H, C$_{1-6}$ alkyl, C$_{1-6}$ haloalkyl, cycloalkyl, cycloalkylalkyl, heterocycloalkyl, heterocycloalkylalkyl, aryl, arylalkyl, heteroaryl, or heteroarylalkyl;

or any R$^{q'}$ and R$^{r'}$, together with the moiety to which they are attached, form a 3-, 4-, 5-, 6- 7- or 8-membered heterocyclic ring;

or any R$^{s'}$ and R$^{t'}$, together with the nitrogen atom to which they are attached, form a 3-, 4-, 5-, 6- 7- or 8-membered heterocycloalkyl ring or 5-, 6-, 7- or 8-membered heteroaryl ring;

or any R$^{w'}$ and R$^{x'}$, together with the moiety to which they are attached, form a 3-, 4-, 5-, 6- 7- or 8-membered heterocycloalkyl ring;

or any R$^{y'}$ and R$^{z'}$, together with the nitrogen atom to which they are attached, form a 3-, 4-, 5-, 6- 7- or 8-membered heterocycloalkyl ring or 5-, 6-, 7- or 8-membered heteroaryl ring;

provided that the compound is not N-(4-oxo-5,6,8,9,10,11-hexahydro-4H-pyrido[3,2,1-jk]carbazol-2-yl)-acetamide, or pharmaceutically acceptable salt thereof.

In some embodiments, R$^1$ is H, C$_{1-12}$ alkyl, C$_{2-12}$ alkenyl, C$_{2-12}$ alkynyl, C$_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl, wherein said C$_{1-12}$ alkyl, C$_{2-12}$ alkenyl, C$_{2-12}$ alkynyl, C$_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 $R^5$ groups.

In some embodiments, $R^1$ is H, $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups.

In some embodiments, $R^1$ is $C_{1-12}$ alkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups.

In some embodiments, $R^1$ is $C_{1-12}$ alkyl, cycloalkyl, cycloalkylalkyl, heterocycloalkyl, heterocycloalkylalkyl, arylalkyl, or heteroaryl, wherein said $C_{1-12}$ alkyl, $C_{2-12}$ alkynyl, cycloalkyl, cycloalkylalkyl, heterocycloalkyl, heterocycloalkylalkyl, arylalkyl, and heteroaryl are each optionally substituted by 1, 2, 3, or 4 $R^5$ groups.

In some embodiments, $R^1$ is $C_{1-12}$ alkyl, cycloalkyl, cycloalkylalkyl, heterocycloalkyl, heterocycloalkylalkyl, arylalkyl, or heteroaryl.

In some embodiments, $R^1$ is methyl, ethyl, n-butyl, isobutyl, tert-butyl, neopentyl, n-pentyl, n-hexyl, cyclohexyl, cyclopentylethyl, benzyl, phenylethyl, or thiophen-2-yl.

In some embodiments, $L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups.

In some embodiments, $L^1$ is a $C_{4-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $NR^sR^t$, $NR^qC(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups.

In some embodiments, $L^1$ is a $C_{4-6}$ alkylene bridge which is optionally substituted with 1, 2, 3, or 4 groups independently selected from $OR^o$, $C(O)R^p$, $NR^sR^t$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups.

In some embodiments, $L^1$ is a $C_{4-6}$ alkylene bridge which is optionally substituted with 1, 2, 3, or 4 oxo groups.

In some embodiments, $L^1$ is a $C_{4-6}$ alkylene bridge which is optionally substituted with 1 oxo group.

In some embodiments, $L^1$ is an unsubstituted $C_{4-6}$ alkylene bridge.

In some embodiments, $L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^vS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups.

In some embodiments, $L^2$ is a $C_{2-3}$ alkylene bridge which is optionally substituted with 1, 2, 3, or 4 groups independently selected from $OR^u$, $SR^u$, $C(O)R^v$, $C(O)NR^yR^z$, $C(O)OR^v$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^vS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl are each optionally substituted by 1, 2, or 3 $R^7$ groups.

In some embodiments, $L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl, are each optionally substituted by 1, 2, or 3 $R^7$ groups.

In some embodiments, $L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl.

In some embodiments, $L^2$ is an unsubstituted $C_{2-3}$ alkylene bridge.

In some embodiments, each $R^2$, $R^3$, and $R^4$ is, independently, H, $C_{1-6}$alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl.

In some embodiments, $R^5$ or $R^8$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups.

In some embodiments, $R^5$ or $R^8$ is, independently, $OR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$ halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups.

In some embodiments, $R^5$ or $R^8$ is, independently, $OR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl.

In some embodiments, $R^5$ or $R^8$ is, independently, $OR^a$, $NR^eR^f$, halogen, cyano, nitro, hydroxyl, amino, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups.

In some embodiments, $R^5$ or $R^8$ is, independently, $OR^a$, $NR^eR^f$, halogen, cyano, nitro, hydroxyl, amino, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl.

In some embodiments, $R^5$ or $R^8$ is, independently, halogen, cyano, nitro, hydroxyl, $C_{1-6}$ alkyl, $C_{1-6}$ haloalkyl, or $C_{1-6}$ haloalkoxy; wherein said $C_{1-6}$ alkyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups.

In some embodiments, $R^5$ or $R^8$ is, independently, halogen, cyano, nitro, hydroxyl, $C_{1-6}$ alkyl, $C_{1-6}$ haloalkyl, or $C_{1-6}$ haloalkoxy.

In some embodiments, each $R^9$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $NR^{c'}C(O)R^{d'}$, $NR^{c'}C(O)OR^{d'}$, $NR^{c'}C(O)NR^{d'}$, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio.

In some embodiments, each $R^9$ is, independently, $OR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $C_{1-6}$ alkyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio.

In some embodiments, each $R^9$ is, independently, $C_{1-6}$ alkyl, $C_{1-6}$ haloalkyl, $C_{1-6}$ alkoxy, $C_{1-6}$ haloalkoxy, amino, alkylamino, and dialkylamino.

In some embodiments, each $R^6$ is, independently, $OR^{o'}$, $SR^{o'}$, $C(O)R^{p'}$, $C(O)NR^{s'}R^{t'}$, $C(O)OR^{p'}$, $OC(O)R^{p'}$, $OC(O)NR^{s'}R^{t'}$, $NR^{s'}R^{t'}$, $NR^{q'}C(O)R^{r'}$, $NR^{q'}C(O)OR^{r'}$, $NR^{q'}C(O)NR^{r'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl.

In some embodiments, each $R^6$ is, independently, $OR^{o'}$, $C(O)R^{p'}$, $C(O)NR^{s'}R^{t'}$, $C(O)OR^{p'}$, $OC(O)R^{p'}$, $OC(O)NR^{s'}R^{t'}$, $NR^{s'}R^{t'}$, halogen, cyano, nitro, hydroxyl, amino, $C_{1-6}$ alkyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl.

In some embodiments, each $R^6$ is, independently, halogen, cyano, nitro, hydroxyl, amino, $C_{1-6}$ alkyl, $C_{1-6}$ haloalkyl, $C_{1-6}$ alkoxy, or $C_{1-6}$ haloalkoxy.

In some embodiments, each $R^7$ is, independently, $OR^{u'}$, $SR^{u'}$, $C(O)R^{v'}$, $C(O)NR^{y'}R^{z'}$, $C(O)OR^{v'}$, $OC(O)R^{v'}$, $OC(O)NR^{y'}R^{z'}$, $NR^{y'}R^{z'}$, $NR^{w'}C(O)R^{x'}$, $NR^{w'}C(O)OR^{x'}$, $NR^{w'}C(O)NR^{x'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl.

In some embodiments, each $R^7$ is, independently, $OR^{u'}$, $C(O)R^{v'}$, $C(O)NR^{y'}R^{z'}$, $C(O)OR^{v'}$, $OC(O)R^{v'}$, $OC(O)NR^{y'}R^{z'}$, $NR^{y'}R^{z'}$, halogen, cyano, nitro, hydroxyl, amino, $C_{1-6}$ alkyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl.

In some embodiments, each $R^7$ is, independently, halogen, cyano, nitro, hydroxyl, amino, $C_{1-6}$ alkyl, $C_{1-6}$ haloalkyl, $C_{1-6}$ alkoxy, or $C_{1-6}$ haloalkoxy.

In some embodiments, each $R^a$, $R^b$, $R^c$, $R^d$, $R^e$, or $R^f$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl.

In some embodiments, each $R^a$, $R^b$, $R^c$, $R^d$, $R^e$, or $R^f$ is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl.

In some embodiments, each $R^a$, $R^b$, $R^c$, $R^d$, $R^e$, or $R^f$ is, independently, H, $C_{1-6}$ alkyl, $C_{1-6}$ haloalkyl, cycloalkyl, or cycloalkylalkyl.

In some embodiments, each $R^a$, $R^b$, $R^c$, $R^d$, $R^e$, or $R^f$ is, independently, H, $C_{1-6}$ alkyl, $C_{1-6}$ haloalkyl, heterocyloalkyl, or heterocycloalkylalkyl.

In some embodiments, each $R^a$, $R^b$, $R^c$, $R^d$, $R^e$, or $R^f$ is, independently, H, $C_{1-6}$ alkyl, aryl, or arylalkyl.

In some embodiments, each $R^a$, $R^b$, $R^c$, $R^d$, $R^e$, or $R^f$ is, independently, H, $C_{1-6}$ alkyl, heteroaryl, or heteroarylalkyl.

In some embodiments, each $R^a$, $R^b$, $R^c$, $R^d$, $R^e$, or $R^f$ is, independently, $C_{1-6}$ alkyl, heteroaryl, or heteroarylalkyl.

In some embodiments, each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl.

In some embodiments, each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl.

In some embodiments, each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, cycloalkyl, or cycloalkylalkyl.

In some embodiments, each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, heterocycloalkyl, or heterocycloalkylalkyl.

In some embodiments, each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, aryl, or arylalkyl.

In some embodiments, each $R^o$, $R^p$, $R^q$, $R^r$, $R^s$, $R^t$, $R^u$, $R^v$, $R^w$, $R^y$, or $R^z$, is, independently, H, $C_{1-6}$ alkyl, $C_{1-6}$ haloalkyl, heteroaryl, or heteroarylalkyl.

In some embodiments, each $R^o$, $R^p$, $R^q$, $R^r$, $R^s$, $R^t$, $R^u$, $R^v$, $R^w$, $R^y$, or $R^z$, is, independently, $C_{1-6}$ alkyl, $C_{1-6}$ haloalkyl, heteroaryl, or heteroarylalkyl.

In some embodiments:
$L_1$ is an unsubstituted $C_6$ alkylene bridge; and
$L_2$ is an unsubstituted $C_2$ alkylene bridge.

In some embodiments:
$L_1$ is an unsubstituted $C_5$ alkylene bridge; and
$L_2$ is an unsubstituted $C_3$ alkylene bridge.

In some embodiments:
$L_1$ is a $C_5$ alkylene bridge substituted with 1 oxo group; and
$L_2$ is an unsubstituted $C_3$ alkylene bridge.

In some embodiments:
$L_1$ is an unsubstituted $C_5$ alkylene bridge; and
$L_2$ is an unsubstituted $C_2$ alkylene bridge.

In some embodiments:
$L_1$ is an unsubstituted $C_4$ alkylene bridge; and
$L_2$ is an unsubstituted $C_3$ alkylene bridge.

In some embodiments:
$R^1$ is H, $C_{1-12}$ alkyl, $C_{2-12}$ alkenyl, $C_{2-12}$ alkynyl, $C_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl, wherein said $C_{1-12}$ alkyl, $C_{2-12}$ alkenyl, $C_{2-12}$ alkynyl, $C_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl is optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^q C(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups; and $L^2$ is a $C_{2-5}$ alkylene bridge which is optionally substituted with 1, 2, 3, or 4 groups independently selected from $OR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^yS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups.

In some embodiments:
$R^1$ is H, $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^q C(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups; and $L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^vS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups.

In some embodiments:

$R^1$ is H, $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups;

$L^1$ is a $C_{4-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $NR^sR^t$, $NR^q-C(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups; and $L^2$ is a $C_{2-3}$ alkylene bridge which is optionally substituted with 1, 2, 3, or 4 groups independently selected from $OR^u$, $SR^u$, $C(O)R^v$, $C(O)NR^yR^z$, $C(O)OR^v$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^vS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^7$ groups.

In some embodiments:

$R^1$ is $C_{1-12}$ alkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, cycloalkyl, cycloalkylalkyl, heterocycloalkyl, heterocycloalkylalkyl, heterocy-
cloalkylalkyl, aryl, arylalkyl, heteroaryl, and heteroarylalkyl are each optionally substituted by 1, 2, 3, or 4 $R^5$ groups;

$L^1$ is a $C_{4-6}$ alkylene bridge which is optionally substituted with 1, 2, 3, or 4 groups independently selected from $OR^o$, $C(O)R^p$, $NR^sR^t$, oxo, halogen, amino, $C_{1-6}$ alkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups; and $L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, or heteroarylalkyl wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl, are each optionally substituted by 1, 2, or 3 $R^7$ groups.

In some embodiments:

$R^1$ is $C_{1-12}$ alkyl, cycloalkyl, cycloalkylalkyl, heterocycloalkyl, heterocycloalkylalkyl, arylalkyl, or heteroaryl, wherein said $C_{1-12}$ alkyl, $C_{2-12}$ alkynyl, cycloalkyl, cycloalkylalkyl, heterocycloalkyl, heterocycloalkylalkyl, arylalkyl, and heteroaryl are each optionally substituted by 1, 2, 3, or 4 $R^5$ groups;

$L^1$ is a $C_{4-6}$ alkylene bridge which is optionally substituted with 1, 2, 3, or 4 groups independently selected from $OR^o$, $C(O)R^p$, $NR^sR^t$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl; and $L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl.

In some embodiments:

$R^1$ is $C_{1-12}$ alkyl, cycloalkyl, cycloalkylalkyl, heterocycloalkyl, heterocycloalkylalkyl, arylalkyl, or heteroaryl, wherein said $C_{1-12}$ alkyl, $C_{2-12}$ alkynyl, cycloalkyl, cycloalkylalkyl, heterocycloalkyl, heterocycloalkylalkyl, arylalkyl, and heteroaryl are optionally substituted by 1, 2, 3, or 4 $R^5$ groups;

$L^1$ is a $C_{4-6}$ alkylene bridge which is optionally substituted with 1 oxo group; and $L^2$ is an unsubstituted $C_{2-3}$ alkylene bridge.

In some embodiments:

$R^1$ is $C_{1-12}$ alkyl, cycloalkyl, cycloalkylalkyl, heterocycloalkyl, heterocycloalkylalkyl, arylalkyl, or heteroaryl;

$L^1$ is a $C_{4-6}$ alkylene bridge which is optionally substituted with 1 oxo group; and $L^2$ is an unsubstituted $C_{2-3}$ alkylene bridge.

In some embodiments:

$R^1$ is methyl, ethyl, n-butyl, isobutyl, tert-butyl, neopentyl, n-pentyl, n-hexyl, cyclohexyl, cyclopentylethyl, benzyl, phenylethyl, or thiophen-2-yl;

$L^1$ is a $C_{4-6}$ alkylene bridge which is optionally substituted with 1 oxo group; and $L^2$ is an unsubstituted $C_{2-3}$ alkylene bridge.

In some embodiments, when $L^2$ is a $C_3$ alkylene bridge substituted by 1, 2, 3, or 4 independently selected groups, then said $C_3$ alkylene bridge is not substituted by 1, 2, 3, or 4 oxo groups. In some embodiments, when $L^2$ is a $C_{2-5}$ alkylene bridge substituted by 1, 2, 3, or 4 independently selected groups, then said $C_{2-5}$ alkylene bridge is not substituted by 1, 2, 3, or 4 oxo groups.

In some embodiments, the present invention provides the compounds:
N-5,6,9,10,11,12-hexahydro-4H,8H-cyclohepta[4,5]pyrrolo [3,2,1-ij]quinolin-2-yl-3,3-dimethylbutanamide;
N-5,6,9,10,11,12-hexahydro-4H,8H-cyclohepta[4,5]pyrrolo [3,2,1-ij]quinolin-2-yl-2,2-dimethylpropanamide;
N-5,6,9,10,11,12-hexahydro-4H,8H-cyclohepta[4,5]pyrrolo [3,2,1-ij]quinolin-2-ylhexanamide;
N-5,6,9,10,11,12-hexahydro-4H,8H-cyclohepta[4,5]pyrrolo [3,2,1-ij]quinolin-2-yl-3-phenylpropanamide;
N-5,6,9,10,11,12-hexahydro-4H,8H-cyclohepta[4,5]pyrrolo [3,2,1-ij]quinolin-2-ylthiophene-2-carboxamide;
N-5,6,9,10,11,12-hexahydro-4H,8H-cyclohepta[4,5]pyrrolo [3,2,1-ij]quinolin-2-yl-3-methylbutanamide;
N-5,6,9,10,11,12-hexahydro-4H,8H-cyclohepta[4,5]pyrrolo [3,2,1-ij]quinolin-2-ylpropanamide;
N-5,6,9,10,11,12-hexahydro-4H,8H-cyclohepta[4,5]pyrrolo [3,2,1-ij]quinolin-2-ylcyclohexanecarboxamide;
N-5,6,9,10,11,12-hexahydro-4H,8H-cyclohepta[4,5]pyrrolo [3,2,1-ij]quinolin-2-ylpentanamide;
N-4,5,8,9,10,11-hexahydro-7H-cyclohepta[b]pyrrolo[3,2,1-hi]indol-2-yl-3,3-dimethylbutanamide;
N-4,5,8,9,10,11-hexahydro-7H-cyclohepta[b]pyrrolo[3,2,1-hi]indol-2-ylacetamide;
N-4,5,8,9,10,11-hexahydro-7H-cyclohepta[b]pyrrolo[3,2,1-hi]indol-2-ylpentanamide;
N-4,5,8,9,10,11-hexahydro-7H-cyclohepta[b]pyrrolo[3,2,1-hi]indol-2-yl-2-phenylacetamide;
N-4,5,8,9,10,11-hexahydro-7H-cyclohepta[b]pyrrolo[3,2,1-hi]indol-2-yl-3-methylbutanamide;
3-cyclopentyl-N-4,5,8,9,10,11-hexahydro-7H-cyclohepta [b]pyrrolo[3,2,1-hi]indol-2-ylpropanamide;
N-5,6,8,9,10,11-hexahydro-4H-pyrido[3,2,1-jk]carbazol-2-yl-3,3-dimethylbutanamide;
N-5,6,8,9,10,11-hexahydro-4H-pyrido[3,2,1-jk]carbazol-2-ylhexanamide;
N-5,6,8,9,10,11-hexahydro-4H-pyrido[3,2,1-jk]carbazol-2-yl-3-methylbutanamide;
N-5,6,8,9,10,11-hexahydro-4H-pyrido[3,2,1-jk]carbazol-2-ylacetamide;
N-4,5,7,8,9,10,11,12-octahydrocycloocta[b]pyrrolo[3,2,1-hi]indol-2-ylhexanamide;
3,3-dimethyl-N-4,5,7,8,9,11,12-octahydrocycloocta[b]pyrrolo[3,2,1-hi]indol-2-ylbutanamide;
N-4,5,7,8,9,10,11,12-octahydrocycloocta[b]pyrrolo[3,2,1-hi]indol-2-ylheptanamide; or
3,3-dimethyl-N-(8-oxo-5,6,9,10,11,12-hexahydro-4H,8H-cyclohepta[4,5]pyrrolo[3,2,1-ij]quinolin-2-yl)butanamide;

or pharmaceutically acceptable salt thereof.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted. As used herein, the term "substituted" means that a hydrogen atom is removed and replaced by a substitutent. As used herein, the phrase "substituted by oxo" means that two hydrogen atoms are removed from a carbon atom and replaced by an oxygen bound by a double bond to the carbon atom. It is understood that the number of substituents for a given atom is limited by its valency.

As used herein, the term "acyl", employed alone or in combination with other terms, refers to a group of formula —C(O)-alkyl, wherein said alkyl group has 1 to 6 carbons.

As used herein, the term "alkyl", employed alone or in combination with other terms, refers to a saturated hydrocarbon group that may be straight-chain or branched. In some embodiments, the alkyl group contains 1 to 12 or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like.

As used herein, the term "alkylamino" refers to a group of formula —NH(alkyl), wherein the alkylene group and alkyl group each have 1 to 6 carbons.

As used herein, the term "alkylcarbamyl" refers to a group of formula —C(O)—NH(alkyl), wherein the alkyl group has 1 to 6 carbons.

As used herein, the term "alkylcarbamyloxy" refers to a group of formula —OC(O)NH(alkyl), wherein the alkyl group has 1 to 6 carbons.

As used herein, the term "alkylene" refers to a divalent alkyl linking group. Examples of alkylene groups include, but are not limited to, ethan-1,2-diyl, propan-1,3-diyl, propan-1, 2-diyl, butan-1,4-diyl, butan-1,3-diyl, butan-1,2-diyl, 2-methyl-propan-1,3-diyl, and the like.

As used herein, the term "alkylene bridge" refers to a straight-chain divalent alkyl linking group.

As used herein, "alkenyl", employed alone or in combination with other terms, refers to an alkyl group having one or more double carbon-carbon bonds. In some embodiments, the alkenyl moiety contains 2 to 10 or 2 to 6 carbon atoms. Example alkenyl groups include, but are not limited to, ethenyl, n-propenyl, isopropenyl, n-butenyl, sec-butenyl, and the like.

As used herein, the term "alkenylene", employed alone or in combination with other terms, refers to a divalent alkenyl group. In some embodiments, the alkenylene moiety contains 2 to 12 carbon atoms. In some embodiments, the alkenylene moiety contains 2 to 6 carbon atoms. Example alkenylene groups include, but are not limited to, ethen-1,2-diyl, propen-1,3-diyl, propen-1,2-diyl, buten-1,4-diyl, buten-1,3-diyl, buten-1,2-diyl, 2-methyl-propen-1,3-diyl, and the like.

As used herein, "alkynyl", employed alone or in combination with other terms, refers to an alkyl group having one or more triple carbon-carbon bonds. Example alkynyl groups include, but are not limited to, ethynyl, propyn-1-yl, propyn-2-yl, and the like. In some embodiments, the alkynyl moiety contains 2 to 10 or 2 to 6 carbon atoms.

As used herein, the term "alkynylene", employed alone or in combination with other terms, refers to a divalent alkynyl group. In some embodiments, the alkynylene moiety contains 2 to 12 carbon atoms. In some embodiments, the alkynylene moiety contains 2 to 6 carbon atoms. Example alkynylene groups include, but are not limited to, ethyn-1,2-diyl, propyn-1,3,-diyl, 1-butyn-1,4-diyl, 1-butyn-1,3-diyl, 2-butyn-1,4-diyl, and the like.

As used herein, the term "alkoxy", employed alone or in combination with other terms, refers to an group of formula —O-alkyl. Example alkoxy groups include methoxy, ethoxy, propoxy (e.g., n-propoxy and isopropoxy), t-butoxy, and the like.

As used herein, the term "alkylsulfinyl" refers to a group of formula —S(O)-alkyl, wherein the alkyl group has 1 to 6 carbons.

As used herein, the term "alkylsulfonyl" refers to a group of formula —S(O)$_2$-alkyl, wherein the alkyl group has 1 to 6 carbons.

As used herein, the term "alkylthio" refers to a group of formula —S-alkyl, wherein the alkyl group has 1 to 6 carbon atoms.

As used herein, the term "amino", employed alone or in combination with other terms, refers to a group of formula —NH$_2$.

As used herein, the term "aryl", employed alone or in combination with other terms, refers to a monocyclic or polycyclic (e.g., having 2, 3 or 4 fused or covalently linked rings) aromatic hydrocarbon moiety, such as, but not limited to, phenyl, 1-naphthyl, 2-naphthyl, anthracenyl, phenanthrenyl, and the like. In some embodiments, aryl groups have from 6 to 20 carbon atoms, about 6 to 10 carbon atoms, or about 6 to 8 carbons atoms.

As used herein, the term "arylalkyl" refers to a group of formula -alkylene-aryl. In some embodiments, the alkyl portion of the arylalkyl group has 1 to 6 carbon atoms. In some embodiments, the alkyl portion of the arylalkyl group is methyl. In some embodiments, the arylalkyl group is benzyl.

As used herein, the term "arylalkenyl" refers to a group of formula -alkenylene-aryl.

As used herein, the term "arylalkynyl" refers to a group of formula -alkynylene-aryl.

As used herein, the term "aryloxy" refers to a group of formula —O-aryl.

As used herein, the term "carbamyl" refers to a group of formula —C(O)NH$_2$.

As used herein, the term "carbonyl", employed alone or in combination with other terms, refers to a —C(O)— group, which is a divalent one-carbon moiety further bonded to an oxygen atom with a double bond.

As used herein, the term "carboxy" refers to a group of formula —C(O)OH.

As used herein, the term "cycloalkyl", employed alone or in combination with other terms, refers to a non-aromatic cyclic hydrocarbon moiety, which may optionally contain one or more alkenylene or alkynylene groups as part of the ring structure. Cycloalkyl groups can include mono- or polycyclic (e.g., having 2, 3 or 4 fused or covalently linked rings) ring systems. Also included in the definition of cycloalkyl are moieties that have one or more aromatic rings fused (i.e., having a bond in common with) to the cycloalkyl ring, for example, benzo derivatives of pentane, pentene, hexane, and the like. In some embodiments, the cycloalkyl group has 3 to 14 ring members, 3 to 10 ring members, or 0.3 to 8 ring members. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "cycloalkylalkyl" refers to a group of formula -alkylene-cycloalkyl. In some embodiments, the alkyl portion of the cycloalkylalkyl group has 1 to 6 carbon atoms.

As used herein, the term "cycloalkylalkenyl" refers to a group of formula -alkenylene-cycloalkyl.

As used herein, the term "cycloalkylalkynyl" refers to a group of formula -alkynylene-cycloalkyl.

As used herein, the term "cycloalkyloxy" refers to a group of formula —O-cycloalkyl.

As used herein, the term "cyano" refers to a group of formula —CN, wherein the carbon and nitrogen atoms are bound together by a triple bond.

As used herein, the term "dialkylamino" refers to a group of formula —N(alkyl)$_2$, wherein the alkylene group and two alkyl groups each has, independently, 1 to 6 carbons.

As used herein, the term "dialkylcarbamyl" refers to a group of formula —C(O)—N(alkyl)$_2$, wherein the alkyl groups each has, independently, 1 to 6 carbons.

As used herein, the term "dialkylcarbamyloxyl" refers to a group of formula —OC(O)N(alkyl)$_2$, wherein the alkyl groups each has, independently, 1 to 6 carbon atoms.

As used herein, the term "formyl", employed alone or in combination with other terms, refers to a group of formula —C(O)—H.

As used herein, "haloalkoxy", employed alone or in combination with other terms, refers to a group of formula —O-haloalkyl. An example haloalkoxy group is OCF$_3$.

As used herein, the term "haloalkyl", employed alone or in combination with other terms, refers to an alkyl group having from one halogen atom to 2n+1 halogen atoms which may be the same or different, where "n" is the number of carbon atoms in the alkyl group.

As used herein, the terms "halo" and "halogen", employed alone or in combination with other terms, refer to fluoro, chloro, bromo, and iodo.

As used herein, the term "heteroaryl", "heteroaryl ring", or "heteroaryl group", employed alone or in combination with other terms, refers to a monocyclic or polycyclic (e.g., having 2, 3 or 4 fused or covalently linked rings) aromatic hydrocarbon moiety, having one or more heteroatom ring members selected from nitrogen, sulfur and oxygen. When the heteroaryl group contains more than one heteroatom ring member, the heteroatoms may be the same or different. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. In some embodiments, the heteroaryl group has 5 to 10 carbon atoms.

As used herein, the term "heteroarylalkyl" refers to a group of formula -alkylene-heteroaryl. In some embodiments, the alkyl portion of the heteroaryl group has 1 to 6 carbon atoms.

As used herein, the term "heteroarylalkenyl" refers to a group of formula -alkenylene-heteroaryl.

As used herein, the term "heteroarylalkynyl" refers to a group of formula -alkynylene-heteroaryl.

As used herein, the term "heteroaryloxy" refers to a group of formula —O-heteroaryl.

As used herein, the term "heterocycloalkyl", "heterocycloalkyl ring", or "heterocycloalkyl group", employed alone or in combination with other terms, refers to non-aromatic ring system, which may optionally contain one or more alkenylene or alkynylene groups as part of the ring structure, and which has at least one heteroatom ring member selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused or covalently bonded rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. In some embodiments, the heterocycloalkyl group has 3 to 20 ring-forming atoms, 3 to 10 ring-forming atoms, or about 3 to 8 ring forming atoms. The carbon atoms or hetereoatoms in the ring(s) of the heterocycloalkyl group can be oxidized to form a carbonyl, or sulfonyl group (or other oxidized linkage) or a nitrogen atom can be quaternized.

As used herein, the term "heterocycloalkylalkyl" refers to a group of formula -alkyl-heterocycloalkyl. In some embodiments, the alkyl portion of the heterocycloalkylalkyl group has 1 to 6 carbon atoms. In some embodiments, the alkyl portion of the heterocycloalkylalkyl group is methylene. In some embodiments, the heterocycloalkylalkyl group is (tetrahydrofur-2-yl)methyl.

As used herein, the term "heterocycloalkylalkenyl" refers to a group of formula -alkenylene-heterocycloalkyl.

As used herein, the term "heterocycloalkylalkynyl" refers to a group of formula -alkynylene-heterocycloalkyl.

As used herein, the term "heterocycloalkyloxy" refers to a group of formula —O-heterocycloalkyl.

As used herein, the term "hydroxyl" refers to a group of formula —OH.

As used herein, the term "nitro" refers to a group of formula —$NO_2$.

As used herein, the term "sulfinyl", employed alone or in combination with other terms, refers to —S(O)— group, which is a divalent one-sulfur moiety further bonded to an oxygen atom with a double bond.

As used herein, the term "sulfonyl", employed alone or in combination with other terms, refers to a —$S(O)_2$— group, which is a divalent one-sulfur moiety further bonded to two oxygen atoms via double bonds.

As used herein, the term "thio", employed alone or in combination with other terms, refers to a —S— group, which is a divalent one-sulfur moiety.

The compounds in this invention may contain one or more asymmetric centers, which can thus give rise to optical isomers (enantiomers) and diastereomers. While shown without respect to the stereochemistry in Formula I, the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. The use of these compounds is intended to cover the racemic mixture or either of the chiral enantiomers.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

One skilled in the art will also recognize that it is possible for tautomers to exist for the compounds of the present invention. The present invention includes all such tautomers even though not shown in the formulas herein.

Compounds of the invention can also include all isotopes of atoms occurring in the intermediates or final compounds. Isotopes include those atoms having the same atomic number but different mass numbers. For example, isotopes of hydrogen include tritium and deuterium.

The compounds of the present invention also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

In some embodiments, the compounds of Formula I are prodrugs. As used herein, "prodrug" refers to a moiety that releases a compound of the invention when administered to a patient. Prodrugs can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference in their entireties.

Pharmaceutical Compositions, Methods and Uses

The compounds of Formula I, and embodiments thereof, are useful in treating disorders treatable by potassium channel modulators. Disorders that are treatable by potassium channel modulators includes those disorders whose symptomatology, progression, development, and/or pathology affected by the potassium channel modulation. These disorders include, but are not limited to, cardiovascular diseases; central nervous system disorders; and urinary incontinence.

As used herein, the term "central nervous system disorder" refers to a disorder associated with the nervous system of a patient, including, but not limited to the brain, spinal cord, and nerves. As used herein, the term "cardiovascular disease" refers to a disorder, injury, or disease that detrimentally affects the heart or blood vessels.

In some embodiments, the present invention provides a method of treating ischemic heart disease, myocardial infarction, cardiac arrhythmia, hypertension, or angina pectoris in an individual in need thereof, comprising administering to said individual a therapeutically effective amount of a compound of Formula I.

In some embodiments, the present invention provides a method of treating epilepsy, episodic ataxia type 1, paroxysmal dyskinesia, neurodegenerative spincerebrallar ataxia, Parkinson's disease, Alzheimer's disease, or multiple sclerosis in an individual in need of treatment thereof, comprising administering to said individual a therapeutically effective amount of a compound of Formula I.

In some embodiments, the present invention provides a method of treating depression, generalized anxiety disorder, bulimia nervosa, or anorexia nervosa in an individual in need thereof, comprising administering to said individual a therapeutically effective amount of a compound of Formula I.

In some embodiments, the present invention provides a method of treating type I diabetes or type II diabetes in an individual in need thereof, comprising administering to said individual a therapeutically effective amount of a compound of Formula I.

In some embodiments, the present invention provides a method of treating allergy or asthma in an individual in need thereof, comprising administering to said individual a therapeutically effective amount of a compound of Formula I.

In some embodiments, the present invention provides a method of treating urinary incontinence, irritable bowel syndrome, or irritable bladder syndrome in an individual in need thereof, comprising administering to said individual a therapeutically effective amount of a compound of Formula I.

In some embodiments, the present invention provides a method of treating pain or inflammation in an individual in need thereof, comprising administering to said individual a therapeutically effective amount of a compound of Formula I.

In some embodiments, the present invention provides a method of modulating a potassium channel in an individual in need thereof, comprising administering to said individual a therapeutically effective amount of a compound of Formula I.

The methods may utilize all of the embodiments for the compounds of Formula I hereinbefore described, including various combinations and subcombinations of the embodiments.

The present invention further provides a use of a compound of Formula I, or pharmaceutically acceptable salt thereof, for the production of medicament for use in the treatment of disorders remedied or alleviated by potassium channel modulation.

In some embodiments, the present invention provides a use of a compound of Formula I, or pharmaceutically acceptable salt thereof, for the production of medicament for use in the treatment of ischemic heart disease, myocardial infarction, cardiac arrhythmia, hypertension, or angina pectoris.

In some embodiments, the present invention provides a use of a compound of Formula I, or pharmaceutically acceptable salt thereof, for the production of medicament for use in the treatment of epilepsy, episodic ataxia type 1, paroxysmal dyskinesia, neurodegenerative spincerebrallar ataxia, Parkinson's disease, Alzheimer's disease, or multiple sclerosis.

In some embodiments, the present invention provides a use of a compound of Formula I, or pharmaceutically acceptable salt thereof, for the production of medicament for use in the treatment of depression, generalized anxiety disorder, bulimia nervosa, or anorexia nervosa, In some embodiments, the present invention provides a use of a compound of Formula I, or pharmaceutically acceptable salt thereof, for the production of medicament for use in the treatment of type I diabetes or type II diabetes.

In some embodiments, the present invention provides a use of a compound of Formula I, or pharmaceutically acceptable salt thereof, for the production of medicament for use in the treatment of allergy or asthma.

In some embodiments, the present invention provides a use of a compound of Formula I, or pharmaceutically acceptable salt thereof, for the production of medicament for use in the treatment of urinary incontinence, irritable bowel syndrome, or irritable bladder syndrome.

In some embodiments, the present invention provides a use of a compound of Formula I, or pharmaceutically acceptable salt thereof, for the production of medicament for use in the treatment of pain or inflammation.

The uses may utilize all of the embodiments for the compounds of Formula I hereinbefore described, including various combinations and subcombinations of the embodiments.

The present invention further provides a compound of Formula I, or pharmaceutically acceptable salt thereof, for use in a method of treatment of disorders remedied or alleviated by potassium channel modulation.

In some embodiments, the present invention provides a compound of Formula I, or pharmaceutically acceptable salt thereof, for use in a method of treatment of ischemic heart disease, myocardial infarction, cardiac arrhythmia, hypertension, or angina pectoris by therapy.

In some embodiments, the present invention provides a compound of Formula I, or pharmaceutically acceptable salt thereof, for use in a method of treatment of epilepsy, episodic ataxia type 1, paroxysmal dyskinesia, neurodegenerative spincerebrallar ataxia, Parkinson's disease, Alzheimer's disease, or multiple sclerosis by therapy.

In some embodiments, the present invention provides a compound of Formula I, or pharmaceutically acceptable salt thereof, for use in a method of treatment of depression, generalized anxiety disorder, bulimia nervosa, or anorexia nervosa by therapy.

In some embodiments, the present invention provides a compound of Formula I, or pharmaceutically acceptable salt thereof, for use in a method of treatment of type I diabetes or type II diabetes by therapy.

In some embodiments, the present invention provides a compound of Formula I, or pharmaceutically acceptable salt thereof, for use in a method of treatment of allergy or asthma by therapy.

In some embodiments, the present invention provides a compound of Formula I, or pharmaceutically acceptable salt thereof, for use in a method of treatment of urinary incontinence, irritable bowel syndrome, or irritable bladder syndrome by therapy.

In some embodiments, the present invention provides a compound of Formula I, or pharmaceutically acceptable salt thereof, for use in a method of treatment of pain or inflammation by therapy.

The compounds for use in method of treatment can include all of the embodiments for the compounds of Formula I hereinbefore described, including various combinations and subcombinations of the embodiments.

As used herein, the term "individual" refers to any animal, including mammals, preferably mice, rats, other rodents, rabbits, dogs, cats, swine, cattle, sheep, horses, or primates, and most preferably humans. In some embodiments, the individual is an adult, child, or infant. In some embodiments, the individual is a mammal. In some embodiments, the individual is a human.

The phrase "therapeutically effective amount" refers to the amount of a compound of the invention that elicits the biological or medicinal response in a tissue, system, animal, individual, patient, or human that is being sought by a researcher, veterinarian, medical doctor or other clinician. The desired biological or medicinal response may include preventing the disorder in an individual (e.g., preventing the disorder in an individual that may be predisposed to the disorder, but does not yet experience or display the pathology or symptomatology of the disease). The desired biological or medicinal response may also include inhibiting the disorder in an individual that is experiencing or displaying the pathology or symptomatology of the disorder (i.e., arresting or slowing further development of the pathology and/or symptomatology). The desired biological or medicinal response may also include ameliorating the disorder in an individual that is experiencing or displaying the pathology or symptomatology of the disease (i.e., reversing the pathology or symptomatology).

The therapeutically effective amount provided in the treatment of a specific disorder will vary depending the specific disorder(s) being treated, the size, age, and response pattern of the individual the severity of the disorder(s), the judgment of the attending clinician, the manner of administration, and the purpose of the administration, such as prophylaxis or therapy. In general, effective amounts for daily oral administration may be about 0.01 to 50 mg/kg, preferably about 0.1 to 10 mg/kg and effective amounts for parenteral administration may be about 0.01 to 10 mg/kg, preferably about 0.1 to 5 mg/kg.

The compounds of the invention may be administered orally or parenterally, neat or in combination with one or more conventional pharmaceutically acceptable carriers or excipients. Accordingly, the present invention provides a pharmaceutical composition which comprises a compound of Formula I, or a pharmaceutically salt thereof, and a pharmaceutically acceptable carrier. The pharmaceutical compositions can include all of the embodiments for the compounds of Formula I hereinbefore described, including various combinations and subcombinations of the embodiments.

Solid carriers suitable for use in the compositions of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided active ingredient. As used herein, the term "active ingredient" refers to a compound of Formula I, or a pharmaceutically acceptable salt thereof. In tablets, the active ingredient may be mixed with a carrier having the necessary compression properties in suitable proportions and compacted in the shape and size desired. The powders and tablets may contain up to 99% by weight of the active ingredient. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the compositions of the invention. The active ingredient may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate. Sterile liquid carriers can be used in sterile liquid form compositions for parenteral administration. The liquid carrier for pressurized compositions can be halogenated hydrocarbon or other pharmaceutically acceptable propellant.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

The compounds of the invention can be administered rectally or vaginally in the form of a conventional suppository. For administration by intranasal or intrabronchial inhalation or insufflation, the compounds of the present invention can be formulated into an aqueous or partially aqueous solution, which can then be utilized in the form of an aerosol. The compounds of the present invention can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

The pharmaceutical composition can be administered in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

In some embodiments of the methods, uses, and compositions herein, the compounds of Formula I, or pharmaceutically acceptable salts thereof, are administered as prodrugs as described herein.

Syntheses and Processes

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes described herein can be monitored according to any suitable method known in the art. For example, product formation can be monitored by spectroscopic means, such as nuclear magnetic resonance spectroscopy (e.g., $^1$H or $^{13}$C NMR) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

According to Scheme 1, step (a), an appropriately substituted aniline of Formula II is treated at 120° C. with a 2-halocycloalkanone of Formula II, such as 2-chlorocyclohexanone, and a base, such as pyridine, in a suitable solvent such as 2-methoxyethanol, to provide the desired tetracyclic indole of Formula IV. Alternatively, in step (b), an appropriately substituted aniline of Formula II is treated with a suitable nitrous acid or nitrite in the presence of a protic acid, such as sodium nitrite and 1 N HCl, to afford the corresponding N-nitroso compound which is reduced with an appropriate reducing agent, such as zinc in acetic acid, to produce the desired hydrazine of Formula V. Treatment of the hydrazine in step (c) with a cyclic ketone of Formula VI under Fisher indolization conditions, such as aqueous sulfuric acid at reflux, provides the desired tetracyclic indole of Formula IV.

In step (d), treatment of the tetracyclic indole of Formula IV under nitration conditions, such as potassium nitrate in concentrated sulfuric acid at 0° C. (Block et al. J. Med. Chem. 2002, 45, 3509), affords the nitro-indole compound of Formula VII. Reduction of the nitro group to the amine in step (e) is accomplished by a number of known reduction procedures, including hydrogenolysis (hydrogen with a metal catalyst) or iron in acetic acid to provide the amino-indole of Formula VIII. In step (f), acylation of the amine with an appropriate acylating agent of Formula IX, such as an acid chloride, in the presence of a base, such as pyridine or triethylamine, in a suitable solvent, such as dichloromethane or dichloroethane, provides the target amide compounds of Formula I.

Alternatively, the compounds of Formula I can be prepared as shown in Scheme II. Accordingly, in step (g), treatment of the tetracyclic indole of Formula IV under nitration conditions, such as nitric acid in concentrated sulfuric acid at room temperature, affords the keto-nitro-indole compound of Formula X, wherein $L_1$ is substituted by oxo. In step (h), reduction of the keto-nitro-indole to a keto-amino-indole of Formula XI, wherein $L_1$ is substituted by oxo, is accomplished by a number of known reduction procedures, including hydrogenolysis (hydrogen with a metal catalyst). In step (i), acylation of the amine with an acylating agent of Formula IX, such as an acid chloride or acid anhydride, in the presence of a base, such as pyridine or triethylamine, in a suitable solvent, such as dichloromethane or dichloroethane, provides the target keto-amide compounds of Formula I, wherein $L_1$ is substituted by oxo.

The keto-nitro-indole can also be reduced the amino-indole of Formula VIII as in step (j) using an appropriate reducing agent, such as lithium aluminum hydride, in an appropriate solvent, such as dioxane, at elevated temperatures.

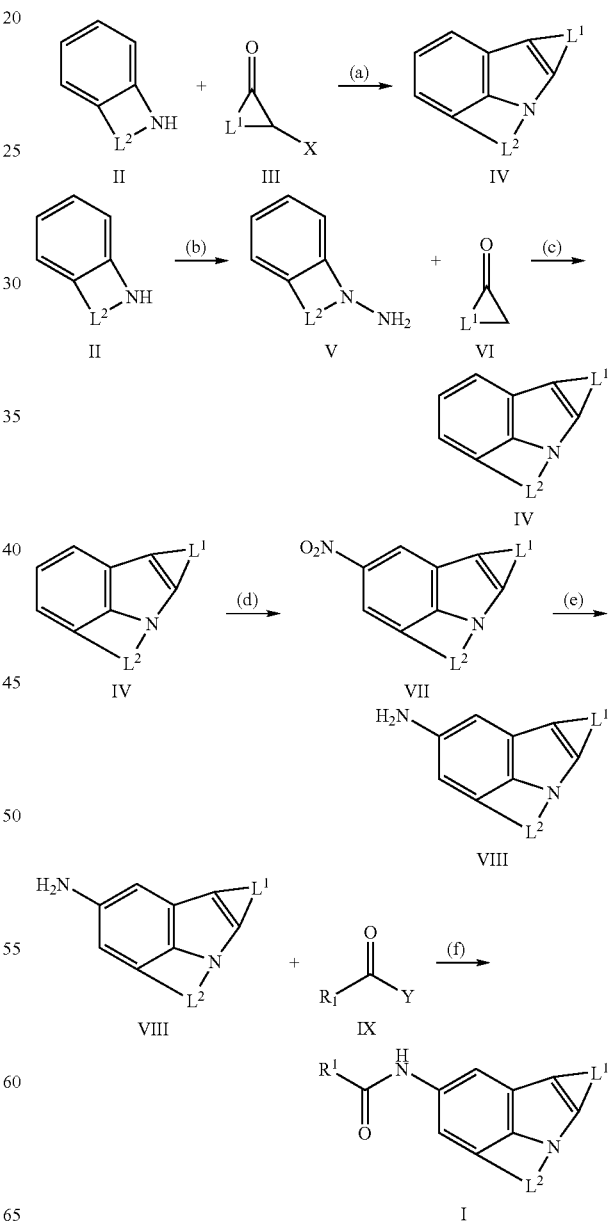

Scheme 1

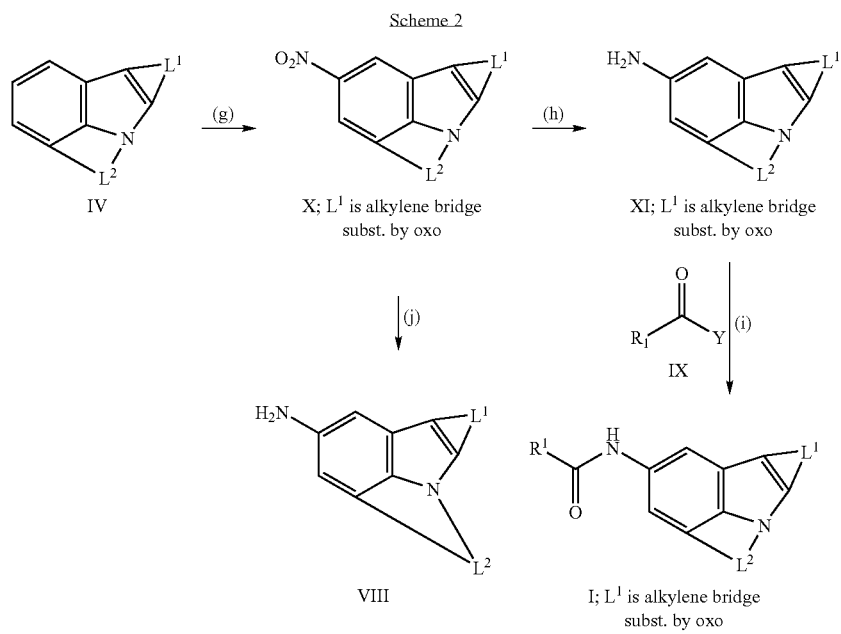

Another possible route to the tetracyclic indole of Formula I is depicted in Scheme 3. Hydrogenation of 6-nitroquinoline, Formula XII, using a metal catalysis, such as palladium on carbon, in a suitable solvent, such as ethanol, affords 2-aminoquinoline, Formula XIII. Coupling of 2-aminoquinoline with a suitable electrophile of Formula IX, such as an acid chloride, acid anhydride, or other activated carboxylic acid, provides the amide of Formula XIV. Catalytic hydrogenation of the quinoline with a suitable metal catalyst, such as platinum on carbon, in the presence of an acid, such as trifluoroacetic acid, provides the tetrahydroquinoline of Formula XV, which upon treatment with a suitable acid, such as hydrochloric acid, provides the tetrahydroquinoline salt. Treatment of the tetrahydroquinoline salts with a suitable 2-halocycloalkanone of Formula III, such as 2-chlorocyclohexanone, in a suitable solvent, such as ethanol, at elevated temperatures, such as 150° C., either thermally or with microwave irradiation provides the target amide compounds of Formula XVI.

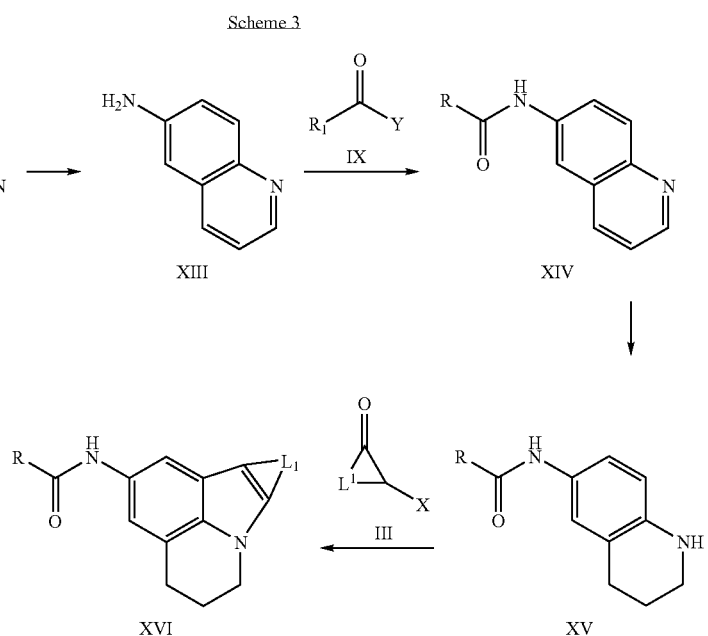

In accordance with the Schemes herein, the present invention further provides synthetic processes for producing the compounds of Formula I, and embodiments thereof. In some embodiments, the synthetic process comprises reacting a compound of Formula VIII:

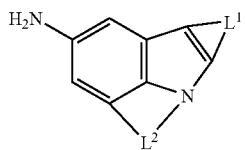

VIII with a compound of Formula IX:

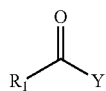

IX under conditions and for a time sufficient to produce a compound of Formula I, or embodiment thereof, wherein:

$R_1$, $L_1$, and $L_2$ are defined as in the previously described embodiments;

Y is halogen, $C_{1-12}$ alkoxy, hydroxyl, amino, $OC(O)R^{yy}$, or $OC(O)R_1$; and $R^{yy}$ is $C_{1-12}$ alkyl;

provided that the compound of Formula I is not N-(4-oxo-5,6,8,9,10,11-hexahydro-4H-pyrido[3,2,1-jk]carbazol-2-yl)-acetamide, or pharmaceutically acceptable salt thereof.

In some embodiments, Y is halogen.

In some embodiments, Y is chloro.

In some embodiments, the compound of Formula VIII is produced by a process comprising:

(a) reacting a compound of Formula IV:

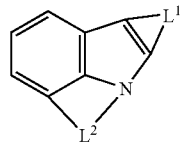

IV with a nitrating agent under conditions and for a time sufficient to produce a compound of Formula VII:

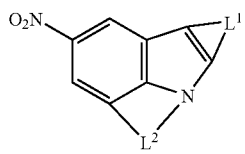

VII (b) reducing the nitro group of the compound of Formula VII under conditions and for a time sufficient to produce a compound of Formula VIII.

Suitable nitrating agents include, but are not limited to, nitric acid; mixtures of nitric acid and another acid, such as sulfuric acid or acetic acid; nitric acid and acetic anhydride; $N_2O_5$ in the presence of drying agent such as $P_2O_5$; esters of nitric acid, including, but not limited to, methyl nitrate and ethyl nitrate, in the presence of alkaline media, a protic acid, or a Lewis acid; metallic nitrites, such as sodium nitrite or potassium nitrite, in the presence of an acid, such as trifluoroacetic acid or sulfuric acid; $N_2O_4$; and nitronium salts such as $NO_2^+BF_4^-$, $NO_2^+PF_6^-$, $NO_2^+CF_3SO_3^-$. Other suitable nitrating agents are summarized in Schofield, "Aromatic Nitration," (Cambridge University Press, Cambridge, 1980); and Hogget, et al., "Nitration and Aromatic Reactivity," 122-145, 163-222 (Cambridge University Press, London, 1971); each of which is incorporated herein by reference in its entirety.

In some embodiments, the nitrating agent comprises nitric acid, $N_2O_4$, $N_2O_5$, esters of nitric acid, metallic nitrites, or nitronium salts. In some embodiments, the nitrating agent comprises potassium nitrate.

The nitro group of compound VII can be reduced using a variety of reducing agents including, but not limited to, zinc, iron, tin, and other metals in the presence of an acid; lithium aluminum hydride; hot liquid paraffin; aluminum hydride-aluminum chloride; sodium dihydro(trithio)borate; and sulfides such as NaHS, ammonium sulfide, or polysulfides. Reduction can also be accomplished through catalytic hydrogenation using methods known to one of skill in the art. Suitable hydrogenation catalysts include, but are not limited to, platinum, palladium, palladium on carbon, and nickel, as well as the catalysts in Rylander, "Organic Syntheses with Nobel Metal Catalysts," 1-59 (Academic Press, New York, 1973), which is incorporated by reference in its entirety.

In some embodiments, the reducing comprises reacting a compound of Formula VII with a reducing agent comprising zinc, tin, iron, lithium aluminum hydride, a sulfide, hot liquid paraffin, aluminum hydride-aluminum chloride, hydrazine, sodium dihydro(trithio)borate, or hydrogen gas.

In some embodiments, the compound of Formula IV is produced by a process comprising reacting a compound of Formula II:

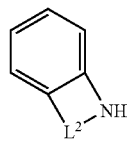

II with a compound of Formula III:

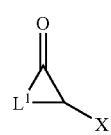

III under conditions and for a time sufficient to form a compound of Formula IV; wherein X is halogen.

In some embodiments, X is chloro.

In some embodiments, the compound of Formula IV is produced by a process comprising reacting a compound of Formula V:

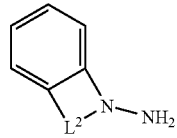

V with a compound of Formula VI:

VI in the presence of a Fischer indole catalyst under conditions and for a time sufficient to form said compound of Formula IV.

As used herein, the term "Fischer indole catalyst" refers to a reagent or reagents that are useful for catalyzing a Fischer indole synthesis (see Robinson, "The Fischer Indole Synthesis," Wiley, New York, 1983, incorporated herein by reference in its entirety). In some embodiments, the Fischer indole catalyst is a protic acid, Lewis acid, or metallic halides. Suitable protic acids include, but are not limited to, sulfuric acid, hydrochloric acid, and polyphosphoric acid. Suitable Lewis acids include, but are not limited to aluminum chloride, boron trifluoride, or iron chloride.

In some embodiments, the Fischer indole catalyst comprises a protic acid, Lewis acid, or metallic halide. In some embodiments, the Fischer indole catalyst is sulfuric acid, hydrochloric acid, polyphosphoric acid, zinc chloride, aluminum chloride, boron trifluoride, or iron chloride. In some embodiments, the Fischer indole catalyst is sulfuric acid.

The present invention further provides a synthetic process comprising reacting a compound of Formula XV:

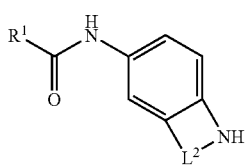

XV with a compound of Formula III:

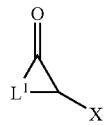

III under conditions and for a time sufficient to produce a compound of Formula I:

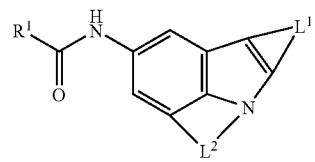

I wherein:
  $R_1$, $L_1$, and $L_2$ are defined as in the previously described embodiments;
  X is halogen;
  Y is halogen, $C_{1-12}$ alkoxy, hydroxyl, amino, $OC(O)R^{yy}$, or $OC(O)R^1$; and
  $R^{yy}$ is $C_{1-12}$ alkyl;

provided that the compound of Formula I is not N-(4-oxo-5,6,8,9,10,11-hexahydro-4H-pyrido[3,2,1-jk]carbazol-2-yl)-acetamide, or pharmaceutically acceptable salt thereof.

In some embodiments, X is chloro.

In some embodiments:
  $R^1$ is $C_{1-12}$ alkyl cycloalkyl, cycloalkylalkyl, heterocycloalkyl, heterocycloalkylalkyl, arylalkyl, or heteroaryl;
  $L^1$ is a $C_{4-6}$ alkylene bridge which is optionally substituted with 1 oxo; and
  $L^2$ is an unsubstituted $C_{2-3}$ alkylene bridge.

In some embodiments:
  $R^1$ is methyl, ethyl, n-butyl, isobutyl, tert-butyl, neopentyl, n-pentyl, n-hexyl, cyclohexyl, cyclopentylethyl, benzyl, phenylethyl, or thiophen-2-yl;
  $L^1$ is a $C_{4-6}$ alkylene bridge which is optionally substituted with 1 oxo; and
  $L^2$ is an unsubstituted $C_{2-3}$ alkylene bridge.

EXAMPLES

In order that the invention disclosed herein may be more efficiently understood, examples are provided below. It should be understood that these examples are for illustrative purposes only and are not to be construed as limiting the invention in any manner.

The following abbreviations are used herein: "Me" is methyl; "min" is minute(s); "h" is hour(s); "MS" is mass spectrometry; HPLC is high pressure liquid chromatography; "RT" is retention time; "ACN" is acetonitrile; "MeOH" is methanol; "ESI" is electron spray ionization; "Ammon. Form. Buff." is ammonium formate buffer; and "HRMS" is high resolution mass spectrometry.

Example 1

N-5,6,9,10,11,12-HEXAHYDRO-4H,8H-CYCLO-HEPTA[4,5]PYRROLO[3,2,1-IJ]QUINOLIN-2-YL-3,3-DIMETHYLBUTANAMIDE

Step 1. Preparation of 5,6,9,10,11,12-hexahydro-4H, 8H-cyclohepta[4,5]pyrrolo[3,2,1-ij]quinoline

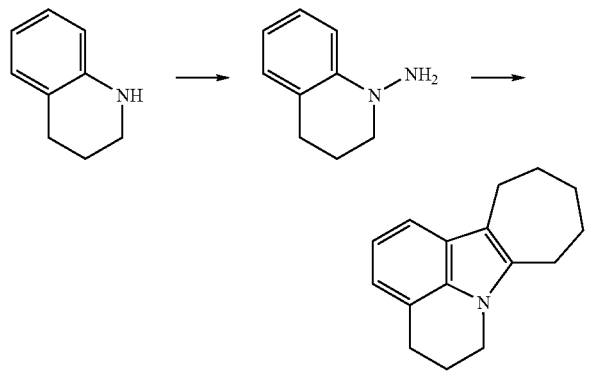

A solution of sodium nitrite (12 g, 180 mmol) in water (25 mL) was added dropwise to a cooled (~15° C.) biphasic solution of 1,2,3,4-tetrahydroquinoline (20 g, 150 mmol) in ether (120 mL), conc. HCl (30 mL), and water (70 mL). The internal reaction temperature was maintained at ~15° C. during the addition and then allowed to warm to ambient temperature with stirring over 1 hour. The reaction mixture was extracted with ether, dried over MgSO₄, and concentrated. The crude product was dissolved in water (150 mL) and acetic acid (150 mL) and zinc dust was slowly added so that the temperature did not rise above 40° C. After complete addition, the reaction mixture was stirred for an additional 30 minutes and then filtered. The filtrate was treated with 50% aqueous NaOH until basic, and then extracted with ethyl acetate, dried over MgSO₄, and concentrated to provide 19 g of a dark oil which was used without further purification. Cycloheptanone (13 mL, 110 mmol) was added to the crude hydrazine (19 g) in water (90 mL). Concentrated sulfuric acid (10 mL) was added dropwise to the reaction mixture and the resulting mixture was heated to reflux overnight. After allowing the reaction mixture to cool to ambient temperature, the mixture was poured into ice water. The precipitate was collected by filtration and purified by flash column chromatography (elution with 10% ethyl acetate-hexane) to provide 6.5 g of 5,6,9,10,11,12-hexahydro-4H,8H-cyclohepta[4,5]pyrrolo[3,2,1-ij]quinoline. MS (ESI) m/z 226.

Step 2. Preparation of 2-nitro-5,6,9,10,11,12-hexahydro-4H,8H-cyclohepta[4,5]pyrrolo[3,2,1-ij]quinoline

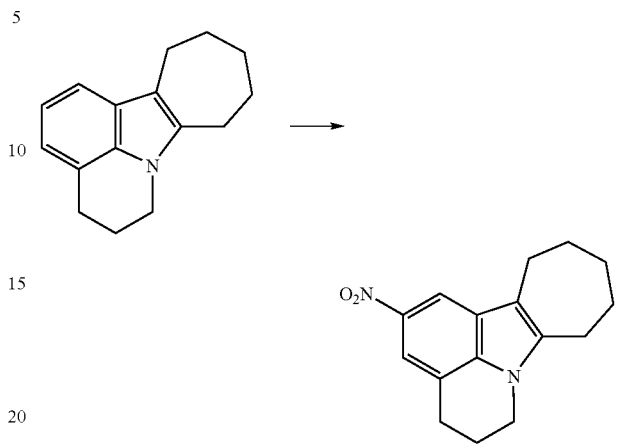

Following the procedure of Block et al. (*J. Med. Chem.* 2002, 45, 3509), 5,6,9,10,11,12-hexahydro-4H,8H-cyclohepta[4,5]pyrrolo[3,2,1-ij]quinoline (1 g, 4.4 mmol) was stirred in concentrated sulfuric acid (12 mL) at 0° C. for 30 min and then KNO₃ (0.45 g, 4.4 mmol) was introduced in portions. The reaction mixture was stirred for 2 hours at 0° C. and was then poured into ice water and extracted with ethyl acetate. The combined organic extracts were dried over MgSO₄ and concentrated to give 0.95 g of 2-nitro-5,6,9,10,11,12-hexahydro-4H,8H-cyclohepta[4,5]pyrrolo[3,2,1-ij]quinoline as a brown solid. MS (ESI) m/z 271

Step 3. Preparation of 5,6,9,10,11,12-hexahydro-4H, 8H-cyclohepta[4,5]pyrrolo[3,2,1-ij]quinolin-2-amine

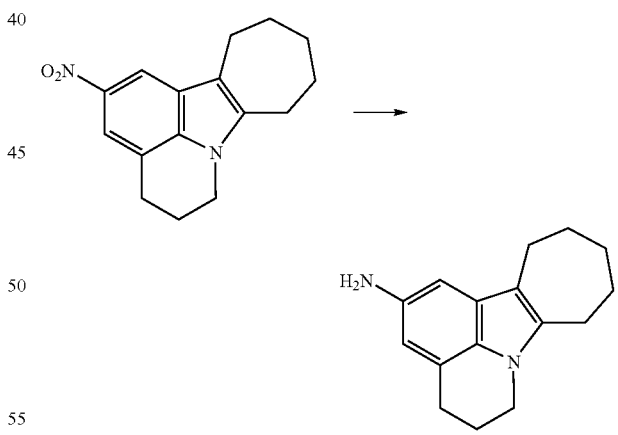

A mixture of 2-nitro-5,6,9,10,11,12-hexahydro-4H,8H-cyclohepta[4,5]pyrrolo[3,2,1-ij]quinoline (0.30 g, 11 mmol) and 5% palladium on carbon (0.10 g) in ethanol (35 mL) was shaken on a Parr hydrogenator under an atmosphere of hydrogen (45 PSI) for 48 h. The reaction mixture was filtered through Celite® and the filter bed was washed with ethanol. The filtrate was concentrated to provide 0.27 g of 5,6,9,10, 11,12-hexahydro-4H,8H-cyclohepta[4,5]pyrrolo[3,2,1-ij]quinolin-2-amine.

MS (ES) m/z 241.1

Step 3b. Preparation of 5,6,9,10,11,12-hexahydro-4H,8H-cyclohepta[4,5]pyrrolo[3,2,1-ij]quinolin-2-amine (Alternative synthesis)

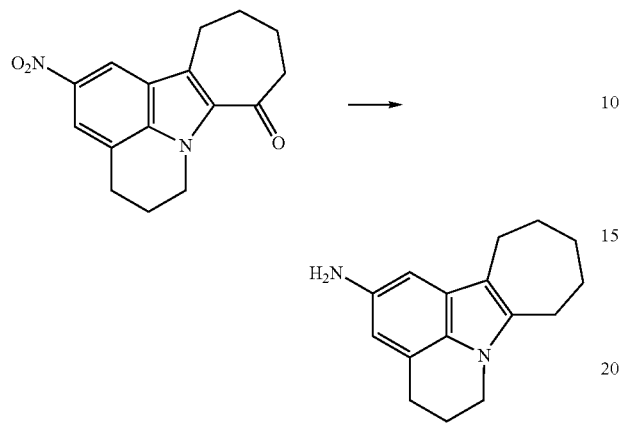

A solution of 2-nitro-8-oxo-5,6,9,10,11,12-hexahydro-4H,8H-cyclohepta[4,5]pyrrolo[3,2,1-ij]quinoline (0.17 g, 0.60 mmol; prepared in Example 23, Step 1) in dioxane (5 mL) is added dropwise to a refluxing slurry of LiAlH$_4$ (0.24 g, 6 mmol) in dioxane (20 mL). The reaction mixture was refluxed overnight. After cooling to ambient temperature, the mixture was poured onto ice water and extracted with ethyl acetate. The combined organic extracts were dried over MgSO$_4$ and concentrated to give 0.11 g of 5,6,9,10,11,12-hexahydro-4H,8H-cyclohepta[4,5]pyrrolo[3,2,1-ij]quinolin-2-amine.

Step 4. Preparation of N-5,6,9,10,11,12-hexahydro-4H,8H-cyclohepta[4,5]pyrrolo[3,2,1-ij]quinolin-2-yl-3,3-dimethylbutanamide

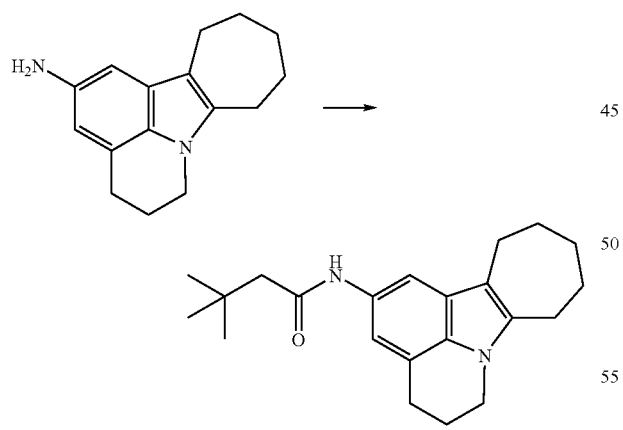

A mixture of 5,6,9,10,11,12-hexahydro-4H,8H-cyclohepta[4,5]pyrrolo[3,2,1-ij]quinolin-2-amine (0.27 g, 1.1 mmol), t-butylacetyl chloride (0.18 mL, 1.3 mmol) and poly-(4-vinylpyridine) (700 mg) in dichloromethane (18 mL) was stirred at room temperature overnight. The resin was removed by filtration and washed with dichloromethane. The filtrate was concentrated and the product was purified by flash column chromatography (elution with 30% ethyl acetate-hexane) to provide 0.20 g of N-5,6,9,10,11,12-hexahydro-4H,8H-cyclohepta[4,5]pyrrolo[3,2,1-ij]quinolin-2-yl-3,3-dimethylbutanamide as a white solid. MS (ESI) m/z 339.

Example 2

N-5,6,9,10,11,12-HEXAHYDRO-4H,8H-CYCLO-HEPTA[4,5]PYRROLO[3,2,1-IJ]QUINOLIN-2-YL-2,2-DIMETHYLPROPANAMIDE

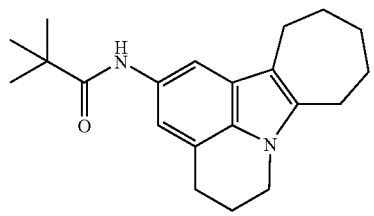

Following the procedure of Example 1, Step 4, 5,6,9,10,11,12-hexahydro-4H,8H-cyclohepta[4,5]pyrrolo[3,2,1-ij]quinolin-2-amine (0.12 g, 0.50 mmol), trimethylacetyl chloride (0.065 mL, 0.52 mmol) and poly-(4-vinylpyridine) (700 mg) in dichloromethane (10 mL) provided 0.11 g of N-5,6,9,10,11,12-hexahydro-4H,8H-cyclohepta[4,5]pyrrolo[3,2,1-ij]quinolin-2-yl-2,2-dimethylpropanamide. MS (ESI) m/z 325; HPLC purity major: no impurities detected at 210-370 nm window; 99.5% at 246 nm (max. abs), RT=10.7 (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{21}H_{28}N_2O+H^+$, 325.22744; found (ESI, [M+H]$^+$), 325.2271.

Example 3

N-5,6,9,10,11,12-HEXAHYDRO-4H,8H-CYCLO-HEPTA[4,5]PYRROLO[3,2,1-IJ]QUINOLIN-2-YLHEXANAMIDE

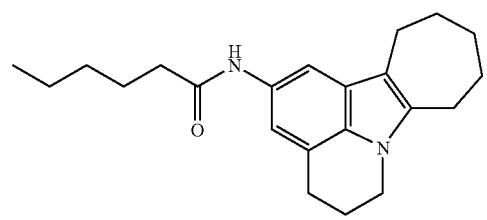

Following the procedure in Example 1, Step 4, 5,6,9,10,11,12-hexahydro-4H,8H-cyclohepta[4,5]pyrrolo[3,2,1-ij]quinolin-2-amine (0.12 g, 0.50 mmol), hexanoyl chloride (0.072 mL, 0.52 mmol) and poly-(4-vinylpyridine) (700 mg) in dichloromethane (10 mL) provided 0.14 g of N-5,6,9,10,11,12-hexahydro-4H,8H-cyclohepta[4,5]pyrrolo[3,2,1-ij]quinolin-2-ylhexanamide. MS (ESI) m/z 339;

HPLC purity major=no impurities detected at 210-370 nm window; 99.5% at 250 nm (max. abs), RT=11.2 (Xterra RP18, 3.5 u, 150×4.6 mm column,

Example 4

N-5,6,9,10,11,12-HEXAHYDRO-4H,8H-CYCLO-HEPTA[4,5]PYRROLO[3,2,1-IJ]QUINOLIN-2-YL-3-PHENYLPROPANAMIDE

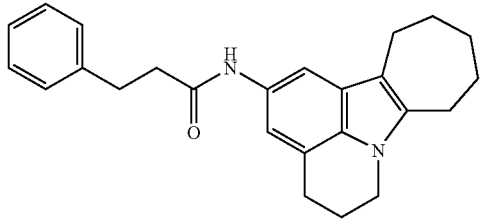

Following the procedure of Example 1, Step 4, 5,6,9,10,11,12-hexahydro-4H,8H-cyclohepta[4,5]pyrrolo[3,2,1-ij]quinolin-2-amine (0.12 g, 0.50 mmol), hydrocinnamoyl chloride (0.078 mL, 0.52 mmol) and poly-(4-vinylpyridine) (700 mg) in dichloromethane (10 mL) provided 0.13 g of N-5,6,9,10,11,12-hexahydro-4H,8H-cyclohepta[4,5]pyrrolo[3,2,1-ij]quinolin-2-yl-3-phenylpropanamide. MS (ESI) m/z 373; HPLC purity major: no impurities detected at 210-370 nm window; 99.5% at 252 nm (max. abs), RT=11.0 (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{25}H_{28}N_2O+H^+$, 373.22744; found (ESI, [M+H]$^+$), 373.2287.

Example 5

N-5,6,9,10,11,12-HEXAHYDRO-4H,8H-CYCLO-HEPTA[4,5]PYRROLO[3,2,1-IJ]QUINOLIN-2-YLTHIOPHENE-2-CARBOXAMIDE

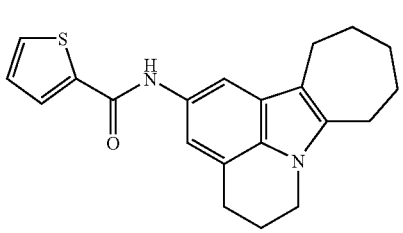

Following the procedure of Example 1, Step 4, 5,6,9,10,11,12-hexahydro-4H,8H-cyclohepta[4,5]pyrrolo[3,2,1-ij]quinolin-2-amine (0.12 g, 0.50 mmol), 2-thiophenecarbonyl chloride (0.056 mL, 0.52 mmol) and poly-(4-vinylpyridine) (700 mg) in dichloromethane (10 mL) provided 0.10 g of N-5,6,9,10,11,12-hexahydro-4H,8H-cyclohepta[4,5]pyrrolo[3,2,1-ij]quinolin-2-ylthiophene-2-carboxamide. MS (ESI) m/z 351; HPLC purity major: no impurities detected at 210-370 nm window; 98.7% at 240 nm (max. abs), RT=10.9 (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{21}H_{22}N_2OS+H^+$, 351.15256; found (ESI, [M+H]$^+$), 351.1516.

Example 6

N-5,6,9,10,11,12-HEXAHYDRO-4H,8H-CYCLO-HEPTA[4,5]PYRROLO[3,2,1-IJ]QUINOLIN-2-YL-3-METHYLBUTANAMIDE

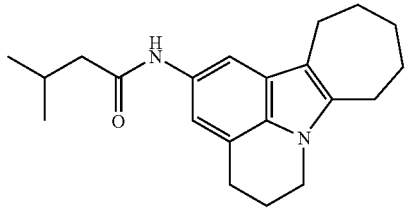

Following the procedure of Example 1, Step 4, 5,6,9,10,11,12-hexahydro-4H,8H-cyclohepta[4,5]pyrrolo[3,2,1-ij]quinolin-2-amine (0.10 g, 0.42 mmol), isovaleryl chloride (0.051 mL, 0.42 mmol) and poly-(4-vinylpyridine) (600 mg) in dichloroethane (15 mL) provided 0.09 g of N-5,6,9,10,11,12-hexahydro-4H,8H-cyclohepta[4,5]pyrrolo[3,2,1-ij]quinolin-2-yl-3-methylbutanamide. MS (ES) m/z 325.2; HPLC purity 100% at 210-370 nm, 10.8 min.; 99.4% at 252 nm, 10.8 min. (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{21}H_{28}N_2O+H^+$, 325.22744; found (ESI, [M+H]$^+$), 325.2269.

Example 7

N-5,6,9,10,11,12-HEXAHYDRO-4H,8H-CYCLO-HEPTA[4,5]PYRROLO[3,2,1-IJ]QUINOLIN-2-YLPROPANAMIDE

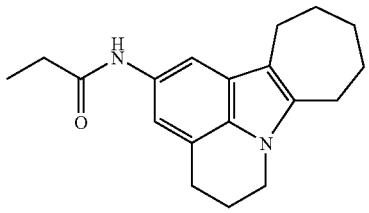

Following the procedure of Example 1, Step 4, 5,6,9,10,11,12-hexahydro-4H,8H-cyclohepta[4,5]pyrrolo[3,2,1-ij]quinolin-2-amine (0.10 g, 0.42 mmol), propionyl chloride (0.036 mL, 0.42 mmol) and poly-(4-vinylpyridine) (600 mg) in dichloroethane (15 mL) provided 49 mg of N-5,6,9,10,11,12-hexahydro-4H,8H-cyclohepta[4,5]pyrrolo[3,2,1-ij]quinolin-2-ylpropanamide (49 mg). MS (ES) m/z 297.2; HPLC purity 100% at 210-370 nm, 10.0 min.; 99.3% at 250 nm, 10.0 min. (Xterra RP18, 3.5 u, 150×4.6 mm column, 1.2 mL/min, 85/15-5/95 ((Ammon. Form. Buff. pH=3.5/ACN and MeOH) for 10 min, hold 4 min); HRMS: calcd for $C_{19}H_{24}N_2O+H^+$, 297.19614; found (ESI, [M+H]$^+$), 297.1973.

1.2 mL/min, 85/15-5/95 (Ammon. Form. Buff. pH=3.5/ACN and MeOH) for 10 min, hold 4 min); HRMS: calcd for $C_{22}H_{30}N_2O+H^+$, 339.24309; found (ESI, [M+H]$^+$), 339.2436.

Example 8

N-5,6,9,10,11,12-HEXAHYDRO-4H,8H-CYCLO-HEPTA[4,5]PYRROLO[3,2,1-IJ]QUINOLIN-2-YLCYCLOHEXANECARBOXAMIDE

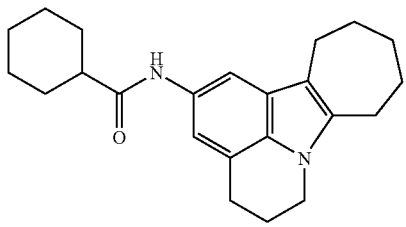

Following the procedure of Example 1, Step 4, 5,6,9,10,11,12-hexahydro-4H,8H-cyclohepta[4,5]pyrrolo[3,2,1-ij]quinolin-2-amine (0.10 g, 0.42 mmol), cyclohexanecarbonyl chloride (0.056 mL, 0.42 mmol) and poly-(4-vinylpyridine) (600 mg) in dichloroethane (15 mL) provided 79 mg of N-5,6,9,10,11,12-hexahydro-4H,8H-cyclohepta[4,5]pyrrolo[3,2,1-ij]quinolin-2-ylcyclohexanecarboxamide. MS (ES) m/z 351.2; HPLC purity 100% at 210-370 nm, 11.3 min.; 99.5% at 252 nm, 11.3 min. (Xterra RP18, 3.5 u, 150×4.6 mm column, 1.2 mL/min, 85/15-5/95 ((Ammon. Form. Buff. pH=3.5/ACN and MeOH) for 10 min, hold 4 min); HRMS: calcd for $C_{23}H_{30}N_2O+H^+$, 351.24309; found (ESI, [M+H]$^+$), 351.2443.

Example 9

N-5,6,9,10,11,12-HEXAHYDRO-4H,8H-CYCLO-HEPTA[4,5]PYRROLO[3,2,1-IJ]QUINOLIN-2-YLPENTANAMIDE

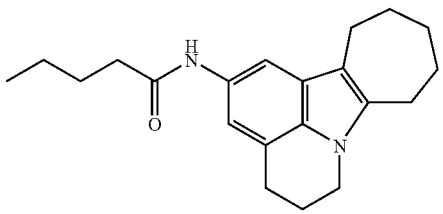

Following the procedure of Example 1, Step 4, 5,6,9,10,11,12-hexahydro-4H,8H-cyclohepta[4,5]pyrrolo[3,2,1-ij]quinolin-2-amine (0.10 g, 0.42 mmol), valeryl chloride (0.049 mL, 0.42 mmol) and poly-(4-vinylpyridine) (600 mg) in dichloroethane (15 mL) provided N-5,6,9,10,11,12-hexahydro-4H,8H-cyclohepta[4,5]pyrrolo[3,2,1-ij]quinolin-2-ylpentanamide (45 mg). MS (ESI) m/z 325; HPLC purity 100% at 210-370 nm, 10.8 min.; 98.4% at 250 nm, 10.8 min.; (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{21}H_{28}N_2O+H^+$, 325.22744; found (ESI, [M+H]$^+$), 325.2265.

Example 10

N-4,5,8,9,10,11-HEXAHYDRO-7H-CYCLOHEPTA[B]PYRROLO[3,2,1-HI]INDOL-2-YL-3,3-DIMETHYLBUTANAMIDE

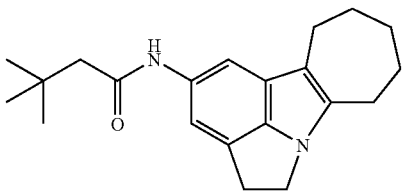

Step 1. Preparation of 4,5,8,9,10,11-hexahydro-7H-cyclohepta[b]pyrrolo[3,2,1-hi]indole

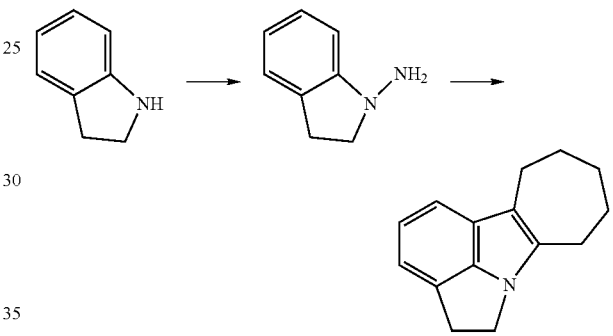

Following the procedure of Example 1, step 1, indoline (20 g, 170 mmol), sodium nitrite (14 g, 200 mmol), concentrated hydrochloric acid (30 mL) in water (70 mL) and ether (120 mL) provided 1-nitroindoline (31 g), which was reduced with zinc dust (~50 g) in acetic acid (500 mL) to provide 1-aminoindoline (29 g). A mixture of 1-aminoindoline (17 g, 130 mmol), cycloheptanone (15 mL, 130 mmol), and concentrated sulfuric acid (20 mL) in water (180 mL) provided 8.2 g of 4,5,8,9,10,11-hexahydro-7H-cyclohepta[b]pyrrolo[3,2,1-hi]indole. MS (ESI) m/z 212.

Step 2. Preparation of 2-nitro-4,5,8,9,10,11-hexahydro-7H-cyclohepta[b]pyrrolo[3,2,1-hi]indole

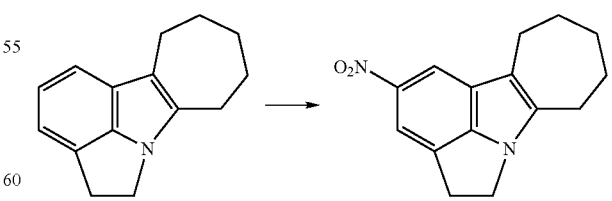

Following the procedure of Example 1, step 2, 4,5,8,9,10,11-hexahydro-7H-cyclohepta[b]pyrrolo[3,2,1-hi]indole (7.5 g, 35 mmol) and potassium nitrate (3.6 g, 35 mmol) in concentrated sulfuric acid (100 mL) provided 2-nitro-4,5,8,9,10,11-hexahydro-7H-cyclohepta[b]pyrrolo[3,2,1-hi]indole.

Step 3. Preparation of 4,5,8,9,10,11-hexahydro-7H-cyclohepta[b]pyrrolo[3,2,1-hi]indol-2-amine

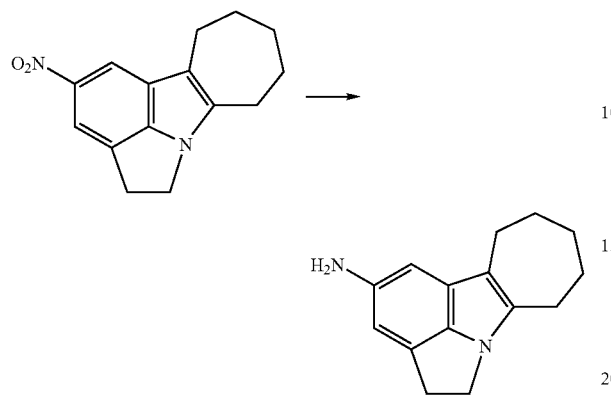

Following the procedure of Example 1, step 3, 2-nitro-4,5, 8,9,10,11-hexahydro-7H-cyclohepta[b]pyrrolo[3,2,1-hi]indole was hydrogenated over 5% palladium on carbon to provide 4,5,8,9,10,11-hexahydro-7H-cyclohepta[b]pyrrolo[3,2, 1-hi]indole-2-amine which was used for the coupling reactions.

Step 4. N-4,5,8,9,10,11-hexahydro-7H-cyclohepta[b]pyrrolo[3,2,1-hi]indol-2-yl-3,3-dimethylbutanamide

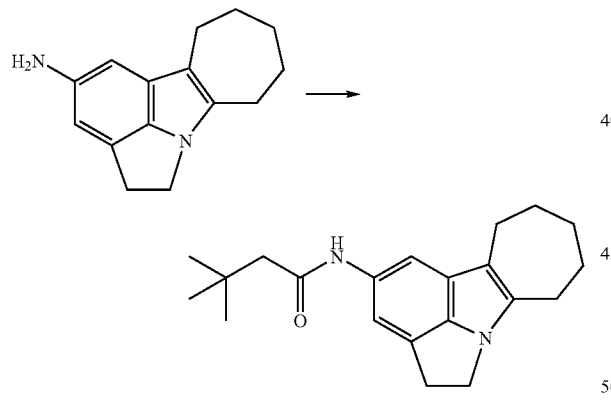

As in Example 1, Step 4, 4,5,8,9,10,11-hexahydro-7H-cyclohepta[b]pyrrolo[3,2,1-hi]indole-2-amine (0.10 g, 0.44 mmol), t-butylacetyl chloride (0.061 mL, 0.44 mmol) and poly-(4-vinylpyridine) (600 mg) in dichloroethane (15 mL) provided 35 mg of N-4,5,8,9,10,11-hexahydro-7H-cyclohepta[b]pyrrolo[3,2,1-hi]indol-2-yl-3,3-dimethylbutanamide. MS (ES) m/z 325.2; HPLC purity 100% at 210-370 nm, 10.8 min.; 100% at 250 nm, 10.8 min. (Xterra RP18, 3.5 u, 150×4.6 mm column, 1.2 mL/min, 85/15-5/95 ((Ammon. Form. Buff. pH=3.5/ACN and MeOH) for 10 min, hold 4 min); HRMS: calcd for $C_{21}H_{28}N_2O+H^+$, 325.22744; found (ESI, [M+H]$^+$), 325.2277.

Example 11

N-4,5,8,9,10,11-HEXAHYDRO-7H-CYCLOHEPTA[B]PYRROLO[3,2,1-HI]INDOL-2-YLACETAMIDE

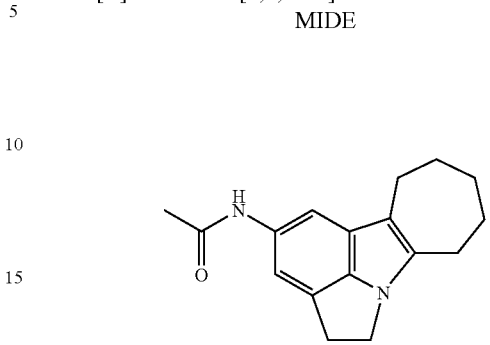

Following the procedure of Example 1, Step 4, 4,5,8,9,10, 11-hexahydro-7H-cyclohepta[b]pyrrolo[3,2,1-hi]indole-2-amine (0.10 g, 0.44 mmol), acetic anhydride (0.042 mL, 0.44 mmol) and poly-(4-vinylpyridine) (600 mg) in dichloroethane (15 mL) provided 28 mg of N-4,5,8,9,10,11-hexahydro-7H-cyclohepta[b]pyrrolo[3,2,1-hi]indol-2-ylacetamide. MS m/z 269; HPLC purity 100% at 210-370 nm, 9.2 min.; 98.7% at 248 nm, 9.2 min. (Xterra RP18, 3.5 u, 150×4.6 mm column, 1.2 mL/min, 85/15-5/95 ((Ammon. Form. Buff. pH=3.5/ACN and MeOH) for 10 min, hold 4 min); HRMS: calcd for $C_{17}H_{20}N_2O+H^+$, 269.16484; found (ESI, [M+H]$^+$), 269.1651.

Example 12

N-4,5,8,9,10,11-HEXAHYDRO-7H-CYCLOHEPTA[B]PYRROLO[3,2,1-HI]INDOL-2-YLPENTANAMIDE

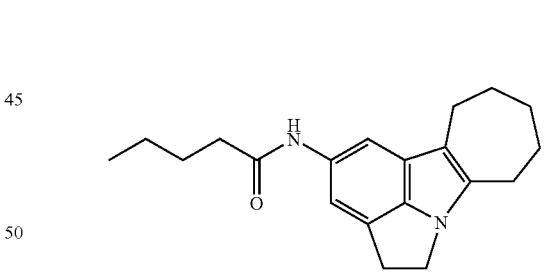

Following the procedure of Example 1, Step 4, 4,5,8,9,10, 11-hexahydro-7H-cyclohepta[b]pyrrolo[3,2,1-hi]indole-2-amine (0.13 g, 0.57 mmol), valeryl chloride (0.068 mL, 0.57 mmol) and poly-(4-vinylpyridine) (600 mg) in dichloromethane (15 mL) provided N-4,5,8,9,10,11-hexahydro-7H-cyclohepta[b]pyrrolo[3,2,1-hi]indol-2-ylpentanamide (35 mg). MS (ESI) m/z 311; HPLC purity 100% at 210-370 nm, 10.6 min.; 100% at 250 nm, 10.6 min. (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{20}H_{26}N_2O+H^+$, 311.21179; found (ESI, [M+H]$^+$), 311.2118.

Example 13

N-4,5,8,9,10,11-HEXAHYDRO-7H-CYCLOHEPTA[B]PYRROLO[3,2,1-HI]INDOL-2-YL-2-PHENYLACETAMIDE

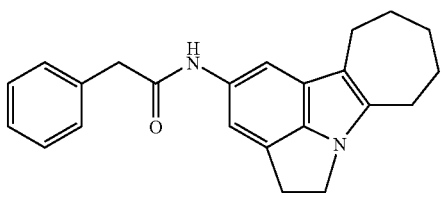

Following the procedure of Example 1, Step 4, 4,5,8,9,10,11-hexahydro-7H-cyclohepta[b]pyrrolo[3,2,1-hi]indole-2-amine (0.10 g, 0.44 mmol), phenylacetyl chloride (0.058 mL, 0.44 mmol) and poly-(4-vinylpyridine) (600 mg) in dichloroethane (15 mL) provided N-4,5,8,9,10,11-hexahydro-7H-cyclohepta[b]pyrrolo[3,2,1-hi]indol-2-yl-2-phenylacetamide (10 mg). MS (ESI) m/z 345; HPLC purity 100% at 210-370 nm, 10.6 min.; 100% at 252 nm, 10.6 min. (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{23}H_{24}N_2O+H^+$, 345.19614; found (ESI, [M+H]$^+$), 345.1959.

Example 14

N-4,5,8,9,10,11-HEXAHYDRO-7H-CYCLOHEPTA[B]PYRROLO[3,2,1-HI]INDOL-2-YL-3-METHYLBUTANAMIDE

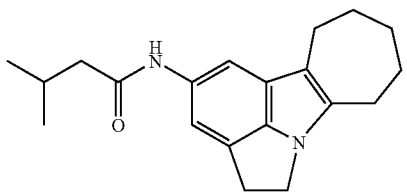

Following the procedure of Example 1, Step 4, 4,5,8,9,10,11-hexahydro-7H-cyclohepta[b]pyrrolo[3,2,1-hi]indole-2-amine (0.10 g, 0.44 mmol), isovaleryl chloride (0.054 mL, 0.44 mmol) and poly-(4-vinylpyridine) (600 mg) in dichloroethane (15 mL) provided N-4,5,8,9,10,11-hexahydro-7H-cyclohepta[b]pyrrolo[3,2,1-hi]indol-2-yl-3-methylbutanamide (27 mg). MS (ESI) m/z 311; HPLC purity 98.5% at 210-370 nm, 10.5 min.; 99.5% at 250 nm, 10.5 min. (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{20}H_{26}N_2O+H^+$, 311.21179; found (ESI, [M+H]$^+$), 311.2120.

Example 15

3-CYCLOPENTYL-N-4,5,8,9,10,11-HEXAHYDRO-7H-CYCLOHEPTA[B]PYRROLO[3,2,1-HI]INDOL-2-YLPROPANAMIDE

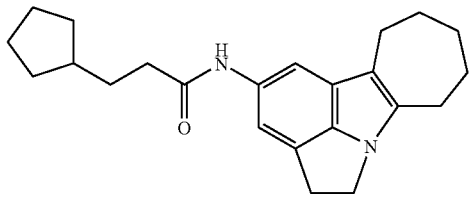

Following the procedure of Example 1, Step 4, 4,5,8,9,10,11-hexahydro-7H-cyclohepta[b]pyrrolo[3,2,1-hi]indole-2-amine (0.10 g, 0.44 mmol), 3-cyclopentylpropionyl chloride (0.068 mL, 0.44 mmol) and poly-(4-vinylpyridine) (600 mg) in dichloroethane (15 mL) provided 3-cyclopentyl-N-4,5,8,9,10,11-hexahydro-7H-cyclohepta[b]pyrrolo[3,2,1-hi]indol-2-ylpropanamide (10 mg). MS (ESI) m/z 351; HPLC purity 100% at 210-370 nm, 11.4 min.; 100% at 250 nm, 11.4 min. (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{23}H_{30}N_2O+H^+$, 351.24309; found (ESI, [M+H]$^+$), 351.2423.

Example 16

N-5,6,8,9,10,11-HEXAHYDRO-4H-PYRIDO[3,2,1-JK]CARBAZOL-2-YL-3,3-DIMETHYLBUTANAMIDE

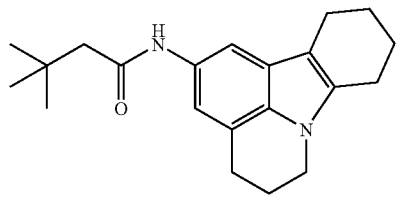

Step 1. Preparation of 3,3-dimethyl-N-quinolin-6-ylbutanamide

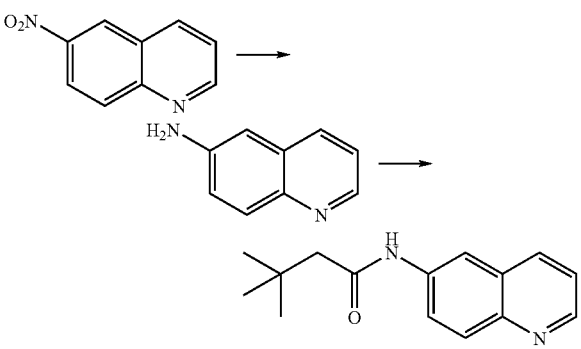

Following the procedure of Example 1, Step 3, 6-nitroquinoline (2.5 g) and 5% palladium on carbon (0.10 g) in ethanol (40 mL) was hydrogenated to give 6-aminoquinoline (2.2 g). A mixture of 6-aminoquinoline (2.2 g, 15 mmol), t-butylacetyl chloride (2.2 mL, 16 mmol), and pyridine (2.5 mL, 31 mmol) in dichloromethane (40 mL) was then stirred at ambient temperature for 4 h and then extracted with 1 N HCl. The acidic layer was separated and treated with 50% NaOH until basic. The basic phase was extracted with dichloromethane. The combined extracts were dried (MgSO$_4$) and concentrated. The crude material was triturated with hexane and the solid was collected by filtration to provide 3,3-dimethyl-N-quinolin-6-ylbutanamide (3.0 g). MS (ES) m/z 241.1.

Step 2. Preparation of 3,3-dimethyl-N-1,2,3,4-tetrahydroquinolin-6-ylbutanamide

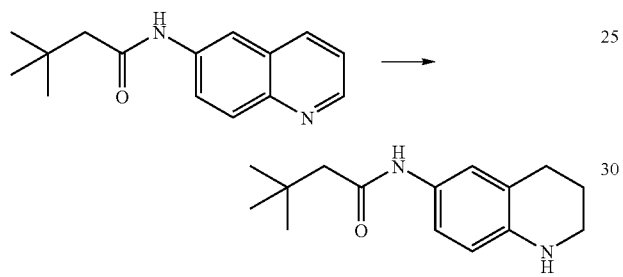

A mixture of 3,3-dimethyl-N-quinolin-6-ylbutanamide (2.4 g), 5% platinum on carbon (0.15 g), trifluoroacetic acid (2.0 mL) and ethanol (50 mL) was hydrogenated at 45 PSI on a Parr shaker for 48 h. The reaction mixture was filtered through Celite® and the filtrate was concentrated. The crude solid was dissolved in ethyl acetate and washed carefully with saturated aqueous sodium bicarbonate. The organic layer was dried (MgSO$_4$) and concentrated. The resulting oil was dissolved in ether and 4 N HCl was added. The solid was collected by filtration to yield 3,3-dimethyl-N-1,2,3,4-tetrahydroquinolin-6-ylbutanamide (2.1 g) as its HCl salt. MS (ES) m/z 247.2.

Step 3. Preparation of N-5,6,8,9,10,11-hexahydro-4H-pyrido[3,2,1-jk]carbazol-2-yl-3,3-dimethylbutanamide

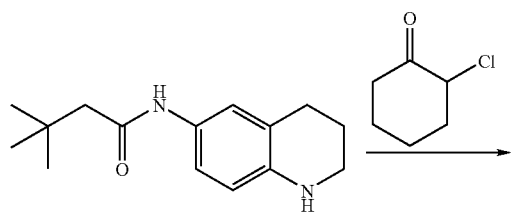

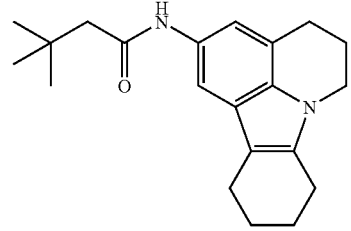

A mixture of 3,3-dimethyl-N-1,2,3,4-tetrahydroquinolin-6-ylbutanamide hydrochloride (50 mg, 0.18 mmol) and 2-chlorocyclohexanone (28 mg, 0.21 mmol) in ethanol (2.5 mL) was heated in a microwave to 150° C. for 50 min. The reaction mixture was concentrated and the crude material was purified by flash column chromatography (elution with 20% ethyl acetate-hexane) to provide N-5,6,8,9,10,11-hexahydro-4H-pyrido[3,2,1-jk]carbazol-2-yl-3,3-dimethylbutanamide (19 mg). MS (ESI) m/z 325; HPLC purity major: no impurities are detected at 210-370 nm window; and no impurities are detected at 252 nm (max. abs), RT=10.8 (Xterra RP18, 3.5 u, 150×4.6 mm column, 1.2 mL/min, 85/15-5/95 (Ammon. Form. Buff. pH=3.5/ACN and MeOH) for 10 min, hold 4 min).

Example 17

N-5,6,8,9,10,11-HEXAHYDRO-4H-PYRIDO[3,2,1-JK]CARBAZOL-2-YLHEXANAMIDE

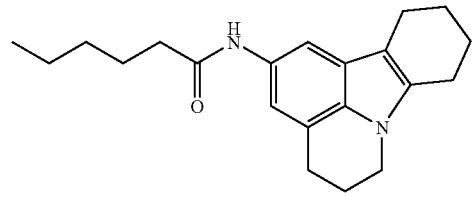

Step 1. Preparation of 5,6,8,9,10,11-hexahydro-4H-pyrido[3,2,1-jk]carbazole

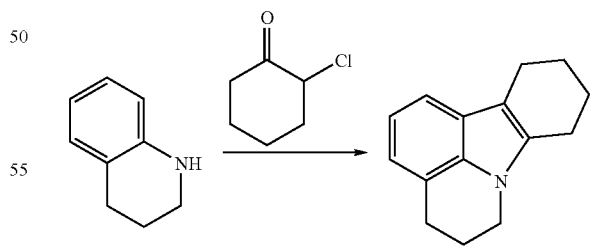

A mixture of 1,2,3,4-tetrahydroquinoline (4.0 mL, 32 mmol), 2-chlorocyclohexanone (3.6 mL, 32 mmol) and pyridine (3.0 mL, 38 mmol) in 2-methoxyethanol (80 mL) was heated to 120° C. for 48 h and was then concentrated. The black gummy residue was extracted into ethyl acetate and washed with 2 N HCl. The organic layer was dried (MgSO$_4$) and concentrated. The material was purified by flash column chromatography (elution with 5% ethyl acetate-hexanes) to provide a clear oil which was dissolved in hexane. Upon cooling the solution to −78° C. a precipitate formed. The precipitate was collected to provide 5,6,8,9,10,11-hexahydro-4H-pyrido[3,2,1-jk]carbazole. MS (ES) m/z 212.1.

Step 2. Preparation of 2-nitro-5,6,8,9,10,11-hexahydro-4H-pyrido[3,2,1-jk]carbazole

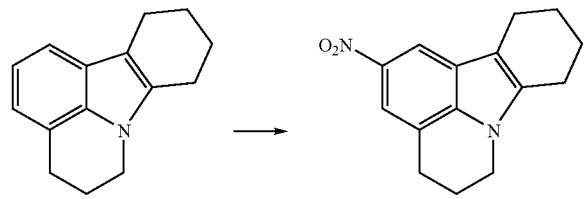

Following the procedure of Example 1, step 2, 5,6,8,9,10,11-hexahydro-4H-pyrido[3,2,1-jk]carbazole (1.7 g, 8.0 mmol) and potassium nitrate (0.80 g, 8.0 mmol) in concentrated sulfuric acid (20 mL) provided 2-nitro-5,6,8,9,10,11-hexahydro-4H-pyrido[3,2,1-jk]carbazole. MS (ES) m/z 257.1.

Step 3. Preparation of 5,6,8,9,10,11-hexahydro-4H-pyrido[3,2,1-jk]carbazol-2-amine

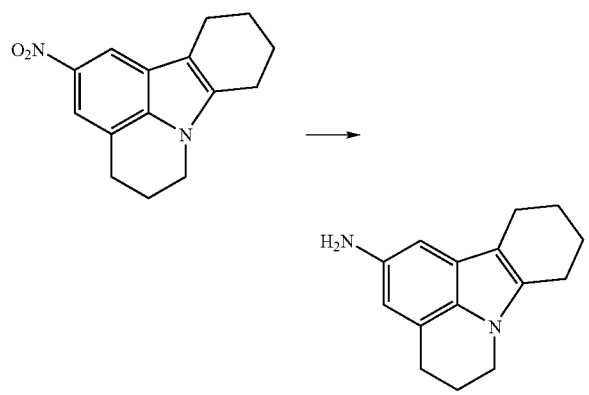

Following the procedure of Example 1, Step 3, 2-nitro-5,6,8,9,10,11-hexahydro-4H-pyrido[3,2,1-jk]carbazole (1.1 g, 4.3 mmol) and 5% palladium on carbon (0.10 g) in ethanol (70 mL) was hydrogenated to provide 5,6,8,9,10,11-hexahydro-4H-pyrido[3,2,1-jk]carbazol-2-amine.

Step 4. Preparation of N-5,6,8,9,10,11-hexahydro-4H-pyrido[3,2,1-jk]carbazol-2-yl-3,3-dimethylbutanamide

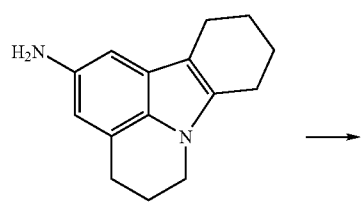

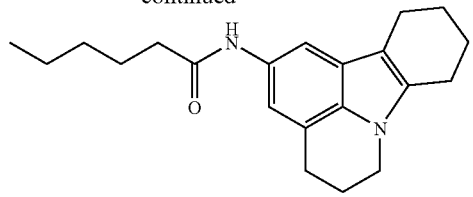

Following the procedure of Example 1, Step 4, 5,6,8,9,10,11-hexahydro-4H-pyrido[3,2,1-jk]carbazol-2-amine (0.13 g, 0.55 mmol), hexanoyl chloride (0.076 mL, 0.55 mmol) and poly-(4-vinylpyridine) (500 mg) in dichloromethane (12 mL) provided N-5,6,8,9,10,11-hexahydro-4H-pyrido[3,2,1-jk]carbazol-2-ylhexanamide (14 mg). MS (ES) m/z 325.1; HPLC purity 100% at 210-370 nm, 11.0 min.; 98.9% at 250 nm, 11.0 min. (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{21}H_{28}N_2O+H^+$, 325.22744; found (ESI, [M+H]$^+$), 325.2289.

Example 18

N-5,6,8,9,10,11-HEXAHYDRO-4H-PYRIDO[3,2,1-JK]CARBAZOL-2-YL-3-METHYLBUTANAMIDE

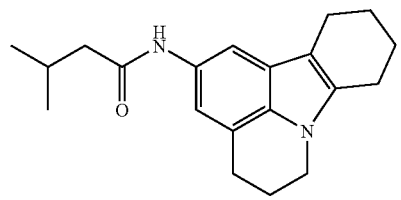

Following the procedure of Example 1, Step 4, 5,6,8,9,10,11-hexahydro-4H-pyrido[3,2,1-jk]carbazol-2-amine (0.10 g, 0.44 mmol), isovaleryl chloride (0.054 mL, 0.44 mmol) and poly-(4-vinylpyridine) (600 mg) in dichloroethane (15 mL) provided N-5,6,8,9,10,11-hexahydro-4H-pyrido[3,2,1-jk]carbazol-2-yl-3-methylbutanamide (68 mg). MS m/z 311; HPLC purity 100% at 210-370 nm, 10.5 min.; 99.4% at 250 nm, 10.5 min. (Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{20}H_{26}N_2O+H^+$, 311.21179; found (ESI, [M+H]$^+$), 311.2122.

Example 19

N-5,6,8,9,10,11-HEXAHYDRO-4H-PYRIDO[3,2,1-JK]CARBAZOL-2-YLACETAMIDE

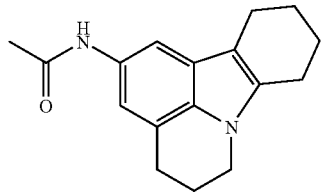

Following the procedure of Example 1, Step 4, 5,6,8,9,10,11-hexahydro-4H-pyrido[3,2,1-jk]carbazol-2-amine (0.10 g, 0.44 mmol), acetic anhydride (0.042 mL, 0.44 mmol) and poly-(4-vinylpyridine) (600 mg) in dichloroethane (15 mL)

provided N-5,6,8,9,10,11-hexahydro-4H-pyrido[3,2,1-jk]carbazol-2-ylacetamide (26 mg). MS (ESI) m/z 269; HPLC purity 99.4% at 210-370 nm, 9.1 min.; 98.4% at 248 nm, 9.1 min.; Xterra RP18, 3.5 u, 150×4.6 mm column, 1.2 mL/min, 85/15-5/95 ((Ammon. Form. Buff. pH=3.5/ACN and MeOH) for 10 min, hold 4 min); HRMS: calcd for $C_{17}H_{20}N_2O+H^+$, 269.16484; found (ESI, [M+H]$^+$), 269.1646.

Example 20

N-4,5,7,8,9,10,11,12-OCTAHYDROCYCLOOCTA[B]PYRROLO[3,2,1-HI]INDOL-2-YLHEXANAMIDE

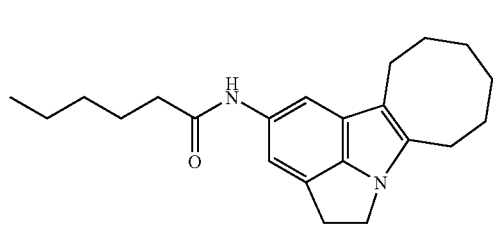

Step 1. Preparation of 4,5,7,8,9,10,11,12-octahydrocycloocta[b]pyrrolo[3,2,1-hi]indole

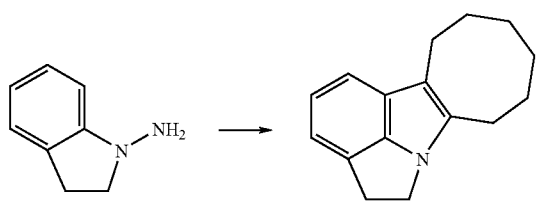

Following the procedure of Example 1, Step 1, cyclooctanone (6.9 mL, 52 mmol), 1-aminoindoline (7.0 g, 52 mmol) and concentrated sulfuric acid (10 mL) in water (90 mL) provided 4,5,7,8,9,10,11,12-octahydrocycloocta[b]pyrrolo[3,2,1-hi]indole (3.6 g). MS (ES) m/z 226.2.

Step 2. Procedure of 2-nitro-4,5,7,8,9,10,11,12-octahydrocycloocta[b]pyrrolo[3,2,1-hi]indole

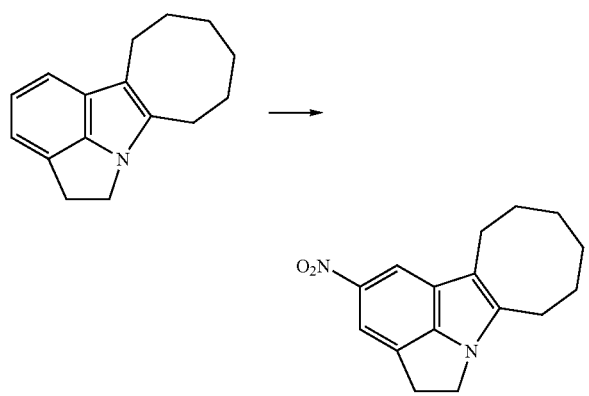

Following the procedure of Example 1 Step 2, 4,5,7,8,9,10,11,12-octahydrocycloocta[b]pyrrolo[3,2,1-hi]indole (3.2 g, 14 mmol), potassium nitrate (1.5 g, 14 mmol) and concentrated sulfuric acid (50 mL) provided 2-nitro-4,5,7,8,9,10,11,12-octahydrocycloocta[b]pyrrolo[3,2,1-hi]indole (3.0 g). MS (ES) m/z 271.2; HRMS: calcd for $C_{16}H_{18}N_2O_2+H^+$, 271.14410; found (ESI, [M+H]$^+$), 271.1437.

Step 3. 4,5,7,8,9,10,11,12-octahydrocycloocta[b]pyrrolo[3,2,1-hi]indol-2-amine

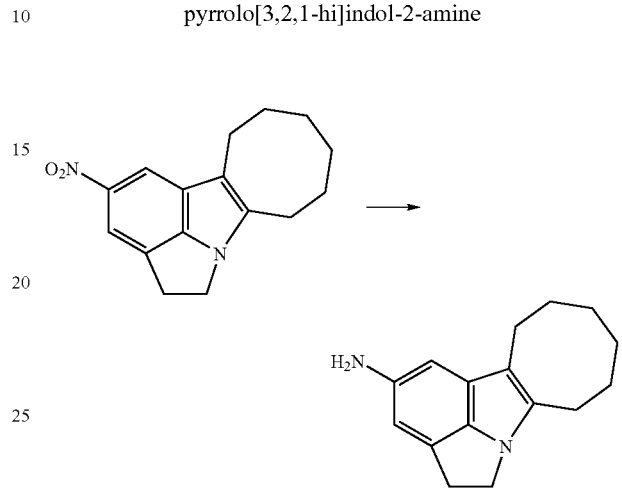

Following the procedure of Example 1, Step 3, 2-nitro-4,5,7,8,9,10,11,12-octahydrocycloocta[b]pyrrolo[3,2,1-hi]indole (2.0 g, 7.4 mmol) and 5% palladium on carbon (0.25 g) in ethanol (25 mL) was hydrogenated to provide 4,5,7,8,9,10,11,12-octahydrocycloocta[b]pyrrolo[3,2,1-hi]indol-2-amine. MS (ES) m/z 241.2; HRMS: calcd for $C_{16}H_{20}N_2+H^+$, 241.16992; found (ESI, [M+H]$^+$), 241.1693.

Step 4. N-4,5,7,8,9,10,11,12-octahydrocycloocta[b]pyrrolo[3,2,1-hi]indol-2-ylhexanamide

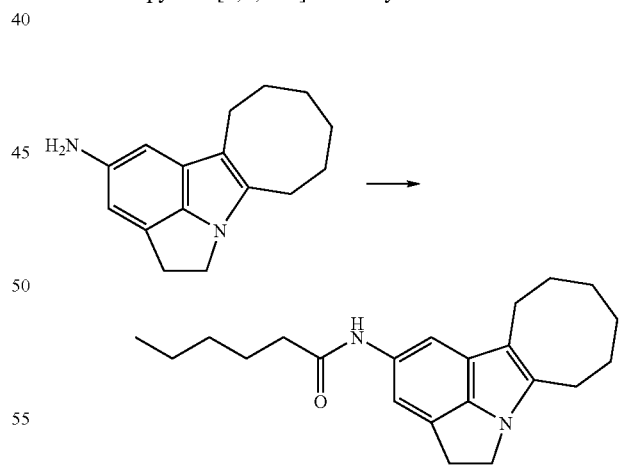

Following the procedure of Example 1, Step 4, 4,5,7,8,9,10,11,12-octahydrocycloocta[b]pyrrolo[3,2,1-hi]indol-2-amine (0.15 g, 0.54 mmol), hexanoyl chloride (0.075 mL, 0.54 mmol) and poly-(4-vinylpyridine) (500 mg) in dichloromethane (12 mL) provided N-4,5,7,8,9,10,11,12-octahydrocycloocta[b]pyrrolo[3,2,1-hi]indol-2-ylhexanamide (66 mg). MS (ES) m/z 339.2; HPLC purity 100% at 210-370 nm, 11.2 min.; 100% at 250 nm, 11.2 min. (Xterra RP18, 3.5 u, 150×4.6 mm column, 1.2 mL/min, 85/15-5/95 ((Ammon.

Form. Buff. pH=3.5/ACN and MeOH) for 10 min, hold 4 min); HRMS: calcd for $C_{22}H_{30}N_2O+H^+$, 339.24309; found (ESI, [M+H]$^+$), 339.2433.

Example 21

3,3-DIMETHYL-N-4,5,7,8,9,10,11,12-OCTAHYDROCYCLOOCTA[B]PYRROLO[3,2,1-HI]INDOL-2-YLBUTANAMIDE

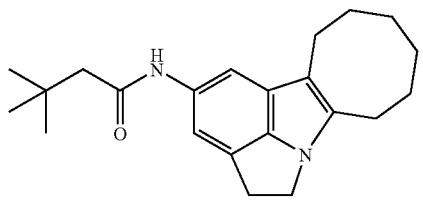

Following the procedure of Example 1, Step 4, 4,5,7,8,9,10,11,12-octahydrocycloocta[b]pyrrolo[3,2,1-hi]indol-2-amine (0.15 g, 0.54 mmol), t-butylacetyl chloride (0.063 mL, 0.54 mmol) and poly-(4-vinylpyridine) (500 mg) in dichloromethane (12 mL) provided 3,3-dimethyl-N-4,5,7,8,9,10,11,12-octahydrocycloocta[b]pyrrolo[3,2,1-hi]indol-2-ylbutanamide (67 mg). MS (ES) m/z 339.2; HPLC purity 100% at 210-370 nm, 11.1 min.; 100% at 250 nm, 11.1 min.; Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{22}H_{30}N_2O+H^+$, 339.24309; found (ESI, [M+H]$^+$), 339.2441.

Example 22

N-4,5,7,8,9,10,11,12-OCTAHYDROCYCLOOCTA[B]PYRROLO[3,2,1-HI]INDOL-2-YLHEPTANAMIDE

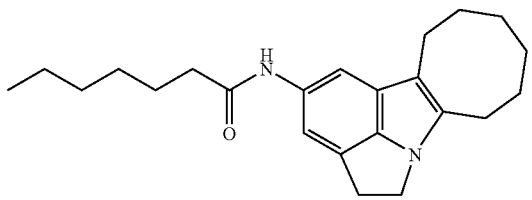

Following the procedure of Example 1, Step 4, 4,5,7,8,9,10,11,12-octahydrocycloocta[b]pyrrolo[3,2,1-hi]indol-2-amine (0.15 g, 0.54 mmol), heptanoyl chloride (0.084 mL, 0.54 mmol) and poly-(4-vinylpyridine) (500 mg) in dichloromethane (12 mL) provided N-4,5,7,8,9,10,11,12-octahydrocycloocta[b]pyrrolo[3,2,1-hi]indol-2-ylheptanamide (37 mg). MS (ESI) m/z 353; HPLC purity 100% at 210-370 nm, 11.6 min.; 100% at 250 nm, 11.6 min.; Xterra RP18, 3.5 u, 150×4.6 mm column, 1.2 mL/min, 85/15-5/95 (Ammon. Form. Buff. pH=3.5/ACN and MeOH) for 10 min, hold 4 min); HRMS: calcd for $C_{23}H_{32}N_2O+H^+$, 353.25874; found (ESI, [M+H]$^+$), 353.2575.

Example 23

3,3-DIMETHYL-N-(8-OXO-5,6,9,10,11,12-HEXAHYDRO-4H,8H-CYCLOHEPTA[4,5]PYRROLO[3,2,1-IJ]QUINOLIN-2-YL)BUTANAMIDE

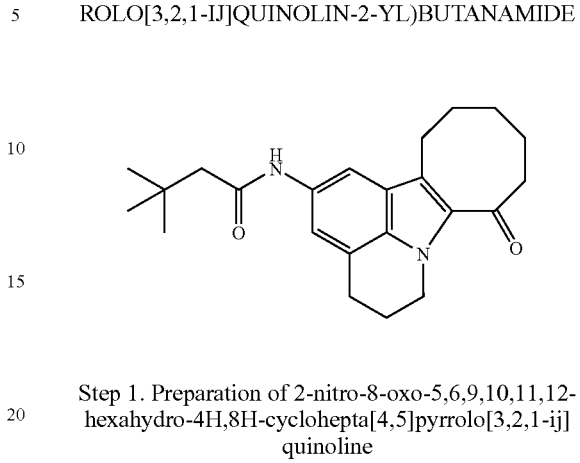

Step 1. Preparation of 2-nitro-8-oxo-5,6,9,10,11,12-hexahydro-4H,8H-cyclohepta[4,5]pyrrolo[3,2,1-ij]quinoline

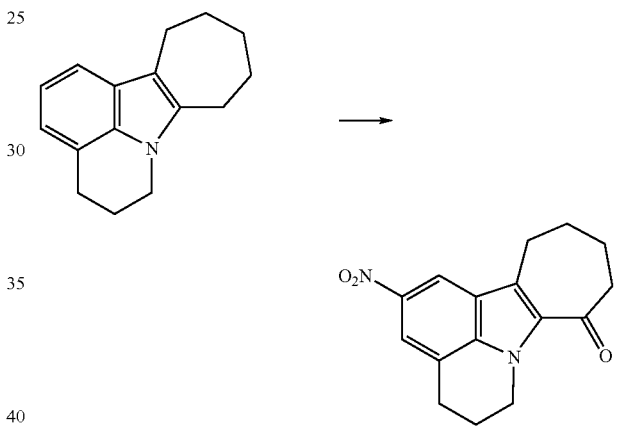

Nitric acid (1.2 mL, 22 mmol) was added dropwise to a mixture of 5,6,9,10,11,12-hexahydro-4H,8H-cyclohepta[4,5]pyrrolo[3,2,1-ij]quinoline (2.0 g, 8.9 mmol) and concentrated sulfuric acid (43 mL). The reaction mixture was stirred for 1 hour and then poured into water and extracted with ethyl acetate. The combined organic extracts were dried (MgSO$_4$) and concentrated. The crude material was purified by flash column chromatography (elution with 12% ethyl acetate-hexanes) to provide 2-nitro-8-oxo-5,6,9,10,11,12-hexahydro-4H,8H-cyclohepta[4,5]pyrrolo[3,2,1-ij]quinoline.

Step 2. Preparation of 8-oxo-5,6,9,10,11,12-hexahydro-4H,8H-cyclohepta[4,5]pyrrolo[3,2,1-ij]quinolin-2-amine

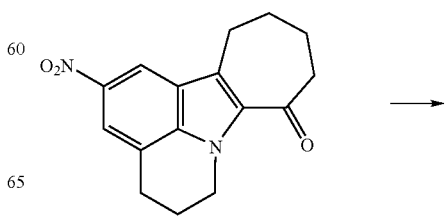

-continued

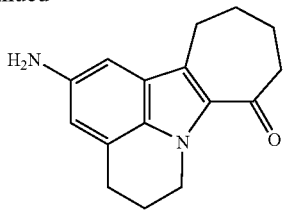

Following the procedure of Example 1, Step 3, 2-nitro-8-oxo-5,6,9,10,11,12-hexahydro-4H,8H-cyclohepta[4,5]pyrrolo[3,2,1-ij]quinoline (0.10 g, 0.37 mmol) and 5% palladium on carbon (30 mg) in ethanol (25 mL) was hydrogenated to provide 8-oxo-5,6,9,10,11,12-hexahydro-4H,8H-cyclohepta[4,5]pyrrolo[3,2,1-ij]quinolin-2-amine.

Step 3. Preparation of 3,3-dimethyl-N-(8-oxo-5,6,9,10,11,12-hexahydro-4H,8H-cyclohepta[4,5]pyrrolo[3,2,1-ij]quinolin-2-yl)butanamide

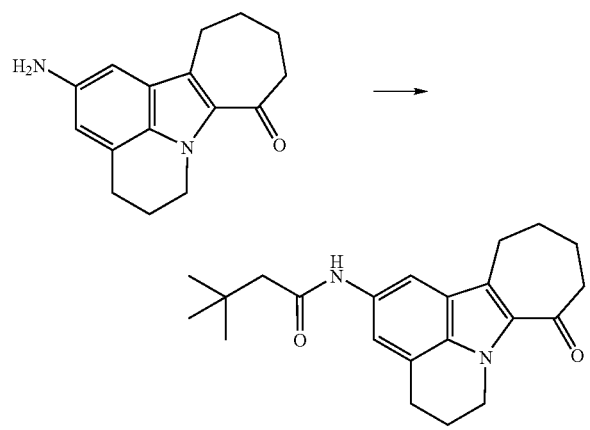

Following the procedure of Example 1, Step 4, 8-oxo-5,6,9,10,11,12-hexahydro-4H,8H-cyclohepta[4,5]pyrrolo[3,2,1-ij]quinolin-2-amine (0.65 g, 0.27 mmol), t-butylacetyl chloride (0.038 mL, 0.27 mmol) and poly-(4-vinylpyridine) (500 mg) in dichloromethane (12 mL) provided 3,3-dimethyl-N-(8-oxo-5,6,9,10,11,12-hexahydro-4H,8H-cyclohepta[4,5]pyrrolo[3,2,1-ij]quinolin-2-yl)butanamide (40 mg). MS (ESI) m/z 353.

Assessment of the Ability of Test Compounds to Inhibit Contractions of Isolated Rat Bladder Strips The compounds of the examples were tested to determine their ability to inhibit contractions of isolated rat bladder strips. See Foster, C. D. et al. Br. J. Pharmacol. 97:281-291, 1989; and Fujii, K. et al. Br. J. Pharmacol. 99:779-785, 1990. Malmgren, A. et al. J. Urol. 143:828-834, 1990, each of which are incorporated herein by reference in its entirety.

Male Sprague-Dawley rats (150-200 g) were obtained from ACE animal suppliers. Animals were allowed free access to food and water.

Animals were euthanized by $CO_2$ asphyxiation followed by a bilateral thoracotomy. The bladder was removed into warm (37 deg. C.) physiological salt solution (PSS) of the following composition (mM): NaCl, 118.4; KCl, 4.7; $CaCl_2$, 2.5; $MgSO_4 \cdot 7H_2O$, 1.2; $NaHCO_3$, 24.9; $KH_2PO_4$, 1.2; glucose, 11.1; EDTA, 0.023; gassed with 95% $O_2$/5% $CO_2$; pH 7.4. The bladder was opened and then cut into strips 1-2 mm in width and 7-10 mm in length. The strips were subsequently suspended in a 10 ml tissue bath under an initial resting tension of 1.5 g. The strips were held in place by two surgical clips one of which was attached to a fixed hook while the other was attached to an isometric force transducer. The preparations, which usually exhibit small spontaneous contractions, were allowed to recover for a period of one hour prior to a challenge with 0.1 uM carbachol. The carbachol was then washed out and the tissue allowed to relax to its resting level of activity. Following a further thirty minute period of recovery an additional 15 mM KCl was introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle were introduced into the tissue bath. Contractile activity was measured for each compound or vehicle concentration during the last minute of a thirty minute challenge.

Isometric force developed by the bladder strips was measured using a force transducer and recorded on a polygraph. Contractile activity was assessed by measuring either the average amplitude of the contractions (baseline to peak force) occurring during a one min period or, preferably, by integrating the contractile activity with respect to time (one minute measuring period).

The percentage inhibition of contractile activity evoked by each concentration of a given test compounds was used to generate a concentration-response curve. The concentration of test compound required to elicit 50% inhibition of pre-drug contractile activity (IC50 concentration) was calculated from this concentration-response curve. The maximum percentage inhibition of contractile activity evoked by a test compound was also recorded for concentrations of test compound <- or 30 uM. The results are summarized in Table 1.

TABLE 1

| Example | $IC_{50}$ (µM) | % Inhibition of Contractility @ 3 µM | % Enhancement of Contractility @ 3 µM |
|---|---|---|---|
| 1 | 0.03-0.07 | | |
| 2 | | | 20-100% |
| 3 | 0.4-2.6 | | |
| 4 | | 5-20% | |
| 5 | | | 60-90% |
| 6 | 0.08-0.35 | | |
| 7 | 0.4-0.55 | | |
| 8 | | | 150-200% |
| 9 | 0.05-1.0 | | |
| 10 | 0.15-0.35 | | |
| 11 | 0.65-0.70 | | |
| 12 | 0.70-1.0 | | |
| 13 | 0.50-0.60 | | |
| 14 | 0.80-1.0 | | |
| 15 | 0.30-1.2 | | |
| 16 | | | 80-100% |
| 17 | 0.4-0.8 | | |
| 18 | 0.50-0.55 | | |
| 19 | 2-3 | | |
| 20 | 0.08-0.55 | | |
| 21 | 0.16-0.70 | | |
| 22 | 0.80-1.0 | | |
| 23 | | 25-50% | |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

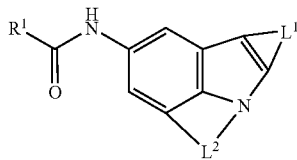

or pharmaceutically acceptable salt thereof; wherein:

$R^1$ is H, amino, $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, —$OR^2$, —$SR^2$, or —$NR^3R^4$; wherein said $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups;

$L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^vS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups;

each $R^2$, $R^3$, and $R^4$ is, independently, H, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^8$ groups;

each $R^5$ or $R^8$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$, $NR^cC(=NR^a)OR^d$, $NR^cC(=NR^a)NR^d$, halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups;

each $R^9$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $NR^{c'}C(O)R^{d'}$, $NR^{c'}C(O)OR^{d'}$, $NR^{c'}C(O)NR^{d'}$, $S(O)R^{b'}$, $S(O)NR^{e'}R^{f'}$, $S(O)_2R^{b'}$, $NR^{c'}S(O)_2R^{d'}$, $NR^{b'}S(O)_2NR^{e'}R^{f'}$, halogen, cyano, nitro, hydroxyl, carboxy, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^6$ is, independently, $OR^{o'}$, $SR^{o'}$, $C(O)R^{p'}$, $C(O)NR^{s'}R^{t'}$, $C(O)OR^{p'}$, $OC(O)R^{p'}$, $OC(O)NR^{s'}R^{t'}$, $NR^{s'}R^{t'}$, $NR^{q'}C(O)R^{r'}$, $NR^{q'}C(O)OR^{r'}$, $NR^{q'}C(O)NR^{r'}$, $S(O)R^{p'}$, $S(O)NR^{s'}R^{t'}$, $S(O)_2R^{p'}$, $NR^{q'}S(O)_2R^{r'}$, $NR^{p'}S(O)_2NR^{s'}R^{t'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^7$ is, independently, $OR^{u'}$, $SR^{u'}$, $C(O)R^{v'}$, $C(O)NR^{y'}R^{z'}$, $C(O)OR^{v'}$, $OC(O)R^{v'}$, $OC(O)NR^{y'}R^{z'}$, $NR^{y'}R^{z'}$, $NR^{w'}C(O)R^{x'}$, $NR^{w'}C(O)OR^{x'}$, $NR^{w'}C(O)NR^{x'}$, $S(O)R^{v'}$, $S(O)NR^{y'}R^{z'}$, $S(O)_2R^{v'}$, $NR^{w'}S(O)_2R^{x'}$, $NR^{v'}S(O)_2NR^{y'}R^{z'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^a$, $R^b$, $R^c$, $R^d$, $R^e$, or $R^f$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 $R^g$ groups;

or any $R^c$ and $R^d$, together with the moiety to which they are attached, form a 3-, 4-, 5-, 6- 7- or 8-membered heterocycloalkyl ring, wherein said heterocycloalkyl ring is optionally substituted with 1, 2, or 3 $R^{g'}$ groups;

or any $R^e$ and $R^f$, together with the nitrogen atom to which they are attached, form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 $R^{g''}$ groups;

each $R^g$, $R^{g'}$, or $R^{g''}$ is, independently, halogen, cyano, nitro, hydroxyl, $C_{1-6}$ alkyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^{a'}$, $R^{b'}$, $R^{c'}$, $R^{d'}$, $R^{e'}$, or $R^{f'}$ is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl, or any $R^{c'}$ and $R^{d'}$, together with the moiety to which they are attached, form a 3-, 4-, 5-, 6- 7- or 8-membered heterocycloalkyl ring;

or any $R^{e'}$ and $R^{f'}$, together with the nitrogen atom to which they are attached, form a 3-, 4-, 5-, 6- 7- or 8-membered heterocycloalkyl ring or 5-, 6-, 7- or 8-membered heteroaryl ring;

each $R^o R^p$, $R^q$, $R^r$, $R^s$, $R^t$, $R^u$, $R^v$, $R^y$, or $R^z$, is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, $C_{1-6}$ alkyl, $C_{1-6}$ haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any $R^q$ and $R^r$, together with the moiety to which they are attached, form a 3-, 4-, 5-, 6- 7- or 8-membered heterocycloalkyl ring;

or any $R^s$ and $R^t$, together with the nitrogen atom to which they are attached, form a 3-, 4-, 5-, 6- 7- or 8-membered heterocycloalkyl ring or 5-, 6-, 7- or 8-membered heteroaryl ring;

or any $R^w$ and $R^x$, together with the moiety to which they are attached, form a 3-, 4-, 5-, 6- 7- or 8-membered heterocycloalkyl ring;

or any $R^y$ and $R^z$, together with the nitrogen atom to which they are attached, form a 3-, 4-, 5-, 6- 7- or 8-membered heterocycloalkyl ring or 5-, 6-, 7- or 8-membered heteroaryl ring; and each $R^{o'}$, $R^{p'}$, $R^{q'}$, $R^{r'}$, $R^{s'}$, $R^{t'}$, $R^{u'}$, $R^{v'}$, $R^{y'}$, or $R^{z'}$, is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{q'}$ and $R^{r'}$, together with the moiety to which they are attached, form a 3-, 4-, 5-, 6- 7- or 8-membered heterocyclic ring;

or any $R^{s'}$ and $R^{t'}$, together with the nitrogen atom to which they are attached, form a 3-, 4-, 5-, 6- 7- or 8-membered heterocycloalkyl ring or 5-, 6-, 7- or 8-membered heteroaryl ring;

or any $R^{w'}$ and $R^{x'}$, together with the moiety to which they are attached, form a 3-, 4-, 5-, 6- 7- or 8-membered heterocycloalkyl ring;

or any $R^{y'}$ and $R^{z'}$, together with the nitrogen atom to which they are attached, form a 3-, 4-, 5-, 6- 7- or 8-membered heterocycloalkyl ring or 5-, 6-, 7- or 8-membered heteroaryl ring;

provided that the compound is not N-(4-oxo-5,6,8,9,10,11-hexahydro-4H-pyrido[3,2,1-jk]carbazol-2-yl)-acetamide, or pharmaceutically acceptable salt thereof.

2. The compound of claim 1 wherein $R^1$ is H, $C_{1-12}$ alkyl, $C_{2-12}$ alkenyl, $C_{2-12}$ alkynyl, $C_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl, wherein said $C_{1-12}$ alkyl, $C_{2-12}$ alkenyl, $C_{2-12}$ alkynyl, $C_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 $R^5$ groups.

3. The compound of claim 1 wherein $R^1$ is H, $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups.

4. The compound of claim 1 wherein $R^1$ is $C_{1-12}$ alkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups.

5. The compound of claim 1 wherein $R^1$ is $C_{1-12}$ alkyl, cycloalkyl, cycloalkylalkyl, heterocycloalkyl, heterocycloalkylalkyl, arylalkyl, or heteroaryl, wherein said $C_{1-12}$ alkyl, $C_{2-12}$ alkynyl, cycloalkyl, cycloalkylalkyl, heterocycloalkyl, heterocycloalkylalkyl, arylalkyl, and heteroaryl are each optionally substituted by 1, 2, 3, or 4 $R^5$ groups.

6. The compound of claim 1 wherein $R^1$ is $C_{1-12}$ alkyl, cycloalkyl, cycloalkylalkyl, heterocycloalkyl, heterocycloalkylalkyl, arylalkyl, or heteroaryl.

7. The compound of claim 1 wherein $R^1$ is methyl, ethyl, n-butyl, isobutyl, tert-butyl, neopentyl, n-pentyl, n-hexyl, cyclohexyl, cyclopentylethyl, benzyl, phenylethyl, or thiophen-2-yl.

8. The compound of claim 1 wherein $L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups.

9. The compound of claim 1 wherein $L^1$ is a $C_{4-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $NR^sR^t$, $NR^qC(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups.

10. The compound of claim 1 wherein $L^1$ is a $C_{4-6}$ alkylene bridge which is optionally substituted with 1, 2, 3, or 4 groups independently selected from $OR^o$, $C(O)R^p$, $NR^sR^t$, oxo, halogen, amino, $C_{1-6}$alkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups.

11. The compound of claim 1 wherein $L^1$ is a $C_{4-6}$ alkylene bridge which is optionally substituted with 1, 2, 3, or 4 groups independently selected from $OR^o$, $C(O)R^p$, $NR^sR^t$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl.

12. The compound of claim 1 wherein $L^1$ is a $C_{4-6}$ alkylene bridge which is optionally substituted with 1, 2, 3, or 4 oxo groups.

13. The compound of claim 1 wherein $L^1$ is a $C_{4-6}$ alkylene bridge which is optionally substituted with 1 oxo group.

14. The compound of claim 1 wherein $L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups.

15. The compound of claim 1 wherein $L^2$ is a $C_{2-3}$ alkylene bridge which is optionally substituted with 1, 2, 3, or 4 groups independently selected from $OR^u$, $SR^u$, $C(O)R^v$, $C(O)NR^yR^z$, $C(O)OR^v$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl are each optionally substituted by 1, 2, or 3 $R^7$ groups.

16. The compound of claim 1 wherein $L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl, are each optionally substituted by 1, 2, or 3 $R^7$ groups.

17. The compound of claim 1 wherein $L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl.

18. The compound of claim 1 wherein $L^2$ is an unsubstituted $C_{2-3}$ alkylene bridge.

19. The compound of claim 1 wherein:
$L_1$ is an unsubstituted $C_6$ alkylene bridge; and
$L_2$ is an unsubstituted $C_2$ alkylene bridge.

20. The compound of claim 1 wherein:
$L_1$ is an unsubstituted $C_5$ alkylene bridge; and
$L_2$ is an unsubstituted $C_3$ alkylene bridge.

21. The compound of claim 1 wherein:
$L_1$ is a $C_5$ alkylene bridge substituted with 1 oxo group; and
$L_2$ is an unsubstituted $C_3$ alkylene bridge.

22. The compound of claim 1 wherein:
$L_1$ is an unsubstituted $C_5$ alkylene bridge; and
$L_2$ is an unsubstituted $C_2$ alkylene bridge.

23. The compound of claim 1 wherein:
$L_1$ is an unsubstituted $C_4$ alkylene bridge; and
$L_2$ is an unsubstituted $C_3$ alkylene bridge.

24. The compound of claim 1 wherein:
$R^1$ is H, $C_{1-12}$ alkyl, $C_{2-12}$ alkenyl, $C_{2-12}$ alkynyl, $C_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl, wherein said $C_{1-12}$ alkyl, $C_{2-12}$ alkenyl, $C_{2-12}$ alkynyl, $C_{1-12}$ haloalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl is optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^q\text{-}C(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups; and $L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups.

25. The compound of claim 1 wherein:

$R^1$ is H, $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^q\text{-}C(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups; and $L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups.

26. The compound of claim 1 wherein:

$R^1$ is H, $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, $C_{1-12}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups;

$L^1$ is a $C_{4-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $NR^sR^t$, $NR^q\text{-}C(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups; and $L^2$ is a $C_{2-3}$ alkylene bridge which is optionally substituted with 1, 2, 3, or 4 groups independently selected from $OR^u$, $SR^u$, $C(O)R^v$, $C(O)NR^yR^z$, $C(O)OR^v$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^yS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^7$ groups.

27. The compound of claim 1 wherein:
$R^1$ is $C_{1-12}$ alkyl, cycloalkyl, cycloalkylalkyl, heterocycloalkyl, heterocycloalkylalkyl, aryl, arylalkyl, heteroaryl, or heteroarylalkyl, wherein said $C_{1-12}$ alkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^5$ groups;
$L^1$ is a $C_{4-6}$ alkylene bridge which is optionally substituted with 1, 2, 3, or 4 groups independently selected from $OR^o$, $C(O)R^p$, $NR^sR^t$, oxo, halogen, amino, $C_{1-6}$ alkyl, cycloalkyl, cycloalkylalkyl, heterocycloalkyl, heterocycloalkylalkyl, aryl, arylalkyl, heteroaryl, or heteroarylalkyl; wherein said $C_{1-6}$alkyl, cycloalkyl, cycloalkylalkyl, heterocycloalkyl, heterocycloalkylalkyl, aryl, arylalkyl, heteroaryl, and heteroarylalkyl are each optionally substituted by 1, 2, or 3 $R^6$ groups; and
$L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, or heteroarylalkyl wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl, are each optionally substituted by 1, 2, or 3 $R^7$ groups.

28. The compound of claim 1 wherein:
$R^1$ is $C_{1-12}$ alkyl, cycloalkyl, cycloalkylalkyl, heterocycloalkyl, heterocycloalkylalkyl, arylalkyl, or heteroaryl, wherein said $C_{1-12}$ alkyl, $C_{2-12}$ alkynyl, cycloalkyl, cycloalkylalkyl, heterocycloalkyl, heterocycloalkylalkyl, arylalkyl, and heteroaryl are each optionally substituted by 1, 2, 3, or 4 $R^5$ groups;
$L^1$ is a $C_{4-6}$ alkylene bridge which is optionally substituted with 1, 2, 3, or 4 groups independently selected from $OR^o$, $C(O)R^p$, $NR^sR^t$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl; and
$L^2$ is a $C_{2-3}$ alkylene bridge which is optionally substituted with 1, 2, 3, or 4 groups independently selected from $OR^u$, $C(O)R^v$, $NR^yR^z$, oxo, halogen, amino, $C_{1-6}$ alkyl, cycloalkyl, cycloalkylalkyl, heterocycloalkyl, heterocycloalkylalkyl, aryl, arylalkyl, heteroaryl, and heteroarylalkyl.

29. The compound of claim 1 wherein:
$R^1$ is $C_{1-12}$ alkyl, cycloalkyl, cycloalkylalkyl, heterocycloalkyl, heterocycloalkylalkyl, arylalkyl, or heteroaryl, wherein said $C_{1-12}$ alkyl, $C_{2-12}$ alkynyl, cycloalkyl, cycloalkylalkyl, heterocycloalkyl, heterocycloalkylalkyl, arylalkyl, and heteroaryl are each optionally substituted by 1, 2, 3, or 4 $R^5$ groups;
$L^1$ is a $C_{4-6}$ alkylene bridge which is optionally substituted with 1 oxo group; and
$L^2$ is an unsubstituted $C_{2-3}$ alkylene bridge.

30. The compound of claim 1 wherein:
$R^1$ is $C_{1-12}$ alkyl, cycloalkyl, cycloalkylalkyl, heterocycloalkyl, heterocycloalkylalkyl, arylalkyl, or heteroaryl;
$L^1$ is a $C_{4-6}$ alkylene bridge which is optionally substituted with 1 oxo group; and
$L^2$ is an unsubstituted $C_{2-3}$ alkylene bridge.

31. The compound of claim 1 wherein:
$R^1$ is methyl, ethyl, n-butyl, isobutyl, tert-butyl, neopentyl, n-pentyl, n-hexyl, cyclohexyl, cyclopentylethyl, benzyl, phenylethyl, or thiophen-2-yl;
$L^1$ is a $C_{4-6}$ alkylene bridge which is optionally substituted with 1 oxo group; and
$L^2$ is an unsubstituted $C_{2-3}$ alkylene bridge.

32. The compound of claim 1 wherein said compound is:
N-5,6,9,10,11,12-hexahydro-4H,8H-cyclohepta[4,5]pyrrolo[3,2,1-ij]quinolin-2-yl-3,3-dimethylbutanamide;
N-5,6,9,10,11,12-hexahydro-4H,8H-cyclohepta[4,5]pyrrolo[3,2,1-ij]quinolin-2-yl-2,2-dimethylpropanamide;
N-5,6,9,10,11,12-hexahydro-4H,8H-cyclohepta[4,5]pyrrolo[3,2,1-ij]quinolin-2-ylhexanamide;
N-5,6,9,10,11,12-hexahydro-4H,8H-cyclohepta[4,5]pyrrolo[3,2,1-ij]quinolin-2-yl-3-phenylpropanamide;
N-5,6,9,10,11,12-hexahydro-4H,8H-cyclohepta[4,5]pyrrolo[3,2,1-ij]quinolin-2-ylthiophene-2-carboxamide;
N-5,6,9,10,11,12-hexahydro-4H,8H-cyclohepta[4,5]pyrrolo[3,2,1-ij]quinolin-2-yl-3-methylbutanamide;
N-5,6,9,10,11,12-hexahydro-4H,8H-cyclohepta[4,5]pyrrolo[3,2,1-ij]quinolin-2-ylpropanamide;
N-5,6,9,10,11,12-hexahydro-4H,8H-cyclohepta[4,5]pyrrolo[3,2,1-ij]quinolin-2-ylcyclohexanecarboxamide;
N-5,6,9,10,11,12-hexahydro-4H,8H-cyclohepta[4,5]pyrrolo[3,2,1-ij]quinolin-2-ylpentanamide;
N-4,5,8,9,10,11-hexahydro-7H-cyclohepta[b]pyrrolo[3,2,1-hi]indol-2-yl-3,3-dimethylbutanamide;
N-4,5,8,9,10,11-hexahydro-7H-cyclohepta[b]pyrrolo[3,2,1-hi]indol-2-ylacetamide;
N-4,5,8,9,10,11-hexahydro-7H-cyclohepta[b]pyrrolo[3,2,1-hi]indol-2-ylpentanamide;
N-4,5,8,9,10,11-hexahydro-7H-cyclohepta[b]pyrrolo[3,2,1-hi]indol-2-yl-2-phenylacetamide;
N-4,5,8,9,10,11-hexahydro-7H-cyclohepta[b]pyrrolo[3,2,1-hi]indol-2-yl-3-methylbutanamide;
3-cyclopentyl-N-4,5,8,9,10,11-hexahydro-7H-cyclohepta[b]pyrrolo[3,2,1-hi]indol-2-ylpropanamide;
N-5,6,8,9,10,11-hexahydro-4H-pyrido[3,2,1-jk]carbazol-2-yl-3,3-dimethylbutanamide;
N-5,6,8,9,10,11-hexahydro-4H-pyrido[3,2,1-jk]carbazol-2-ylhexanamide;
N-5,6,8,9,10,11-hexahydro-4H-pyrido[3,2,1-jk]carbazol-2-yl-3-methylbutanamide;
N-5,6,8,9,10,11-hexahydro-4H-pyrido[3,2,1-jk]carbazol-2-ylacetamide;
N-4,5,7,8,9,10,11,12-octahydrocycloocta[b]pyrrolo[3,2,1-hi]indol-2-ylhexanamide;
3,3-dimethyl-N-4,5,7,8,9,10,11,12-octahydrocycloocta[b]pyrrolo[3,2,1-hi]indol-2-ylbutanamide;
N-4,5,7,8,9,10,11,12-octahydrocycloocta[b]pyrrolo[3,2,1-hi]indol-2-ylheptanamide; or
3,3-dimethyl-N-(8-oxo-5,6,9,10,11,12-hexahydro-4H,8H-cyclohepta[4,5]pyrrolo[3,2,1-ij]quinolin-2-yl)butanamide;

or pharmaceutically acceptable salt thereof.

33. A pharmaceutical composition comprising a compound of claim 1 and a pharmaceutically acceptable carrier.

34. A synthetic process comprising reacting a compound of Formula VIII:

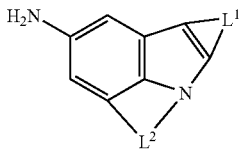

VIII with a compound of Formula IX:

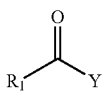

IX under conditions and for a time sufficient to produce a compound of Formula I:

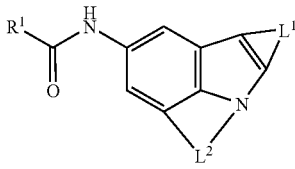

I wherein:

R$^1$ is H, amino, C$_{1-12}$ alkyl, C$_{2-12}$ alkenyl, C$_{2-12}$ alkynyl, C$_{1-12}$ haloalkyl, C$_{1-12}$ haloalkoxy, C$_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, —OR$^2$, —SR$^2$, or —NR$^3$R$^4$; wherein said C$_{1-12}$ alkyl, C$_{2-12}$ alkenyl, C$_{2-12}$ alkynyl, C$_{1-12}$ haloalkyl, C$_{1-12}$ haloalkoxy, C$_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 R$^5$ groups;

L$^1$ is a C$_{3-6}$ alkylene bridge which is optionally substituted with 1, 2, 3, or 4 groups independently selected from OR$^o$, SR$^o$, C(O)R$^p$, C(O)NR$^s$R$^t$, C(O)OR$^p$, OC(O)R$^p$, OC(O)NR$^s$R$^t$, NR$^s$R$^t$, NR$^q$C(O)R$^r$, NR$^q$C(O)OR$^r$, NR$^q$C(O)NR$^r$, S(O)R$^p$, S(O)NR$^s$R$^t$, S(O)$_2$R$^p$, NR$^q$S(O)$_2$R$^r$, NR$^p$S(O)$_2$NR$^s$R$^t$, oxo, halogen, cyano, nitro, hydroxyl, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 R$^6$ groups;

L$^2$ is a C$_{2-5}$ alkylene bridge which is optionally substituted with 1, 2, 3, or 4 groups independently selected from OR$^u$, SR$^u$, C(O)R$^v$, C(O)NR$^y$R$^z$, C(O)OR$^v$, OC(O)R$^v$, OC(O)NR$^y$R$^z$, NR$^y$R$^z$, NR$^w$C(O)R$^x$, NR$^w$C(O)OR$^x$, NR$^w$C(O)NR$^x$, S(O)R$^v$, S(O)NR$^y$R$^z$, S(O)$_2$R$^v$, NR$^w$S(O)$_2$R$^x$, NR$^y$S(O)$_2$NR$^y$R$^z$, oxo, halogen, cyano, nitro, hydroxyl, amino, C$_{1-6}$alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl; wherein said C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 R$^7$ groups;

each R$^2$, R$^3$, and R$^4$ is, independently, H, C$_{1-6}$ alkyl, C$_{1-6}$ alkenyl, C$_{1-6}$ alkynyl, C$_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ alkenyl, C$_{1-6}$ alkynyl, C$_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 R$^8$ groups;

each R$^5$ or R$^8$ is, independently, OR$^a$, SR$^a$, C(O)R$^b$, C(O)NR$^e$R$^f$, C(O)OR$^b$, OC(O)R$^b$, OC(O)NR$^e$R$^f$, NR$^e$R$^f$, NR$^c$C(O)R$^d$, NR$^c$C(O)OR$^d$, NR$^c$C(O)NR$^d$, S(O)R$^b$, S(O)NR$^e$R$^f$, S(O)$_2$R$^b$, NR$^c$S(O)$_2$R$^d$, NR$^b$S(O)$_2$NR$^e$R$^f$, C(=NR$^a$)R$^b$, C(=NR$^a$)NR$^b$, C(=NR$^a$)OR$^b$, OC(=NR$^a$)R$^b$, OC(=NR$^a$)NR$^b$, NR$^c$C(=NR$^a$)R$^d$, NR$^c$C(=NR$^a$)OR$^d$, NR$^c$C(=NR$^a$)NR$^d$, halogen, cyano, nitro, hydroxyl, carboxy, amino, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 R$^9$ groups;

each R$^9$ is, independently, OR$^{a'}$, SR$^{a'}$, C(O)R$^{b'}$, C(O)NR$^{e'}$R$^{f'}$, C(O)OR$^{b'}$, OC(O)R$^{b'}$, OC(O)NR$^{e'}$R$^{f'}$, NR$^{e'}$R$^{f'}$, NR$^{c'}$C(O)R$^{d'}$, NR$^{c'}$C(O)OR$^{d'}$, NR$^{c'}$C(O)NR$^{d'}$, S(O)R$^{b'}$, S(O)NR$^{e'}$R$^{f'}$, S(O)$_2$R$^{b'}$, NR$^{c'}$S(O)$_2$R$^{d'}$, NR$^{b'}$S(O)$_2$NR$^{e'}$R$^{f'}$, halogen, cyano, nitro, hydroxyl, carboxy, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each R⁶ is, independently, OR°', SR°', C(O)Rᵖ', C(O)NRˢ'Rᵗ', C(O)ORᵖ', OC(O)Rᵖ', OC(O)NRˢ'Rᵗ', NRˢ'Rᵗ', NRᵠ'C(O)Rʳ', NRᵠ'C(O)ORʳ', NRᵠ'C(O)NRʳ', S(O)Rᵖ', S(O)NRˢ'Rᵗ', S(O)₂Rᵖ', NRᵠ'S(O)₂Rʳ', NRᵖ'S(O)₂NRˢ'Rᵗ', halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each R⁷ is, independently, ORᵘ', SRᵘ', C(O)Rᵛ', C(O)NRʸ'Rᶻ', C(O)ORᵛ', OC(O)Rᵛ', OC(O)NRʸ'Rᶻ', NRʸ'Rᶻ', NRʷ'C(O)Rˣ', NRʷ'C(O)ORˣ', NRʷ'C(O)NRˣ', S(O)Rᵛ', S(O)NRʸ'Rᶻ', S(O)₂Rᵛ', NRʷ'S(O)₂Rˣ', NRᵛ'S(O)₂NRʸ'Rᶻ', halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each Rᵃ, Rᵇ, Rᶜ, Rᵈ, Rᵉ, or Rᶠ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 Rᵍ groups;

or any Rᶜ and Rᵈ, together with the moiety to which they are attached, form a 3-, 4-, 5-, 6- 7- or 8-membered heterocycloalkyl ring, wherein said heterocycloalkyl ring is optionally substituted with 1, 2, or 3 Rᵍ' groups;

or any Rᵉ and Rᶠ, together with the nitrogen atom to which they are attached, form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 Rᵍ'' groups;

each Rᵍ, Rᵍ', or Rᵍ'' is, independently, halogen, cyano, nitro, hydroxyl, $C_{1-6}$ alkyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each Rᵃ', Rᵇ', Rᶜ', Rᵈ', Rᵉ', or Rᶠ' is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any Rᶜ' and Rᵈ', together with the moiety to which they are attached, form a 3-, 4-, 5-, 6- 7- or 8-membered heterocycloalkyl ring;

or any Rᵉ' and Rᶠ', together with the nitrogen atom to which they are attached, form a 3-, 4-, 5-, 6- 7- or 8-membered heterocycloalkyl ring or 5-, 6-, 7- or 8-membered heteroaryl ring;

each R°Rᵖ, Rᵠ, Rʳ, Rˢ, Rᵗ, Rᵘ, Rᵛ, Rʸ, or Rᶻ, is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, $C_{1-6}$ alkyl, $C_{1-6}$ haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any Rᵠ and Rʳ, together with the moiety to which they are attached, form a 3-, 4-, 5-, 6- 7- or 8-membered heterocycloalkyl ring;

or any Rˢ and Rᵗ, together with the nitrogen atom to which they are attached, form a 3-, 4-, 5-, 6- 7- or 8-membered heterocycloalkyl ring or 5-, 6-, 7- or 8-membered heteroaryl ring;

or any Rʷ and Rˣ, together with the moiety to which they are attached, form a 3-, 4-, 5-, 6- 7- or 8-membered heterocycloalkyl ring;

or any Rʸ and Rᶻ, together with the nitrogen atom to which they are attached, form a 3-, 4-, 5-, 6- 7- or 8-membered heterocycloalkyl ring or 5-, 6-, 7- or 8-membered heteroaryl ring;

each R°', Rᵖ', Rᵠ', Rʳ', Rˢ', Rᵗ', Rᵘ', Rᵛ', Rʸ', or Rᶻ', is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any Rᵠ' and Rʳ', together with the moiety to which they are attached, form a 3-, 4-, 5-, 6- 7- or 8-membered heterocyclic ring;

or any Rˢ' and Rᵗ', together with the nitrogen atom to which they are attached, form a 3-, 4-, 5-, 6- 7- or 8-membered heterocycloalkyl ring or 5-, 6-, 7- or 8-membered heteroaryl ring;

or any Rʷ' and Rˣ', together with the moiety to which they are attached, form a 3-, 4-, 5-, 6- 7- or 8-membered heterocycloalkyl ring;

or any Rʸ' and Rᶻ', together with the nitrogen atom to which they are attached, form a 3-, 4-, 5-, 6- 7- or 8-membered heterocycloalkyl ring or 5-, 6-, 7- or 8-membered heteroaryl ring;

Y is halogen, $C_{1-12}$ alkoxy, hydroxyl, amino, OC(O)Rʸʸ, or OC(O)R₁; and

Rʸʸ is $C_{1-12}$ alkyl;

provided that the compound of Formula I is not N-(4-oxo-5,6,8,9,10,11-hexahydro-4H-pyrido[3,2,1-jk]carbazol-2-yl)-acetamide, or pharmaceutically acceptable salt thereof.

35. The synthetic process of claim 34 wherein Y is halogen.

36. The synthetic process of claim 34 wherein Y is chloro.

37. The synthetic process of claim 34 wherein the compound of Formula VIII is produced by a process comprising:

(a) reacting a compound of Formula IV:

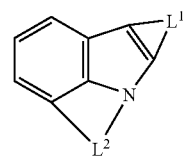

IV with a nitrating agent under conditions and for a time sufficient to produce a compound of Formula VII: and

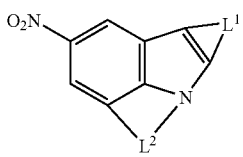
VII (b) reducing the nitro group of the compound of Formula VII under conditions and for a time sufficient to produce a compound of Formula VIII.

38. The synthetic process of claim 37 wherein said nitrating agent comprises nitric acid, $N_2O_4$, $N_2O_5$, esters of nitric acid, metallic nitrites, or nitronium salts.

39. The synthetic process of claim 37 wherein said nitrating agent comprises potassium nitrate.

40. The synthetic process of claim 37 wherein said reducing comprises reacting a compound of Formula VII with a reducing agent comprising zinc, tin, iron, lithium aluminum hydride, a sulfide, hot liquid paraffin, aluminum hydride-aluminum chloride, hydrazine, sodium dihydro(trithio)borate, or hydrogen gas.

41. The synthetic process of claim 37 wherein the compound of Formula IV is produced by a process comprising reacting a compound of Formula II:

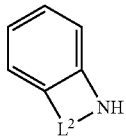
II with a compound of Formula III:

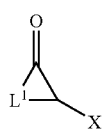
III under conditions and for a time sufficient to form a compound of Formula IV; wherein X is halogen.

42. The synthetic process of claim 41 wherein X is chloro.

43. The synthetic process of claim 37 wherein the compound of Formula IV is produced by a process comprising reacting a compound of Formula V:

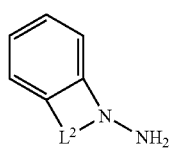
V with a compound of Formula VI:

VI in the presence of a Fischer indole catalyst under conditions and for a time sufficient to form said compound of Formula IV.

44. The synthetic process of claim 43 wherein said Fischer indole catalyst comprises a protic acid, Lewis acid, or metallic halide.

45. The synthetic process of claim 43 wherein said Fischer indole catalyst is sulfuric acid, hydrochloric acid, polyphosphoric acid, zinc chloride, aluminum chloride, boron trifluoride, or iron chloride.

46. The synthetic process of claim 43 wherein said Fischer indole catalyst is sulfuric acid.

47. A synthetic process comprising reacting a compound of Formula XV:

XV with a compound of Formula III:

III under conditions and for a time sufficient to produce a compound of Formula I:

I wherein:
$R^1$ is H, amino, $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, $-OR^2$, $-SR^2$, or $-NR^3R^4$; wherein said $C_{1-12}$ alkyl, $C_{2-12}$ alkenyl, $C_{2-12}$ alkynyl, $C_{1-12}$ haloalkyl, $C_{1-12}$ haloalkoxy, $C_{1-12}$ alkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, 3, or 4 $R^5$ groups;

$L^1$ is a $C_{3-6}$ alkylene bridge which is optionally substituted with 1, 2, 3, or 4 groups independently selected from $OR^o$, $SR^o$, $C(O)R^p$, $C(O)NR^sR^t$, $C(O)OR^p$, $OC(O)R^p$, $OC(O)NR^sR^t$, $NR^sR^t$, $NR^qC(O)R^r$, $NR^qC(O)OR^r$, $NR^q-C(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^6$ groups;

$L^2$ is a $C_{2-5}$ alkylene bridge which is optionally substituted with 1, 2, 3, or 4 groups independently selected from $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, $S(O)R^v$, $S(O)NR^yR^z$, $S(O)_2R^v$, $NR^wS(O)_2R^x$, $NR^vS(O)_2NR^yR^z$, oxo, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, or heteroarylalkynyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted by 1, 2, or 3 $R^7$ groups;

each $R^2$, $R^3$, and $R^4$ is, independently, H, $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted by 1, 2, 3, or 4 $R^8$ groups;

each $R^5$ or $R^8$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$, $NR^cC(=NR^a)OR^d$, $NR^cC(=NR^a)NR^d$, halogen, cyano, nitro, hydroxyl, carboxy, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted by 1, 2, 3 or 4 $R^9$ groups;

each $R^9$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $NR^{c'}C(O)R^{d'}$, $NR^{c'}C(O)OR^{d'}$, $NR^{c'}C(O)NR^{d'}$, $S(O)R^{b'}$, $S(O)NR^{e'}R^{f'}$, $S(O)_2R^{b'}$, $NR^{c'}S(O)_2R^{d'}$, $NR^{b'}S(O)_2NR^{e'}R^{f'}$, halogen, cyano, nitro, hydroxyl, carboxy, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^6$ is, independently, $OR^{o'}$, $SR^{o'}$, $C(O)R^{p'}$, $C(O)NR^{s'}R^{t'}$, $C(O)OR^{p'}$, $OC(O)R^{p'}$, $OC(O)NR^{s'}R^{t'}$, $NR^{s'}R^{t'}$, $NR^{q'}C(O)R^{r'}$, $NR^{q'}C(O)OR^{r'}$, $NR^{q'}C(O)NR^{r'}$, $S(O)R^{p'}$, $S(O)NR^{s'}R^{t'}$, $S(O)_2R^{p'}$, $NR^{q'}S(O)_2R^{r'}$, $NR^{p'}S(O)_2NR^{s'}R^{t'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^7$ is, independently, $OR^{u'}$, $SR^{u'}$, $C(O)R^{v'}$, $C(O)NR^{y'}R^{z'}$, $C(O)OR^{v'}$, $OC(O)R^{v'}$, $OC(O)NR^{y'}R^{z'}$, $NR^{y'}R^{z'}$, $NR^{w'}C(O)R^{x'}$, $NR^{w'}C(O)OR^{x'}$, $NR^{w'}C(O)NR^{x'}$, $S(O)R^{v'}$, $S(O)NR^{y'}R^{z'}$, $S(O)_2R^{v'}$, $NR^{w'}S(O)_2R^{x'}$, $NR^{v'}S(O)_2NR^{y'}R^{z'}$, halogen, cyano, nitro, hydroxyl, amino, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^a$, $R^b$, $R^c$, $R^d$, $R^e$, or $R^f$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 $R^g$ groups;

or any $R^c$ and $R^d$, together with the moiety to which they are attached, form a 3-, 4-, 5-, 6- 7- or 8-membered heterocycloalkyl ring, wherein said heterocycloalkyl ring is optionally substituted with 1, 2, or 3 $R^{g'}$ groups;

or any $R^e$ and $R^f$, together with the nitrogen atom to which they are attached, form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 $R^{g''}$ groups;

each $R^g$, $R^{g'}$, or $R^{g''}$ is, independently, halogen, cyano, nitro, hydroxyl, $C_{1-6}$ alkyl, $C_{1-6}$ haloalkyl, $C_{1-6}$ alkoxy, $C_{1-6}$ haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, alkylsulfinyl, thio, or alkylthio;

each $R^{a'}$, $R^{b'}$, $R^{c'}$, $R^{d'}$, $R^{e'}$, or $R^{f'}$ is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl,;

or any $R^{c'}$ and $R^{d'}$, together with the moiety to which they are attached, form a 3-, 4-, 5-, 6- 7- or 8-membered heterocycloalkyl ring;

or any $R^{e'}$ and $R^{f'}$, together with the nitrogen atom to which they are attached, form a 3-, 4-, 5-, 6- 7- or 8-membered heterocycloalkyl ring or 5-, 6-, 7- or 8-membered heteroaryl ring;

each $R^o$, $R^p$, $R^q$, $R^r$, $R^s$, $R^t$, $R^u$, $R^v$, $R^y$, or $R^z$, is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, $C_{1-6}$ alkyl, $C_{1-6}$ haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any $R^q$ and $R^r$, together with the moiety to which they are attached, form a 3-, 4-, 5-, 6- 7- or 8-membered heterocycloalkyl ring;

or any $R^s$ and $R^t$, together with the nitrogen atom to which they are attached, form a 3-, 4-, 5-, 6- 7- or 8-membered heterocycloalkyl ring or 5-, 6-, 7- or 8-membered heteroaryl ring;

or any $R^w$ and $R^x$, together with the moiety to which they are attached, form a 3-, 4-, 5-, 6- 7- or 8-membered heterocycloalkyl ring;

or any $R^y$ and $R^z$, together with the nitrogen atom to which they are attached, form a 3-, 4-, 5-, 6- 7- or 8-membered heterocycloalkyl ring or 5-, 6-, 7- or 8-membered heteroaryl ring; and each $R^{o'}$, $R^{p'}$, $R^{q'}$, $R^{r'}$, $R^{s'}$, $R^{t'}$, $R^{u'}$, $R^{v'}$, $R^{y'}$, or $R^{z'}$, is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{q'}$ and $R^{r'}$, together with the moiety to which they are attached, form a 3-, 4-, 5-, 6- 7- or 8-membered heterocyclic ring;

or any $R^{s'}$ and $R^{t'}$, together with the nitrogen atom to which they are attached, form a 3-, 4-, 5-, 6- 7- or 8-membered heterocycloalkyl ring or 5-, 6-, 7- or 8-membered heteroaryl ring;

or any $R^{w'}$ and $R^{x'}$, together with the moiety to which they are attached, form a 3-, 4-, 5-, 6- 7- or 8-membered heterocycloalkyl ring;

or any $R^{y'}$ and $R^{z'}$, together with the nitrogen atom to which they are attached, form a 3-, 4-, 5-, 6- 7- or 8-membered heterocycloalkyl ring or 5-, 6-, 7- or 8-membered heteroaryl ring;

X is halogen;

provided that the compound of Formula I is not N-(4-oxo-5,6,8,9,10,11-hexahydro-4H-pyrido[3,2,1-jk]carbazol-2-yl)-acetamide, or pharmaceutically acceptable salt thereof.

48. The synthetic process of claim 34 wherein:
$R^1$ is $C_{1-12}$ alkyl, cycloalkyl, cycloalkylalkyl, heterocycloalkyl, heterocycloalkylalkyl, arylalkyl, or heteroaryl;
$L^1$ is a $C_{4-6}$ alkylene bridge which is optionally substituted with 1 oxo; and
$L^2$ is an unsubstituted $C_{2-3}$ alkylene bridge.

49. The synthetic process of claim 34 wherein:
$R^1$ is methyl, ethyl, n-butyl, isobutyl, tert-butyl, neopentyl, n-pentyl, n-hexyl, cyclohexyl, cyclopentylethyl, benzyl, phenylethyl, or thiophen-2-yl;
$L^1$ is a $C_{4-6}$ alkylene bridge which is optionally substituted with 1 oxo; and
$L^2$ is an unsubstituted $C_{2-3}$ alkylene bridge.

50. The synthetic process of claim 47 wherein:
$R^1$ is $C_{1-12}$ alkyl, cycloalkyl, cycloalkylalkyl, heterocycloalkyl, heterocycloalkylalkyl, arylalkyl, or heteroaryl;
$L^1$ is a $C_{4-6}$ alkylene bridge which is optionally substituted with 1 oxo; and
$L^2$ is an unsubstituted $C_{2-3}$ alkylene bridge.

51. The synthetic process of claim 47 wherein:
$R^1$ is methyl, ethyl, n-butyl, isobutyl, tert-butyl, neopentyl, n-pentyl, n-hexyl, cyclohexyl, cyclopentylethyl, benzyl, phenylethyl, or thiophen-2-yl;
$L^1$ is a $C_{4-6}$ alkylene bridge which is optionally substituted with 1 oxo; and
$L^2$ is an unsubstituted $C_{2-3}$ alkylene bridge.

* * * * *